United States Patent [19]

Chan et al.

[11] Patent Number: 5,683,623
[45] Date of Patent: Nov. 4, 1997

[54] DIOXANE DERIVATIVES

[75] Inventors: Lawrence Chan, Northolt; John William Goodby; Peter Styring, both of Cottingham; Chuan Chu Dong, Hull, all of England

[73] Assignee: Central Research Laboratories Limited, Hayes, England

[21] Appl. No.: 392,903

[22] PCT Filed: Sep. 13, 1993

[86] PCT No.: PCT/GB93/01929

§ 371 Date: Mar. 1, 1995

§ 102(e) Date: Mar. 1, 1995

[87] PCT Pub. No.: WO94/06885

PCT Pub. Date: Mar. 31, 1994

[30] Foreign Application Priority Data

Sep. 24, 1992 [GB] United Kingdom ............. 9220189

[51] Int. Cl.[6] .................. C09K 19/34; C07D 319/06; C07D 407/00
[52] U.S. Cl. ................. 252/299.61; 549/369; 549/370
[58] Field of Search .................... 252/299.61; 549/369, 549/370

[56] References Cited

U.S. PATENT DOCUMENTS

| | | | |
|---|---|---|---|
| 4,344,856 | 8/1982 | Demus et al. | 252/299.61 |
| 4,348,324 | 9/1982 | Demus et al. | 549/369 |
| 4,450,094 | 5/1984 | Sato et al. | 252/299.61 |
| 4,486,332 | 12/1984 | Demus et al. | 252/299.61 |
| 4,853,150 | 8/1989 | Bezaborodov et al. | 252/299.61 |
| 5,171,471 | 12/1992 | Suzuki et al. | 252/299.61 |
| 5,254,698 | 10/1993 | Coates et al. | 549/369 |

FOREIGN PATENT DOCUMENTS 8908689  9/1989  WIPO.

OTHER PUBLICATIONS

Mol. Cryst Liq Crsy, 1991, vol. 221 pp. 161–164.

*Primary Examiner*—C. H. Kelly
*Attorney, Agent, or Firm*—Keck, Mahin & Cate

[57] ABSTRACT

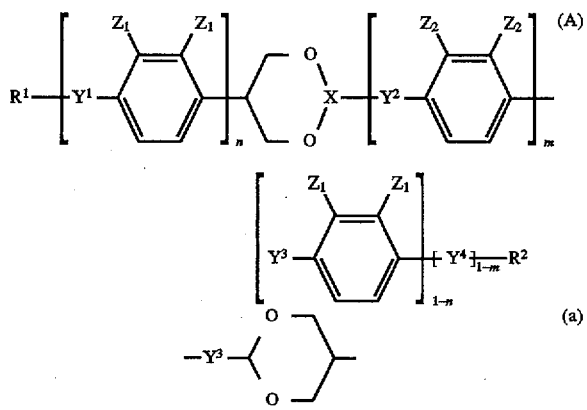

Dioxane derivatives for use as components in liquid crystal devices (LCDs) of general formula (A), wherein X is CH or B; $R^1$, $R^2$ are each $A^1$, $OA^1$, $OCOA^2$, or $COOA^2$; $A^1$ is a straight or branched chain alkyl group containing from 1 to 20 carbon atoms and may be substituted with one or more F or CN. $A^2$ is a straight or branched chain alkyl group containing from 1 to 20 carbon atoms and may be substituted with one or more F or CN and if straight may be unsubstituted. $Y^1$, $Y^2$, $Y^3$ may each be $(CH_2)_p$, $(CH_2)_pCOO$ or $OCO(CH_2)_p$; p is from 0 to 10, n is 0 or 1, m is 0 or 1, either or both of $Z_1$ and $Z_2$ are F and, when not F, are H; $Y^4$ is a covalent bond or, when n is 0, may be (a) LCDs, containing the devices exhibit very fast switching speed, bi-stable characteristics, enhanced greyscale and storage capabilities and a wide viewing angle.

11 Claims, 13 Drawing Sheets

FIG. I

FIG. 2
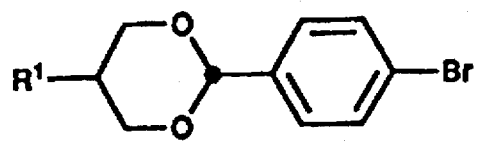
Formula 4
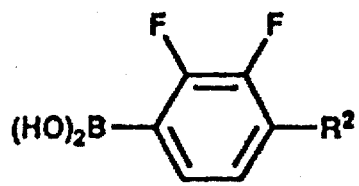
Formula 7
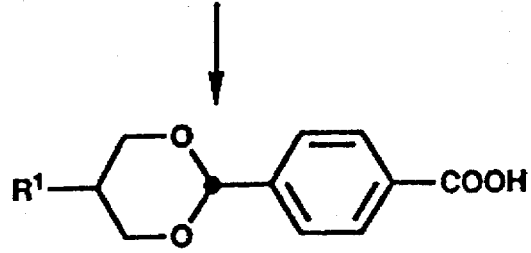
Formula 13
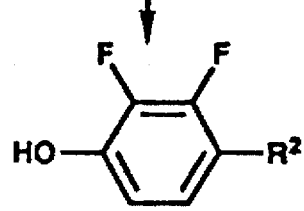
Formula 14
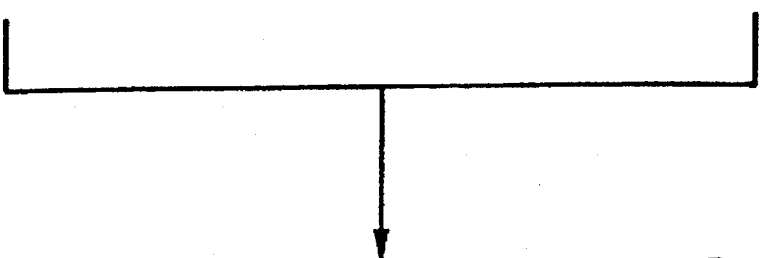
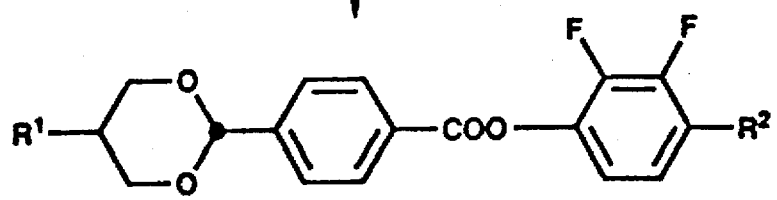
Formula 15

FIG. 7
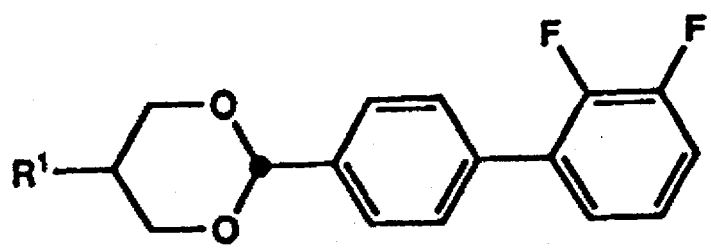
Formula 29
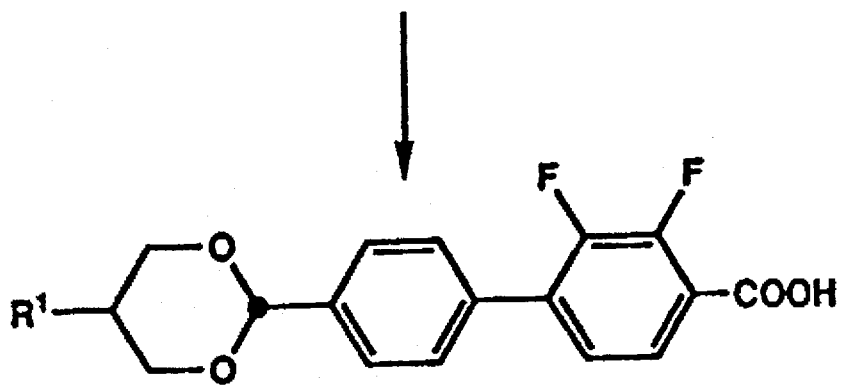
Formula 32
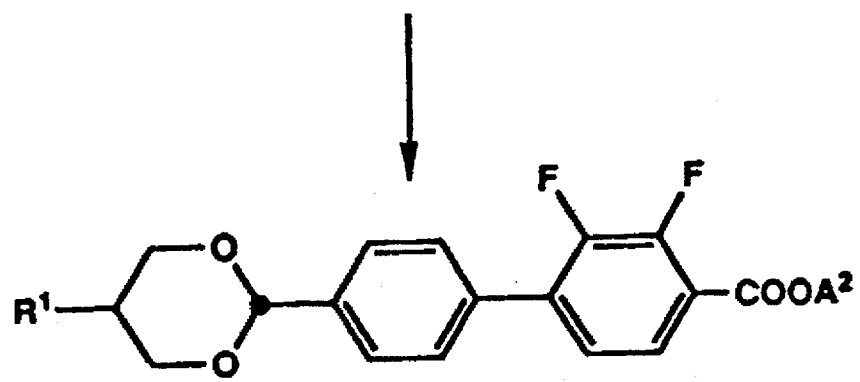
Formula 33

FORMULA A

DIOXANE DERIVATIVES

This application is a continuation of 371 application PCT GB 93/01929

This invention relates to dioxane derivatives which are useful as components in liquid crystal compositions. Such compositions may be incorporated in liquid crystal devices (LCD) and exhibit useful electro-optical effects. The invention also relates to such compositions and to the LCDs incorporating them. In particular it relates to those compositions which exhibit ferroelectric behaviour and allow the LCDs containing them to have very fast switching speed, bi-stable characteristics, enhanced greyscale and storage capabilities and wide viewing angle.

Accordingly we provide a compound of the formula A:

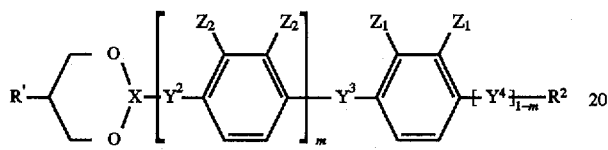

Wherein X is CH or B

R$^1$, R$^2$, are each A$^1$, OA$^1$, OCOA$^2$, or COOA$^2$

A$^1$ is a straight or branched chain alkyl group containing from 5 to 10 carbon atoms and may be substituted with one or more F or CN.

A$^2$ is a straight or optically active branched chain alkyl group containing from 5 to 10 carbon atoms and may be substituted with one or more F or CN and if straight may be unsubstituted.

Y$^2$, Y$^3$ may each be (CH$_2$)$_p$, (CH$_2$)$_p$COO or OCO(CH$_2$)$_p$
p is from 0 to 10 m is 1 or, if X is CH and Y$^3$ and Y$^4$ are covalent bonds, may be 0 either or both of Z$_1$ and Z$_2$ are F and, when not F, are H Y$^4$ is a covalent bond or

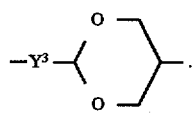

Particularly useful compounds are those wherein A$^2$ is an optically active branched chain alkyl group substituted by a single F or CN.

Individual compounds which have been found to be particularly useful include the following.

2-(4"-heptyl-2",3"-difluoro-biphen-4'-yl)-5-n-octyl-1,3-dioxane, (compound A),
2-(4"-hexyl-2",3"-difluoro-biphen-4'-yl)-5-n-octyl-1,3-dioxane, (compound B),
2-(4"-heptoxy-2",3"-difluoro-biphen-4'-yl)-5-n-nonyl-1,3-dioxane, (compound C),
2-(4"-octoxy-2",3"-difluoro-biphen-4'-yl)-5-n-nonyl-1,3-dioxane, (compound D),
2-(4"-octoxy-2",3"-difluoro-biphen-4'-yl)-5-n-heptyl-1,3-dioxane, (compound E),
2-(4"-octoxy-2',3'-difluoro-biphen-4'-yl)-5-n-heptyl-1,3-dioxane, (compound F),
4"-n-nonyl-2",3"-difluoro-4-(5'-n-pentyl-1',3'-dioxane-2-yl)benzoate, (compound G),
2",3"-difluoro-4"-n-nonoxy-4'-biphenyl)-4-n-nonyl-2,6-dioxaborinane (compound H)

BRIEF DESCRIPTION OF THE DRAWINGS

FIG. 2 is another illustration of a compound production scheme.

The compounds of this invention may be synthesised by the following methods.

Compounds of the formula 11

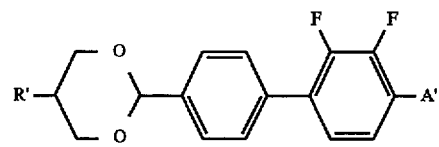

i.e. wherein, in general formula A,
X is CH;
Y$^2$, Y$^3$ are each (CH$_2$)$_p$, wherein p is 0;
m is 1;
Z$_1$ is F and Z$_2$ is H.

Figure 1:
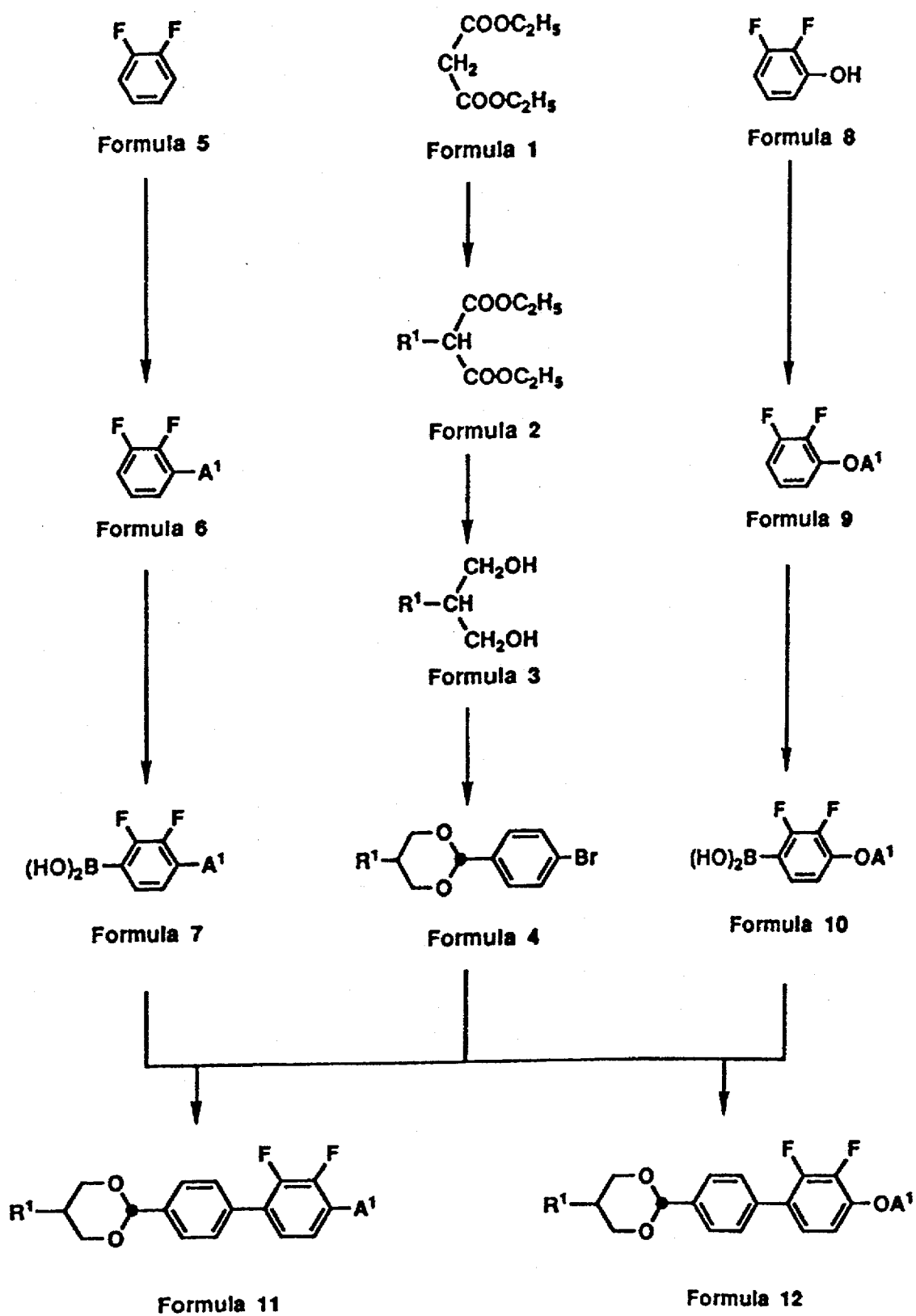
FIG. 1 is an illustration of a compound production scheme according to the invention.

These compounds are produced according to the scheme illustrated in FIG. 1. In this scheme diethyl malonate (formula 1) is reacted with the compound R$^1$Br in sodium ethoxide/ethanol to give the R$^1$-substituted diethyl malonate of formula 2. Reduction of this with lithium aluminium hydride in ether yields the corresponding diol (formula 3) which is then reacted with 4-bromobenzaldehyde and 4-toluene sulphonic acid in dry toluene to give the compound of formula 4. Reaction of 1,2-difluorobenzene (formula 5) with the compound R$^3$CHO where R$^3$ is a straight or branched chain alkyl group containing from 1 to 18 carbon atoms, optionally substituted with one or more F or CN, with n-butyllithium in tetrahydrofuran followed by treatment with phosphorous pentoxide in light petrol and then by reduction over palladium charcoal yields the compound of formula 6. Treatment of this compound with n-butyllithium in tetrahydrofuran followed by triisopropyl borate gives the compound of formula 7. Finally the compounds of formulae 4 and 7 are reacted in the presence of tetrakis(triphenylphosphine) palladium and aqueous sodium carbonate to yield the required compound of formula 11.

Compounds of Formula 12

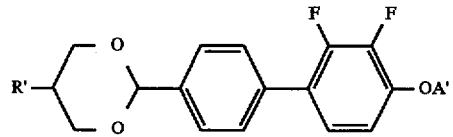

i.e. wherein, in general formula A,
X is CH;
Y$^2$, Y$^3$ are each (CH$_2$)$_p$, wherein p is 0;
m is 1;
Z$_1$ is F and Z$_2$ is H Referring again to the scheme illustrated in FIG. 1, reaction of 2,3-difluorophenol (formula 8) with the compound R2Br over potassium carbonate in acetone gives the 2,3-difluorophenyl compound of formula 9 which on reaction with firstly butyl lithium under nitrogen at −78° C. and then with tri-isopropyl borate gives the compound of formula 10. The compounds of formulae 4 and 10 are then reacted in the presence of tetrakis(triphenylphosphine) palladium and aqueous sodium carbonate to yield the required compound of formula 12.

Compounds of the formula 15

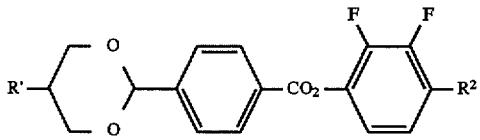

i.e. wherein, in general formula A,

X is CH;

$Y^2$ is $(CH_2)_p$, wherein p is 0;

$Y^3$ is $(CH_2)_pCOO$, wherein p is 0;

m is 1;

$Z_1$ is F and $Z_2$ is H.

These compounds are produced according to the scheme illustrated in FIG. 2. In this scheme, the compound of formula 4 (see FIG. 1 and description above), after reaction with n-butyllithium in THF under nitrogen, is poured onto carbon dioxide granules giving the 4-substituted benzoic acid of formula 13. The compound of formula 7 (see also FIG. 1) is converted to the corresponding phenol of formula 14 by reaction with hydrogen peroxide in ether. The compounds of formulae 13 and 14 are then reacted with N,N'-dicyclophenxylcarbodiimide and 4-dimethylaminopyridine to yield the required compound of formula 15.

Compounds of the formula 19

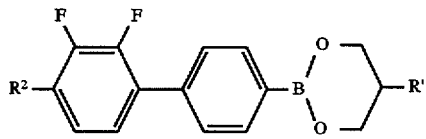

i.e. wherein, in general formula A,

X is B;

$Y^2$, $Y^3$ are each $(CH_2)_p$, wherein p is 0;

m is 1;

$Z_1$ is F and $Z_2$ is H

Figure 3:
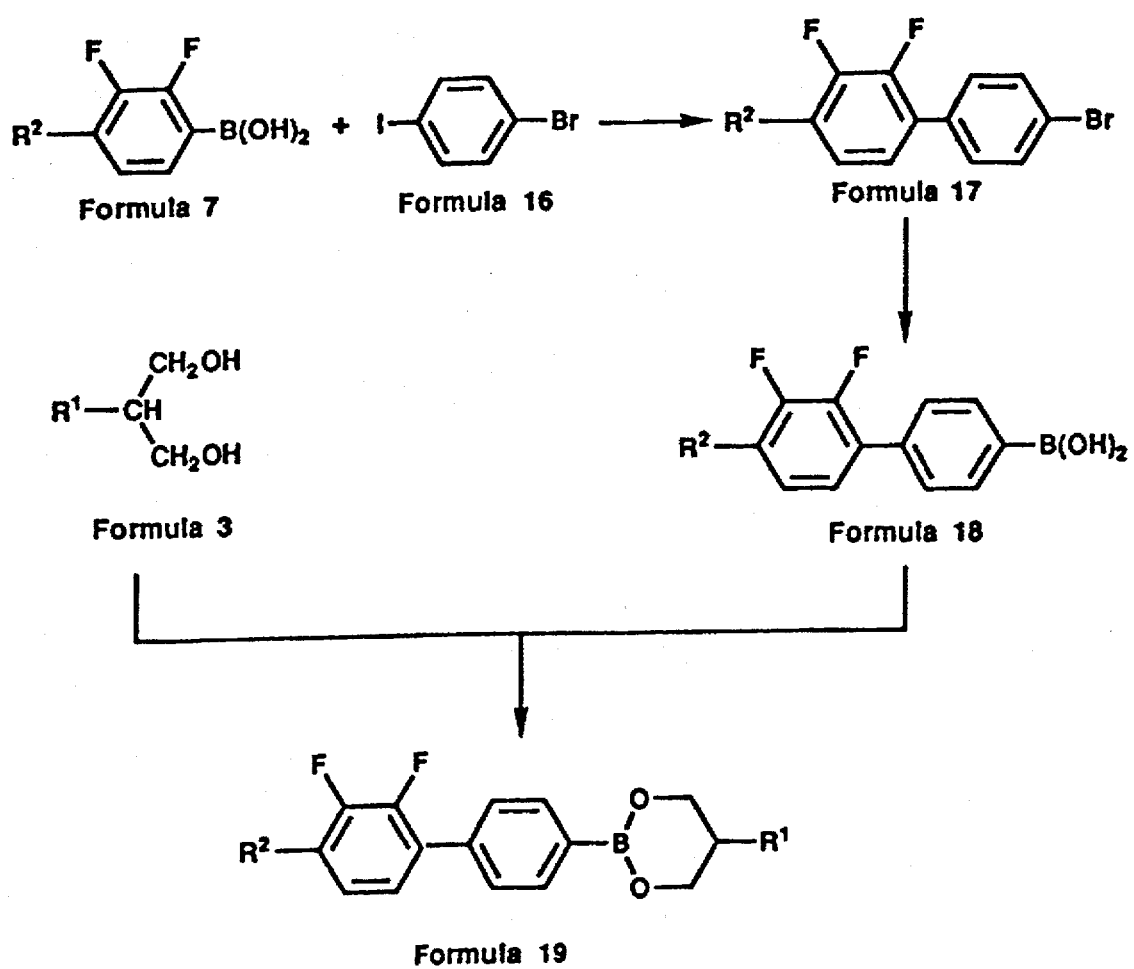
FIG. 3 is another illustration of a compound production scheme.

These compounds are produced according to the scheme illustrated in FIG. 3. In this scheme, the compound of formula 7 (see FIG. 1) is reacted with 4-bromoiodobenzene and tetrakis (triphenylphosphine) palladium to give the product of formula 17 which, on reaction with n-butyllithium under nitrogen at −78° C. and then with triisopropyl borate yields the compound of formula 18. Finally, reaction of this with the 2-substituted-1,3-propandiol of formula 3 and 4-toluene sulphonic acid in dry toluene gives the required product of formula 19.

Compounds of the formula 24

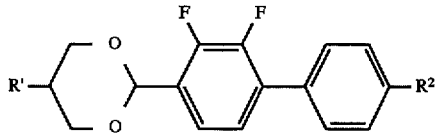

wherein, in the general formula A,

X is CH;

$Y^2$, $Y^3$ are each $(CH_2)_p$, where p is 0;

m is 1;

$Z_1$ is H and $Z_2$ is F.

Figure 4:
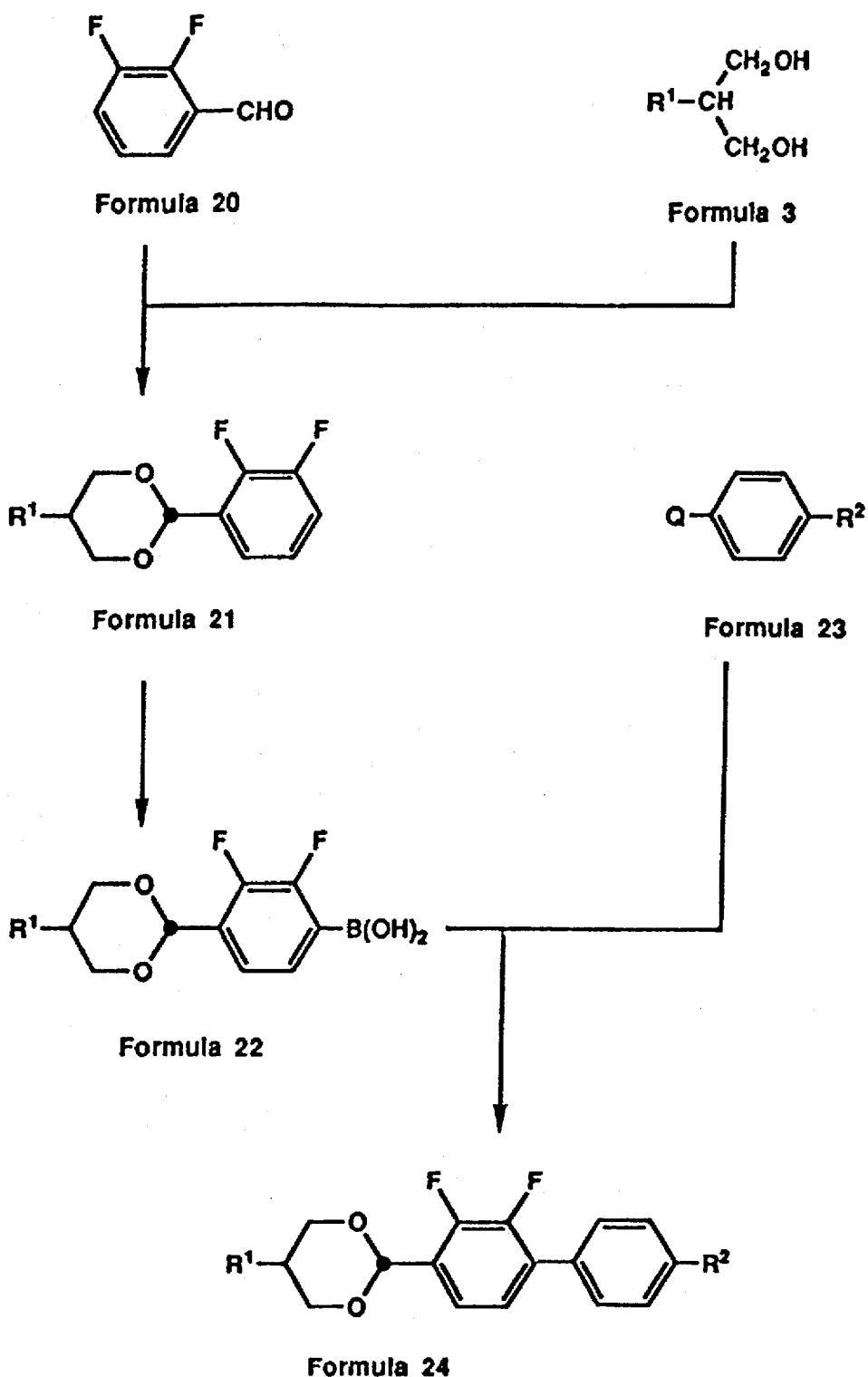
FIG. 4 is another illustration of a compound production scheme.

These compounds are produced according to the scheme illustrated in FIG. 4. In this scheme, the compound of formula 3 (see FIG. 1) is reacted with 2,3-difluorobenzaldehyde (formula 20) and 4-toluene sulphonic acid in dry benzene to give the compound of formula 21 which, when reacted first with n-butyllithium in tetrahydrofuran under nitrogen at −78° C. and then with trisopropylborate in the same solvent and under the same conditions followed by warming and treatment with hydrochloric acid yields the compound of formula 22. Reaction of this with the compound of formula 23 wherein Q is bromine or iodine with tetrakis(triphenylphosphine) palladium gives the required compound of formula 24.

Compounds of formula 25

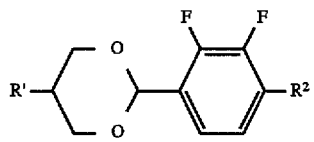

i.e. wherein, in general formula A,

X is CH;

$Y^3$ is $(CH_2)_p$ and p is 0;

m is 0;

and $Y^4$ is a covalent bond.

Reaction of the compound of formula 21 (see FIG. 4) with n-butyllithium in tetrahydrofuran under nitrogen at −78° C. with a solution of the iodo compound of formula $R^2I$ in tetrahydrofuran gives the required compound of formula 25.

Compounds of formula 27

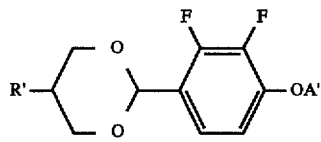

Figure 5:
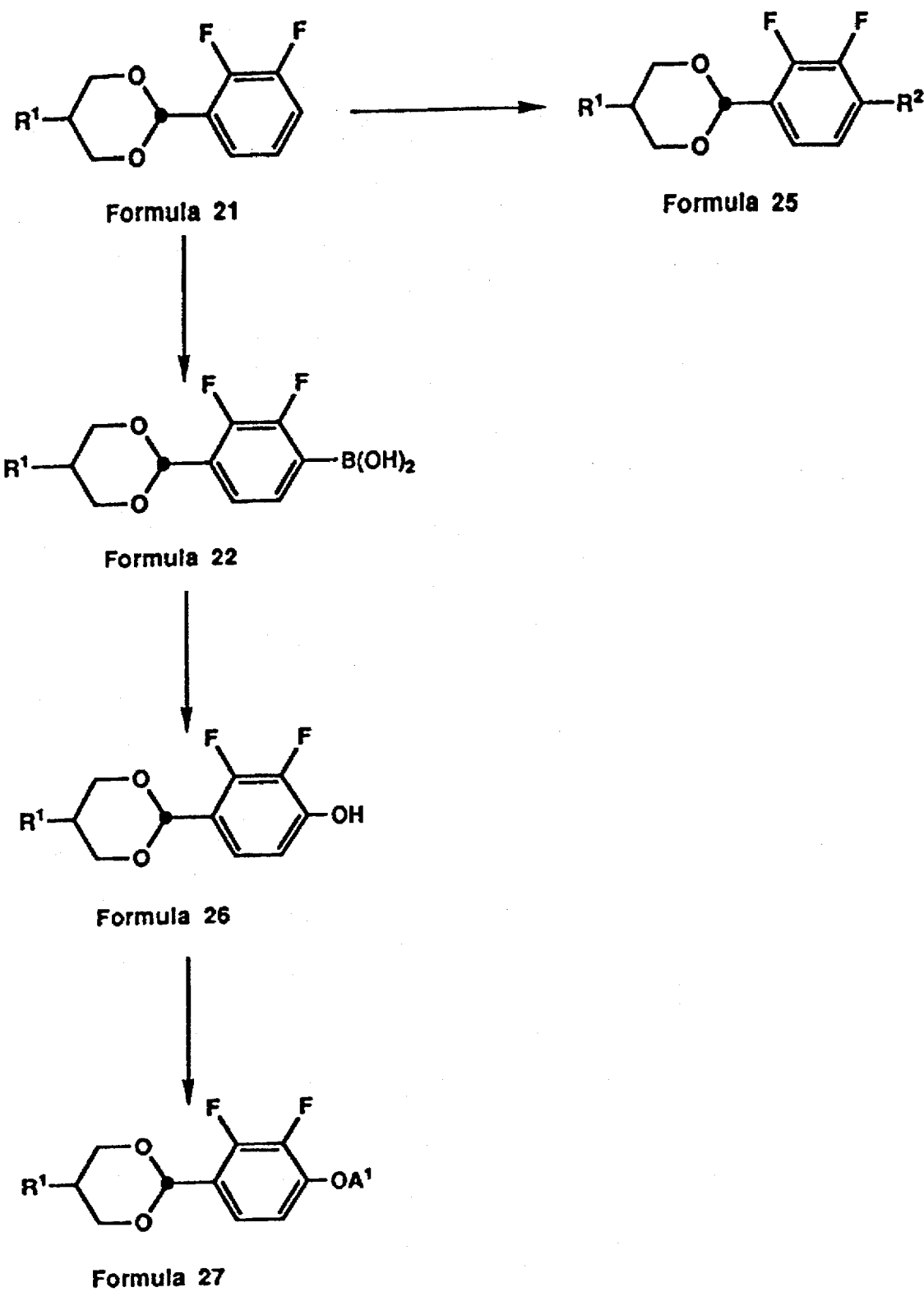

To obtain the compounds of formula 27, the compound of formula 22 (see FIGS. 4 and 5) is reacted first with hydrogen peroxide in ether and sodium carbonate to give the compound of formula 26 which is then reacted with a bromo compound $A^1Br$ to give the required compound of formula 27.

Compounds of Formula 31

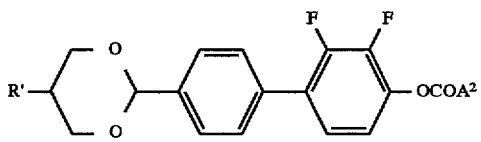

i.e. wherein, in general formula A:

X is CH $Y^2$, $Y^3$ are each $(CH_2)_p$ and p is 0;

m is 1;

$Z_1$ is F and $Z_2$ is H

Figure 6:
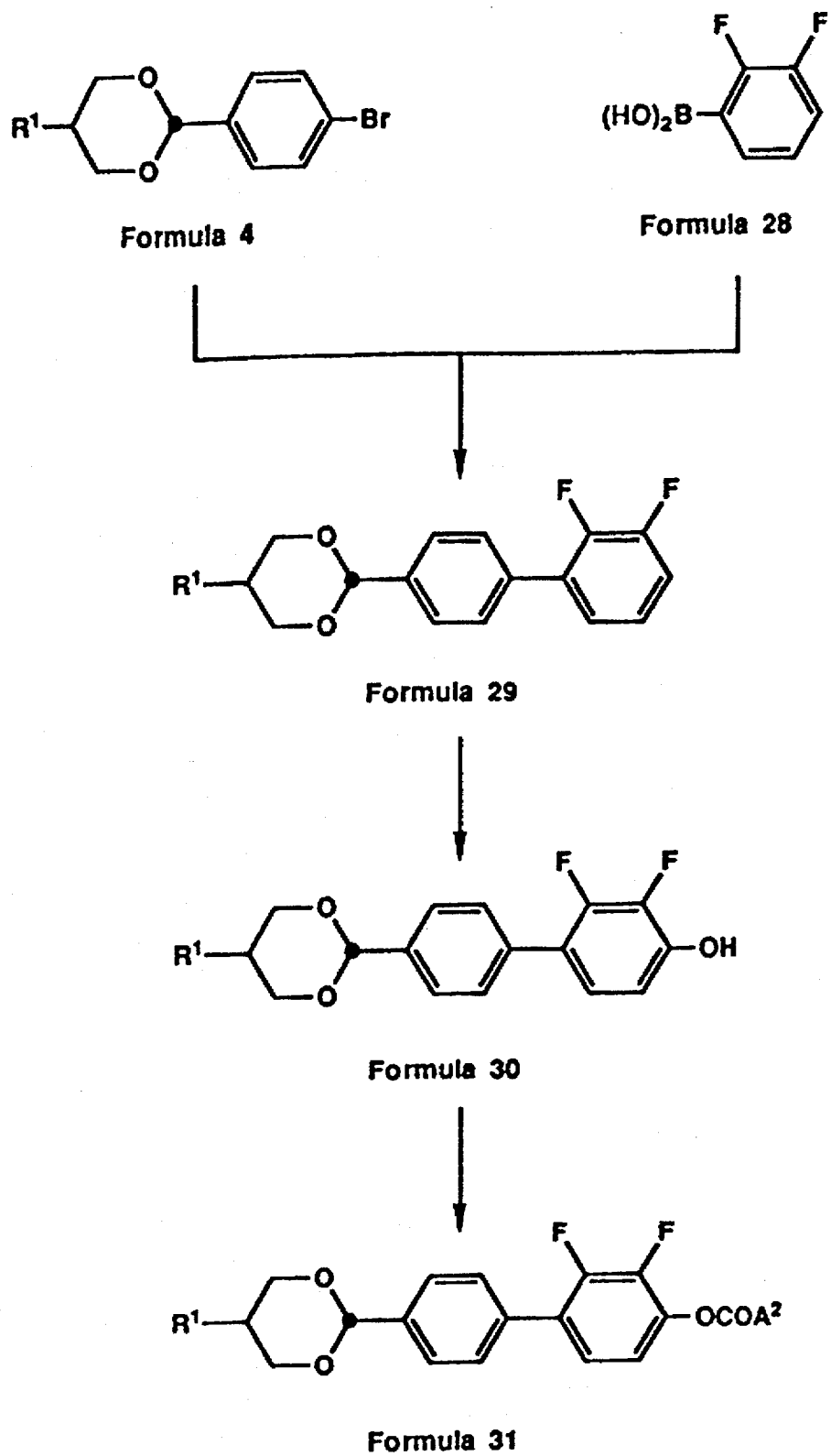
Figure 8:
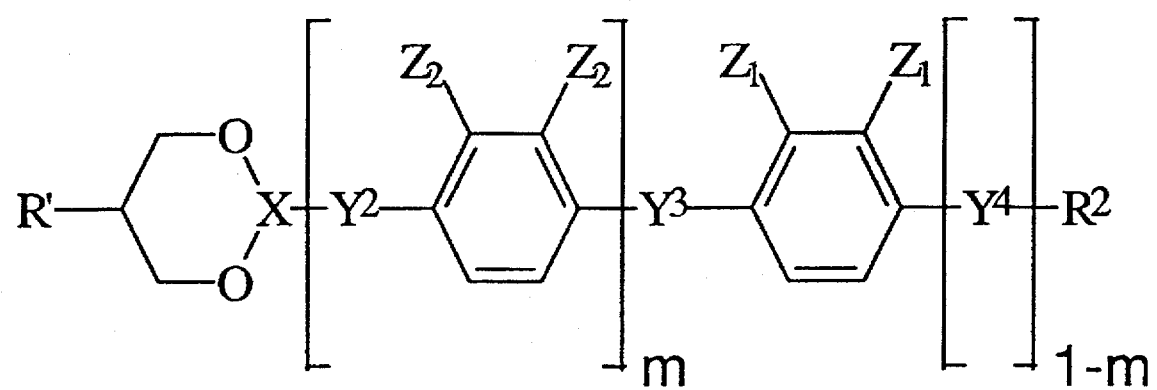

Reaction of compound of formula 4 with 2,3-difluorophenylboronic acid and with tetrakis-(triphenylphosphine) palladium yields the compound of formula 29 (see FIG. 6) which, on reaction with n-butyllithium and triisopropyl borate followed by hydrogen peroxide gives the compound of formula 30. The required compound of formula 31 is obtained by reaction of the compound of formula 30 with an acid of formula $A^2COOH$ in the presence of N,N'-dicyclohexylcarbodiimide and 4-dimethylaminopyridine.

Compounds of formula 33

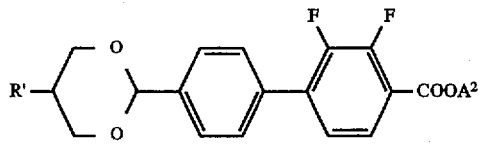

i.e. wherein in general formula A:

X is CH $Y^2$, $Y^3$ are each $(CH_2)_p$ and p is 0;

m is 1;

$Z_1$ is F and $Z_2$ is H.

As illustrated in FIG. 7, the compound of formula 29 (see FIG. 6) is reacted with n-butyllithium and then poured onto carbon dioxide granules to give the benzoic acid of formula 32. Reaction of this compound with $A^2OH$ in the presence of N,N'-dicyclohexylcarbodiimide and 4-dimethylaminopyridine gives the required compound of formula 33.

Compositions comprising one or more of the compounds of this invention for use in LCDs have been prepared and incorporated in cells for use in LCD devices and have demonstrated the following properties, either alone or in a mixture with other suitable liquid cry compounds.

(a) Temperature Range of Smectic C Phase

| Compound | Range (°) |
|---|---|
| A | 66–98 |
| B | 61–98 |
| C | 54–122 |
| D | 43–110 |
| E/F (1:1 mixture) | 20–67 |
| G/F (1:4 mixture) | 20–82 |
| H | 56–104 |

(b) Other Properties

A blend of equal proportions by weight of each of the following compounds of formula 12 was prepared:

| $R^1$ | $A^1$ |
|---|---|
| $C_5H_{11}$ | $C_7H_{15}$ |
| $C_5H_{11}$ | $C_8H_{17}$ |
| $C_5H_{11}$ | $C_9H_{19}$ |
| $C_7H_{15}$ | $C_5H_{11}$ |
| $C_7H_{15}$ | $C_7H_{15}$ |
| $C_9H_{19}$ | $C_7H_{15}$ |
| $C_9H_{19}$ | $C_9H_{19}$ | and four parts of this blend were mixed with one part of the compound of formula 11 where $R^1$ is $C_9H_{19}$ and $A^1$ is $C_5H_{11}$ to give Mixture 1. Mixture 1 had an Smectic C phase range from 20° C. to 97° C.

Mixture 1 was then used as an Sc host with a chiral dopant to give the following mixture 2:

Mixture 1 90% by weight
chiral S-(−)-1-cyano-2-methylpropyl-4¹-nonoxybiphenyl-4-carboxylate- 1.5% by weight racemic (±)-S-(−)-1-cyano-2-methylpropyl-4¹-nonoxybiphenyl-4-carboxylate- 8.5% by weight (see Chan et al, Mol. Cryst. Liq. Cryst. 172, 125 (1989).

Mixture 2 had a Smectic C phase range from −20° C. to 93° C.

(i) Spontaneous polarisation

Figure 9:
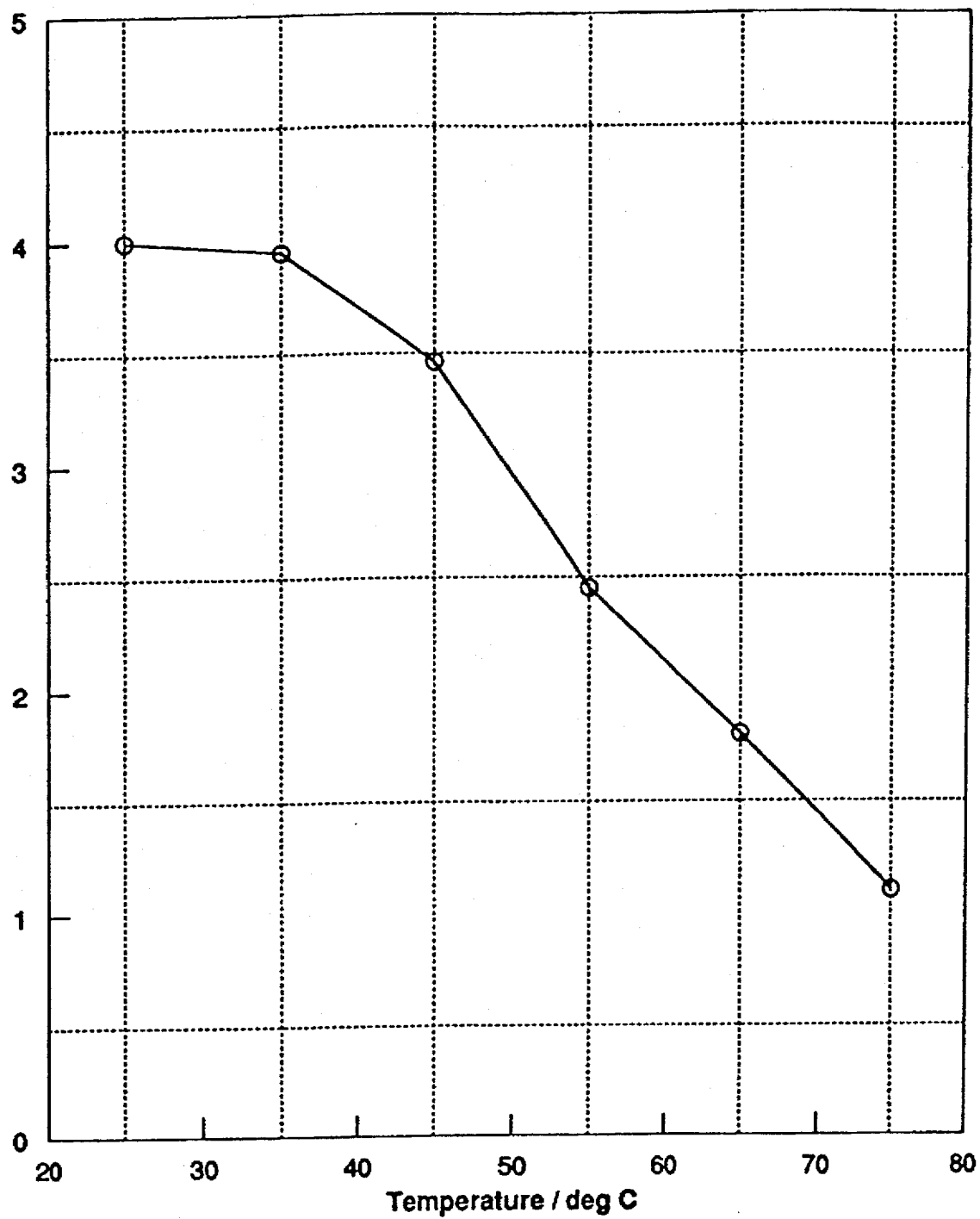

FIG. 9 shows the variation of spontaneous polarisation of mixture 2 with temperature. The data was obtained using a 6 μm thick cell at 50 Hz and 30 volts employing a Diamant bridge (see Rev. Sci. Instr., 28, 30 (1957)).

(ii) Tilt Angle Measurements

Figure 10:
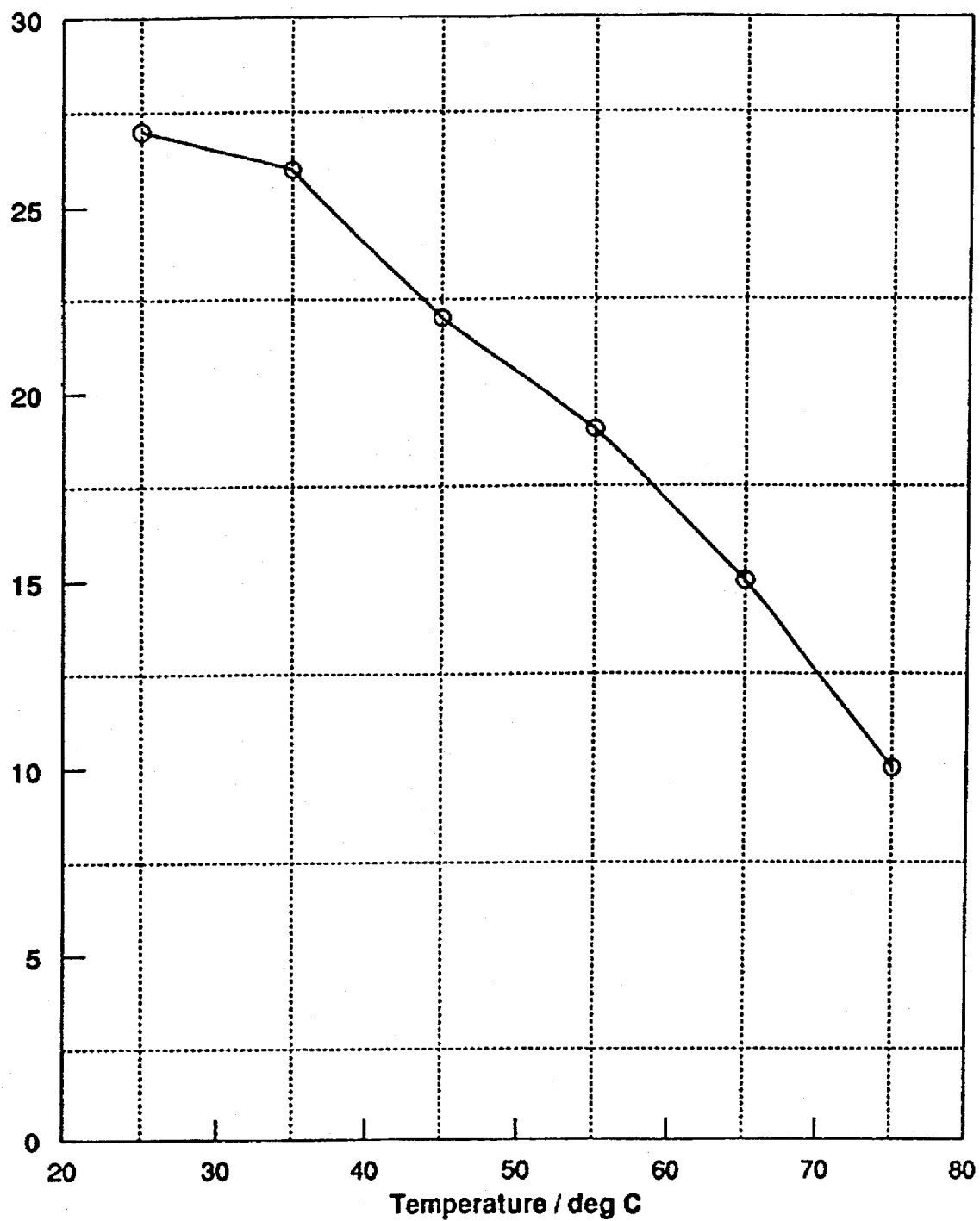

FIG. 10 shows the variation of tilt angle, θ, with respect to temperature for mixture 2. The tilt angle was measured by applying a square wave of 50 Hz at 30 volts to a filled 6 μm cell and the maximum and minimum transmission positions, obtained by rotating the sample, were measured using a photomultiplier, the difference between the two values being the cone angle, 2 θ, of the molecules in the Sc phase.

(iii) Monopolar Response Time

Figure 11:
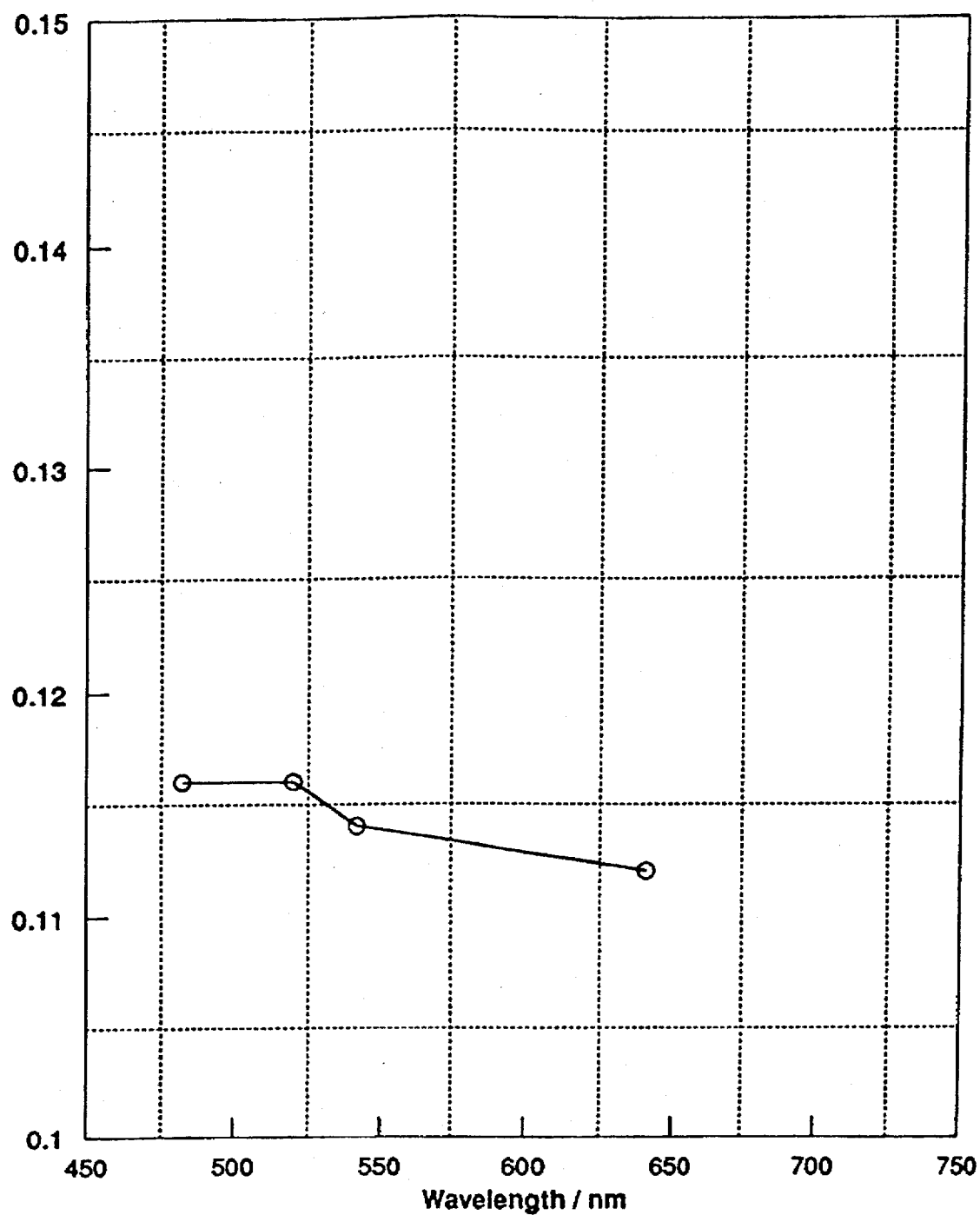

FIG. 11 shows the plot of response time against applied voltage. The data was obtained as described in Ferroelectrics, 122, 63 (1991). A monopolar pulse of 1:100 duty cycle and alternating polarity was used to switch the device alternately between its two optical states. The response time is taken as the minimum pulse width at which visibly clear switching occurs in the cell as observed under a crossed polarising microscope.

(iv) Multiplexing Characteristic

Figure 12:
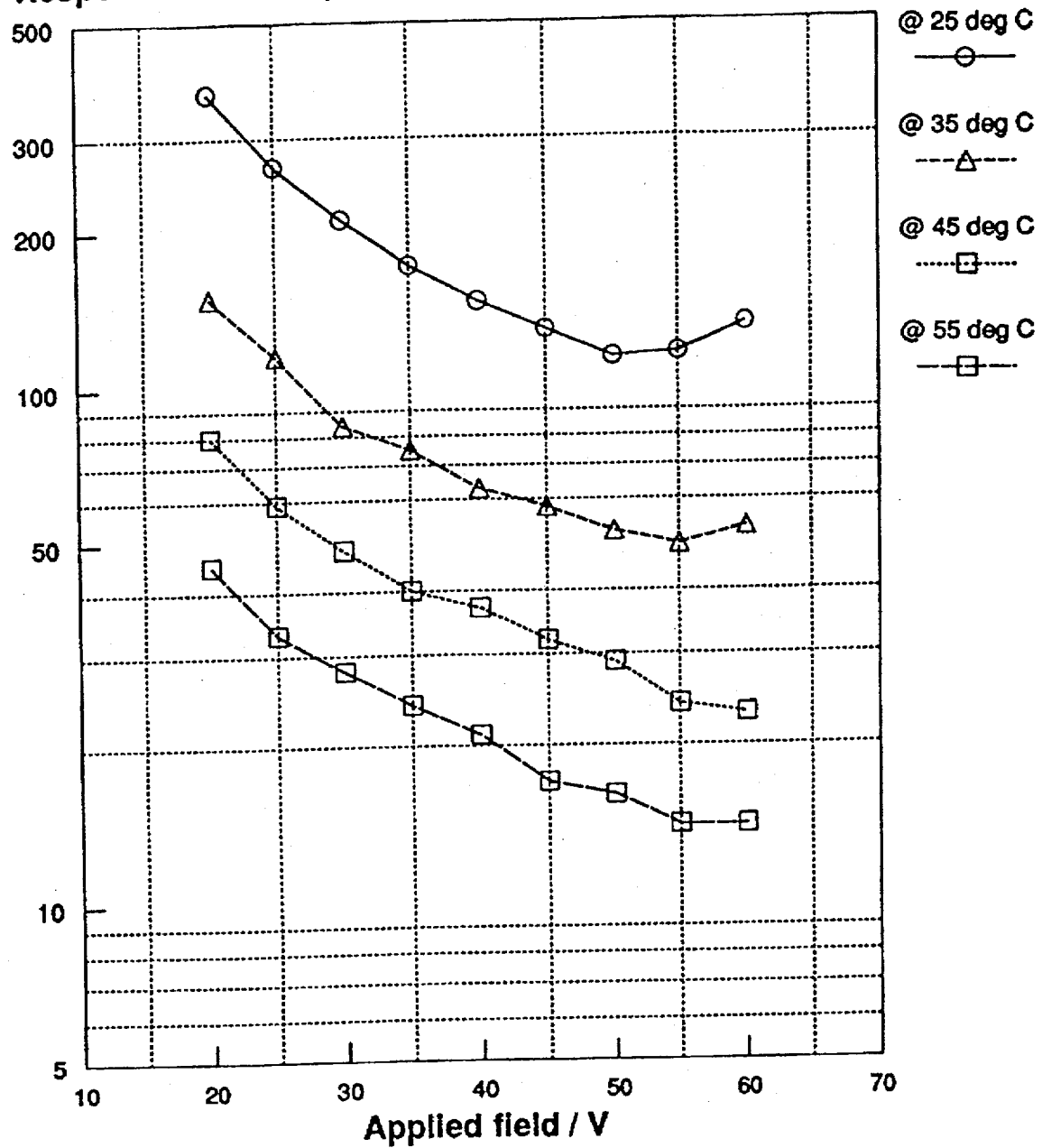

The multiplexing characteristics for mixture 2 under real drive conditions (i.e. with random data voltage patterns) is shown in FIG. 12, using the 2-slot multiplexing scheme as described in Ferroelectrics, 122, 63 (1991).

Mixture 2 exhibits a wide operating temperature range and multiplexes at around 100 μs line address time (l.a.t.) at room temperature down to 10 μs l.a.t. at 65° C.

(v) Birefringence

Figure 13:
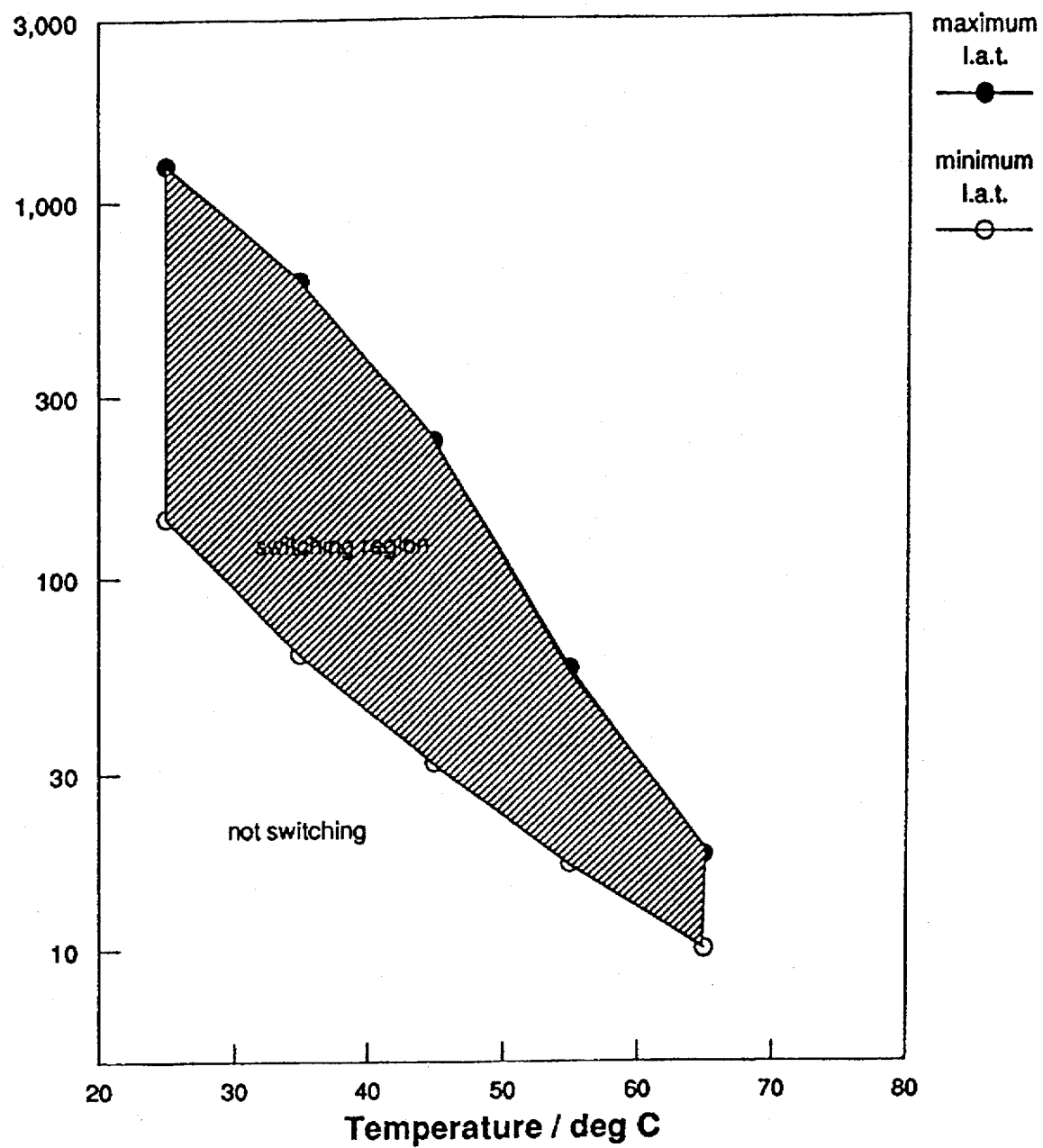

This is illustrated for mixture 2 in FIG. 13. The Senamont compensator technique was used as described in the "Nikon Polarising Microscope Instructions Manual", p. 34 (1990). Publisher: Nikon Inc., Instrument Group, 623 Stewart Avenue, Garden City, N.Y. 11530, U.S.A. As shown in FIG. 13, mixture 2 exhibited a very low birefringence of _0.12. This value is of the same order as the values obtained using previously disclosed two ring liquid crystal systems such as the phenylpyrimidines and the biphenyls.

The liquid crystal cell comprising mixture 2, used to obtain the data illustrated in and described with reference to FIGS. 9 to 13, may also be used in an electro-optical display device. The cell consists of two glass plates, arranged parallel. On the inner surface of each plate is a thin film of a transparent conducting material, e.g. indium tin oxide (ITO), coated with a transparent layer of a polymer such as Nylon 6 to protect the conducting material and to aid surface alignment of a layer of Sc* liquid crystal material sandwiched between the coated plates. The space between the Nylon 6 layers defines the thickness of the layer of the ferroelectric liquid crystals and its edges are sealed with UV curable glue. For the spontaneous polarisation and tilt angle measurements as shown in FIGS. 9 and 10 respectively, the spacing was 6 μm, and for other experiments as shown in FIGS. 11 and 13, the spacing was 1.5 μm. The cell is normally positioned between crossed polarisers when being used in the birefringence mode referred to above.

The invention is further illustrated by the following examples to which the following general points apply:

General Techniques Employed

1. Chromatography Techniques

1.1 Analytical Thin-Layer Chromatography (TLC)

The TLC plates used were aluminium sheets coated with fluorescence silica gel 60 F254 (Merck 5554, Darmstadt). The detection of spots was achieved by UV fluorescence (254 nm) and/or by contact with iodine vapour.

1.2 Column Chromatography

Column chromatographic separations were carried out using either flash column chromatography over silica gel C60-H (May & Baker, 40–60 mm) or standard gravity column chromatography over silica gel (Fisons, 60–120 mesh).

1.3 Gas-Liquid Chromatography (GLC)

The progress of many reactions and the purity of a number of products was checked using a Perkin-Elmer 8320 capillary gas chromatograph equipped with a BP1 capillary column.

1.4 High Performance Liquid Chromatography (HPLC)

The purity of all final compounds and a number of intermediates was checked by HPLC. The system consisted of the following modules:

(i) a Kontron 420 Pump;

(ii) a Must Multi-port Stream Switch;

(iii) a Perkin-Elmer ISS-100 Auto Sampler;

(iv) a Dynamax Microsorb C18 Reverse Phase Column (25 cm);

(v) a Spectroflow 757 Absorbance Detector;

(vi) a Chessell Chart Recorder (BD 40 04);

(vii) a Perkin-Elmer 3600 Data Station.

Some products were purified by preparative HPLC. The system consisted of the following modules:

(i) a Kontron 420 Pump (for eluent);

(a Gilson 303 Pump (for injection);

(iii) a Gilson 201–202 Controller;

(iv) a Gilson Holochrome UV Detector;

(v) a Chessell Chart Recorder (BD 40 04);

(vi) Gilson 201 Fraction Collector.

The solvent system used was methanol unless otherwise stated.

2 Assessment of Materials

2.1 Spectroscopy (a) Infra-Red (IR) Spectroscopy

IR was carried out using a Perkin-Elmer 783 infra-red spectrophotometer.

(b) Mass Spectrometry (MS)

MS was carried out using a Finnigan-MAT 1020 automated GC/MS.

(c) Nuclear Magnetic Resonance (NMR) Spectroscopy

NMR was carried out using a JEOL JNM-GX270 FT nuclear magnetic resonance spectrometer (270 MHz).

2.2 Transition Temperatures (a) Thermal Optical Microscopy

The transition temperatures of all mesogens were determined using an Olympus BH-2 or a Zeiss Universal polarising light microscope in conjunction with a Mettler FP52 heating stage fitted with a Mettler FP5 control unit. The heating and cooling rate used was 1° min$^{-1}$, except for around clearing transitions where the rate used was 0.2° min$^{-1}$.

(b) Differential Scanning Calorimetry (DSC)

All liquid-crystalline transitions were verified by thermal analysis using a Perkin-Elmer DSC7 differential scanning calorimeter fitted with a TAC 7/PC instrument controller, an IBM PC/2 personal computer and a Perkin-Elmer Controlled Cooling Accessory.

A static nitrogen atmosphere was used in the furnace and the reference material was aluminium oxide ($Al_2O_3$). Indium metal was used as the standard for callibration purpose.

3 Drying and Purification of Solvents (i) Benzene, diethyl ether and toluene were dried over sodium wire.

(ii) Dichloromethane was distilled over phosphorous pentoxide prior to use.

(iii) Tetrahydrofuran was distilled over sodium and benzophenone prior to use.

(iv) Pyridine was dried over anhydrous potassium hydroxide.

(v) Super-dry ethanol was distilled over magnesium turnings and iodine prior to use.

4. Abbreviations (a) In the reporting of proton NMR data, the following abbreviations have been used: s—single, d—doublet, t—triplet, q—quartet, qn—quintet, sex—sextet, m—multiplet.

(b) When describing mesomorphic behaviour or physical properties:

m.p.—melting point, b.p.—boiling point, K—crystalline solid, Iso—isotropic liquid phase, N—nematic phase, Sm—smectic mesophases.

(c) The solvents used:

DCC—N,N'-dicyclohexylcarbodiimide, DEAD—diethyl azodicarboxylate, DMAP—4-dimethylaminopyridine, DME—dimethoxy ethane. DMF—dimethyl formamide, THF—tetrahydrofuran, TsOH—p-toluenesulfonic acid monohydrate.

5 Nomenclature

The IUPAC system of nomenclature has been used throughout.

EXAMPLE 1

Diethyl(2-n-pentylpropanedicarboxylate) (Formula 2)

Alcoholic sodium ethoxide, prepared from sodium (7.8 g, 0.34 mol) in super-dry ethanol (200 cm$^3$) was cooled to ca. 50° C. and diethyl malonate (55 g, 0.34 mol) added slowly with vigorous stirring. 1-Bromopentane (49.5 g, 0.33 mol) was added gradually and the mixture refluxed until neutral to moist litmus (ca. 2 h). The solvent was removed in vacuo and water (200 cm$^3$) added. The aqueous layer was extracted with diethyl ether (2×100 cm$^3$) and the combined ethereal layers were dried ($Na_2SO_4$). The solvent was removed in vacuo and the pure product isolated by distillation under reduced pressure.

Yield=71 g (78%); b.p.=82°–87° C./0.2 mm Hg; $^1$H NMR (CDCl$_3$): δ0.88 (3H, t), 1.28 (12H, m), 1.88 (2H, q), 3.31 (1H, t), 4.20 (4H, q); IR: 2968, 2935, 2870, 1735, 1468, 1372, 1156, 1120, 1035 cm$^{-1}$; MS: 230 [M]$^+$, 185, 173, 160, 143.

EXAMPLE 2

Diethyl(2-n-hexylpropanedicarboxylate)

Quantities: sodium (8.1 g, 0.35 mol), diethyl malonate (57.5 g, 0.36 mol) and 1-bromohexane (59.5 g, 0.36 mol). The experimental procedure was as described in Example 1.

Yield=72.2 g (84%); b.p.=106°–110° C./0.9 mm Hg; $^1$H NMR (CDCl$_3$): δ0.89 (3H, t), 1.28 (14H, m), 1.89 (2H, q), 3.31 (1H, t), 4.20 (4H, q); IR: 2968, 2940, 2870, 1740, 1470, 1372, 1156, 1120, 1037 cm$^{-1}$; MS: 244 [M]$^+$, 199, 173.

EXAMPLE 3

Diethyl(2-n-heptylpropanedicarboxylate)

Quantities: sodium (11.5 g, 0.5 mol), diethyl malonate (82.9 g, 0.52 mol) and 1-bromoheptane (90 g, 0.5 mol). The experimental procedure was as described in Example 1.

Yield=105 g (82%); b.p.=103°–109° C./0.3 mm Hg; $^1$H NMR (CDCl$_3$): δ0.90 (3H,t), 1.28 (16H, t), 1.89 (2H, q), 3.32 (1H, t), 4.20 (4H, q); IR: 2970, 2940, 2872, 1740, 1470, 1373, 1156, 1123, 1035 cm$^{-1}$; MS: 258 [M]$^+$, 213, 173, 160.

EXAMPLE 4

Diethyl(2-n-octylpropanedicarboxylate)

Quantities: sodium (8.5 g, 0.37 mol), diethyl malonate (60 g, 0.37 mol) and 1-bromooctane (71.5 g, 0.37 mol). The experimental procedure was as described in Example 1.

Yield=79.5 g (79%); b.p.=112°–113° C./0.3 mm Hg; $^1$H NMR (CDCl$_3$): δ0.88 (3H, t), 1.27 (18H, t), 1.88 (2H, q), 3.31 (1H, t), 4.20 (4H, q); IR: 2960, 2930, 2860, 1733, 1470, 1370, 1156, 1120, 1034 cm$^{-1}$; MS: 237, 228 [M-44 (CH$_2$=CHOH)]$^+$, 173, 160.

EXAMPLE 5

Diethyl(2-n-nonylpropanedicarboxylate)

Quantities: sodium (11.4 g, 0.5 mol), diethylmalonate (80.5 g, 0.5 mol) and 1-bromononane (102 g, 0.49 mol). The experimental procedure was as described in Example 1.

Yield=114 g (81%); b.p.=130°–138° C./1.3 mm Hg; $^1$H NMR (CDCl3): δ0.90 (3H, t), 1.30 (20H, m), 1.90 (2H, q), 3.32 (1H, t), 4.20 (4H, q); IR: 2965, 2935, 2865, 1740, 1472, 1374, 1156, 1035 cm$^{-1}$; MS: 287 [M+1]$^+$, 241, 173, 160.

EXAMPLE 6

2-n-Pentylpropan-1,3-diol (Formula 3)

A solution of compound from Example 1 (59.2 g, 257 mmol) in sodium-dried diethyl ether (50 cm3) was added dropwise to a mixture of lithium aluminum hydride (19.5 g, 514 mmol) in dry diehtyl ether (450 cm$^3$) with vigorous stirring and heated under gentle reflux. During this period, four 50 cm$^3$ portions of dry diethyl ether were added. After further heating (1 h), water (75 cm$^3$) was carefully added to decompose excess lithium aluminum hydride, followed by sulphuric acid (20%, 350 cm$^3$). The aqueous layer was extracted with diethyl ether (2×100 cm$^3$), the combined ethereal layers washed with water (2×100 cm$^3$) and dried (MgSO$_4$). The solvent was removed in vacuo to give the product as a colourless oil.

Yield=31 g (83%); $^1$H NMR (CDCl$_3$): δ0.90 (3H, t), 1.30 (8H, m), 1.77 (1H, m), 2.74 (2H, s), 3.64 (2H, q), 3.82 (2H, q); IR: 3700–3040, 2962, 2930, 2866, 1470, 1035 cm$^{-1}$; MS: 128 [M-H$_2$O]$^+$, 110, 98.

EXAMPLE 7

2-n-Hexylpropan-1,3-diol

Quantities: compound from Example 2 (72.2 g, 0.3 mol) and lithium aluminum hydride (20 g, 0.53 mol). The experimental procedure was as described in Example 6. The pure product isolated by distillation under reduced pressure.

Yield=44 g (92%); b.p.=108°–110° C./0.2 mm Hg; $^1$H NMR (CDCl$_3$): δ0.90 (3H, t), 1.30 (10H, m), 1.77 (1H, m), 2.74 (2H, s), 3.65 (2H, q), 3.82 (2H, q); IR: 3700–3050, 2960, 2932, 2838, 1470, 1032 cm$^{-1}$; MS: 160 [M]$^+$, 124, 112.

EXAMPLE 8

2-n-Heptylpropan-1,3-diol

Quantities: compound from Example 3 (72.2 g, 0.3 mol) and lithium aluminum hydride (20 g, 0.53 mol). The experimental procedure was as described in Example 6. The pure product was recrystallised from light petrol/ethyl acetate; (49:1).

Yield=54.5 g (77%): m.p.=32°–33° C.; $^1$H NMR (CDCl$_3$): δ0.90 (3H, t), 1.30 (12H, m), 1.77 (1H, m), 2.55 (2H, s), 3.67 (2H, q), 3.82 (2H, q); IR: 3700–3050, 2962, 2932, 2864, 1473, 1040 cm$^{-1}$; MS: 138 [M-(H$_2$O)$_2$]$^+$, 126.

EXAMPLE 9

2-n-Octylpropan-1,3-diol

Quantities: compound from Example 4 (76.5 g, 0.28 mol) and lithium aluminum hydride (23 g, 0.6 mol). The experimental procedure was as described in Example 6. The product was obtained as a colourless solid.

Yield=48.3 g (92%); $^1$H NMR (CDCl$_3$): δ0.88 (3H, t), 1.27 (14H, m), 1.78 (1H, m), 2.60 (2H, s), 3.66 (2H, q), 3.83 (2H, q); IR: 3640–3060, 2920, 2850, 1463, 1037 cm$^{-1}$; MS: 188 [M]$^+$, 171, 143.

EXAMPLE 10

2-n-Nonylpropan-1,3 -diol

Quantities: compound from Example 5 (76.5 g, 0.28 mol) and lithium aluminum hydride (23 g, 0.6 mol). The experimental procedure was as described in Example 6.

Yield=79 g (98%); m.p.=50.0°–50.5° C.; $^1$H NMR (CDCl$_3$): δ0.90 (3H, t), 1.30 (16H, m), 1.78 (1H, m), 2.15 (2H, s), 3.67 (2H, q), 3.83 (2H, q); IR: 3600–3030, 2930, 2864, 1473, 1383, 1040 cm$^{-1}$; MS: 203 [M+1]$^+$, 202 [M]$^+$.

EXAMPLE 11

2-(4'-Bromophenyl)-5-n-pentyl-1,3-dioxane (Formula 4)

A mixture of compound from Example 6 (31 g, 0.21 mol), 4-bromobenzaldehyde (38.8 g, 0.21 mol) and 4-toluenesulphonic acid (110 mg) in dry toluene (200 cm$^3$) was heated under reflux (3 h) using a Dean and Stark apparatus. On cooling to room temperature the mixture was poured into aqueous sodium hydrogen carbonate solution (5%, 70 cm$^3$) and the separated organic layer washed with aqueous sodium hydrogen carbonate solution (5%, 2×60 cm$^3$), water (2×60 cm$^3$) and dried (MgSO$_4$). The solvent was removed in vacuo and the residue purified by crystalliation from methanol to remove the cis-isomer.

Yield=33.1 g (50%); m.p.=76.5°–77.0° C.; $^1$H NMR (CDCl$_3$): δ0.89 (3H, t), 1.09 (2H, q), 1.29 (6H, m), 2.11 (1H, m), 3.52 (2H, t), 4.22 (2H, q), 5.36 (1H, s), 7.35 (2H, m), 7.49 (2H, m); IR: 2964, 2936, 2868, 1600, 1490, 1470, 1387, 1168, 1132, 1088, 1073, 1026, 1014, 982, 805 cm$^{-1}$; MS: 314 [M]$^+$, 312 [M]$^+$, 185, 183, 157, 155.

EXAMPLE 12

2-(4'-Bromophenyl)-5-n-hexyl-1,3-dioxane

Quantities: compound from Example 7 (44 g, 0.27 mol), 4-bromobenzaldehyde (49 g, 0.27 mol) and 4-toluenesulphonic acid (150 mg). The experimental procedure was as described in Example 11.

Yield=43.3 g (49%); m.p.=58.0°–58.5° C.; $^1$H NMR (CDCl$_3$): δ0.88 (3H, t), 1.09 (2H, q), 1.28 (8H, m), 2.11 (1H, m), 3.52 (2H, t), 4.22 (2H, q), 5.36 (1H, s), 7.36 (2H, m), , 7.49 (2H, m); IR: 2964, 2922, 2852, 1597, 1490, 1468, 1410, 1384, 1168, 1132, 1083, 1010, 813 cm$^{-1}$; MS: 328 [M]$^+$, 326 [M]$^+$, 185, 183, 157, 155.

EXAMPLE 13

2-(4'-Bromophenyl)-5-n-heptyl-1,3-dioxane

Quantities: compound from Example 8 (44 g, 0.25 mol), 4-bromobenzaldehyde (42.8 g, 0.23 mol) and 4-toluenesulphonic acid (150 mg). The experimental procedure was as described in Example 11.

Yield=38.8 g (49%); m.p.=59.0°–59.5° C.; $^1$H NMR (CDCl$_3$): δ0.90 (3H, t), 1.09 (2H, q) 1.30 (10H, m), 2.12 (1H, m), 3.52 (2H, t), 4.23 (2H, q), 5.38 (1H, s), 7.30 (2H, s), 7.30 (2H, m), 7.49 (2H, m); IR: 2962, 2934, 2864, 1600, 1492, 1474, 1389, 1168, 1132, 1087, 1030, 1010, 808 cm$^{-1}$; MS: 342 [M]$^+$, 340 [M]$^+$, 185, 183.

EXAMPLE 14

2-(4'-Bromophenyl)-5-n-octyl-1,3-dioxane

Quantities: compound from Example 9 (48.3 g, 0.26 mol), 4-bromobenzaldehyde (46.5 g, 0.25 mol) and 4-toluenesulphonic acid (150 mg). The experimental procedure was as described in Example 11.

Yield=57 g (64%); m.p.=50.5°–51.0° C.; $^1$H NMR (CDCl$_3$): δ0.89 (3H, t), 1.09 (2H, q), 1.27 (12H, m), 2.12 (1H, m), 3.51 (2H, t), 4.22 (2H, q), 5.36 (1H, s), 7.36 (2H, m), 7.49 (2H, m); IR: 2958, 2922, 2854, 1600, 1468, 1418, 1387, 1150, 1127, 1081, 1013, 822 cm$^{-1}$; MS: 356 [M]$^+$, 354 [M]$^{3O}$, 185, 183.

EXAMPLE 15

2-(4'-Bromophenyl)-5-n-nonyl-1,3-dioxane

Quantities: compound from Example 10 (40.5 g, 0.2 mol), 4-bromobenzaldehyde (37 g, 0.2 mol) and 4-toluenesulphonic acid (150 mg). The experimental procedure was as described in Example 11.

Yield=33 g (45%); m.p.=53.0°–54.0° C.; $^1$H NMR (CDCl$_3$): δ0.90 (3H, t), 1.10 (2H, q) 1.30 (14H, m), 2.10 (1H, m), 3.52 (2H, m), 4.23 (2H, m), 5.36 (1H, s), 7.36 (2H, m), 7.50 (2H, m); IR: 2962, 2930, 2860, 1602, 1500, 1468, 1407, 1388, 1172, 1133, 1089, 1016, 812 cm$^{-1}$; MS: 370 [M]$^+$, 368 [M]$^+$, 185, 183.

EXAMPLE 16

1-(2,3 -Difluorophenyl)pentan-1-ol n-Butyllithium (50 cm$^3$, 10.0M in hexanes, 0.5 mol) was added dropwise to a stirred, cooled (−78° C.) solution of 1,2-difluorobenzene (57 g, 0.5 mol) in dry THF (600 cm$^3$) under an atmosphere of dry nitrogen. The mixture was maintained under these conditions (3 h) then a solution of pentanal (43.1 g, 0.5 mol), in dry THF (50 cm$^3$) added dropwise at −78° C. The temperature of the reaction mixture was allowed to reach room temperature overnight. An aqueous solution of ammonium chloride (27 g in 160 cm$^3$ water) was added and the product extracted into diethyl ether (2×150 cm$^3$), the combined extracts washed with water (2×150 cm$^3$) and dried (MgSO$_4$). The solvent was removed in vacuo to give the product as a colourless oil which was purified by distillation under reduced pressure.

Yield=55.5 g (55%); b.p.=94°–98° C./1.0 mm Hg; $^1$H NMR (CDCl$_3$): δ0.90 (3H, t), 1.35 (4H, m), 1.77 (2H, m), 1.92 (1H, s), 5.03 (1H, t), 7.07 (2H, m), 7.22 (1H, m); IR: 3600–3100, 2964, 2938, 2870, 1631, 1601, 1487, 1278, 1205, 1060, 826, 787, 730 cm$^{-1}$; MS: 200 [M]$^+$, 142.

EXAMPLE 17

(2,3-Difluorophenyl)hexan-1-ol

Quantities: n-butyllithium (31 cm$^3$, 10.0M in hexanes, 0.31 mol), hexanal (31.5 g, 0.31 mol) and 1,2-difluorobenzene (35.5 g, 0.31 mol). The experimental procedure was as described in Example 16.

Yield=52.6 g (79%); b.p.=98°–102° C./0.5 mm Hg; $^1$H NMR (CDCl$_3$): δ0.88 (3H, t), 1.30 (6H, m), 1.77 (2H, q), 1.98 (1H, s), 5.02 (1H, t), 7.07 (2H, m), 7.22 (1H, m); IR: 3600–3100, 2968, 2940, 2872, 1630, 1600, 1487, 1277, 1207, 1060, 923, 826, 790, 730 cm$^{-1}$; MS: 213 [M-1]$^+$, 142.

EXAMPLE 18

1-(2,3-Difluorophenyl)heptan-1-ol

Quantities: n-butyllithium (50 cm$^3$, 10.0M in hexanes, 0.5 mol), heptanal (57 g, 0.5 mol) and 1,2-difluorobenzene (57 g, 0.5 mol). The experimental procedure was as described in Example 16.

Yield=93.2 g (82%); b.p.=100°–104° C./0.2 mm Hg; $^1$H NMR (CDCl$_3$): δ0.90 (3H, t), 1.31 (8H, m), 1.78 (2H, q), 2.08 (1H, s), 5.01 (1H, t), 7.07 (2H, m), 7.21 (1H, m); IR: 3600–3100, 2960, 2932, 2860, 1628, 1600, 1489, 1280, 1205, 1065, 926, 825, 787, 728 cm$^{-1}$; MS: 228 [M]$^+$, 210, 143.

EXAMPLE 19

1 -(2,3-Difluorophenyl)octan-1-ol

Quantities: n-butyllithium (30 cm$^3$, 10.0M in hexanes, 0.3 mol), octanal (38.5 g, 0.3 mol) and 1,2-difluorobenzene (34.5 g, 0.3 mol). The experimental procedure was as described in Example 16.

Yield=53.3 g (73%); b.p.=108°–110° C./0.15 mm Hg; $^1$H NMR (CDCl$_3$): δ0.87 (3H, t), 0–1.27 (10H, m), 1.77 (2H. 18q), 1.87 (1H, s), 5.03 (1H, t), 7.07 (2H, m), 7.22 (1H, m); IR: 3600–3100, 2964, 2938, 2864, 1630, 1602, 1490, 1280, 1208, 1067, 827, 790, 730 cm$^{-1}$; MS: 242 [M]$^+$, 224, 142.

EXAMPLE 20

1-(2,3-Difluorophenyl)nonan-1-ol

Quantities: n-butyllithium (50 cm$^3$, 10.0M in hexanes, 0.5 mol), nonanal (71 g, 0.5 mol) and 1,2-difluorobenzene (57 g, 0.5 mol). The experimental procedure was as described in Example 16.

Yield=86.7 g (68%); b.p.=128°–130° C./0.6 mm Hg; $^1$H NMR (CDCl$_3$): δ0.90 (3H, t); 1.30 (12H, m), 1.76 (2H, q), 1.98 (1H, s), 5.02 (1H, t), 7.06 (2H, m), 7.25 (1H, m); IR: 3600–3100, 2930, 2860, 1630, 1600, 1487, 1275, 1205, 1063, 825, 790, 727 cm$^{-1}$; MS: 256 [M]$^+$, 238, 143.

EXAMPLE 21

(2,3-Difluorophenyl)decan-1-ol

Quantities: n-butyllithium (30 cm$^3$, 10.0M in hexanes, 0.3 mol), decanal (47 g, 0.3 mol) and 1,2-difluorobenzene (34.5 g, 0.3 mol). The experimental procedure was as described in Example 16.

Yield=56.4 g (70%); b.p.=118°–123° C./0.15 mm Hg; $^1$H NMR (CDCl$_3$): δ0.88 (3H, t), 1.27 (14H, m), 1.77 (2H, q), 1.87 (1H, s), 5.03 (1H, t), 7.06 (2H, m), 7.22 (1H, m); IR: 3600–3100, 2934, 2864, 1632, 1602, 1488, 1280, 1207, 1065, 827, 790, 730 cm$^{-1}$; MS: 270 [M]$^+$, 252, 142.

EXAMPLE 22

2,3-Difluoro-1-pentylbenzene

A solution of compound from Example 16 (55.5 g, 0.28 mol) in light petrol (100 cm$^3$) was added dropwise to a stirred mixture of phosphorus pentoxide (127 g, 0.9 mol) in light petrol (300 cm$^3$). The mixture was stirred overnight at room temperature (GLC analysis revealed reaction to be complete) and then filtered. 5% Palladium-on-charcoal (7 g)

was added to the filtrate and the mixture was stirred under an atmosphere of hydrogen (12 h) at room temperature and pressure (GLC analysis revealed reaction to be complete). The palladium-on-charcoal was filtered off and the solvent was removed in vacuo to give the product as a colourless oil which was purified by distillation under reduced pressure.

Yield=29.2 g (57%); b.p.=50°–52° C./0.85 mm Hg; $^1$H NMR (CDCl$_3$): δ0.90 (3H, t), 1.35 (4H, m), 1.62 (2H, q), 2.67 (2H, t), 6.96 (3H, m); IR: 2964, 2938, 2868, 1630, 1600, 1489, 1286, 1210, 1109, 1058, 827, 782, 728 cm$^1$; MS: 184 [M]$^+$, 127.

EXAMPLE 23

2,3-Difluoro-1-hexylbenzene

Quantities: compound from Example 17 (52.6 g, 0.25 mol), phosphorus pentoxide (105 g, 0.74 mol) and 5% palladium-on-charcoal (5.8 g). The experimental procedure was as described in Example 22.

Yield=27.2 g (56%); b.p.=48°–56° C./0.2 mm Hg; $^1$H NMR (CDCl$_3$): δ0.88 (3H, t), 1.31 (6H, m), 1.60 (2H, q), 2.66 (2H, sex), 6.96 (3H, m); IR: 2970, 2940, 2870, 1630, 1600, 1490, 1286, 1212, 830, 782, 730 cm$^1$; MS: 198 [M]$^+$, 169, 155, 141, 127.

EXAMPLE 24

2,3-Difluoro-1-heptylbenzene

Quantities: compound from Example 18 (93.2 g, 0.41 mol), phosphorus pentoxide (174 g, 1.2 mol) and 5% palladium-on-charcoal (4.6 g). The experimental procedure was as described in Example 22.

Yield=30.1 g (35%); b.p.=73°–75° C./0.6 mm Hg; $^1$H NMR (CDCl$_3$): δ0.90 (3H, t), 1.33 (8H, m), 1.62 (2H, q), 2.67 (2H, t), 6.97 (3H, m); IR: 3001, 2972, 2902, 1647, 1614, 1509, 1303, 1228, 841, 798, 746 cm$^{-1}$; MS: 212 [M]$^+$, 169, 140, 127.

EXAMPLE 25

2,3-Difluoro-1-octylbenzene

Quantities: compound from Example 19 (53.3 g, 0.22 mol), phosphorus pentoxide (95 g, 0.67 mol) and 5% palladium-on-charcoal (5.5 g). The experimental procedure was as described in Example 22.

Yield=31 g (62%); b.p.=72°–79° C./0.15 mm Hg; $^1$H NMR (CDCl$_3$): δ0.90 (3H, t), 1.30 (10H, m), 1.60 (2H, q), 2.65 (2H, t), 6.96 (3H, m); IR: 2968, 2934, 2864, 1633, 1600, 1488, 1285, 1213, 830, 782, 728 cm$^{-1}$; MS: 226 [M]$^+$, 183, 169, 155, 141, 128.

EXAMPLE 26

2,3-Difluoro-1-nonylbenzene

Quantities: compound from Example 20 (84.6 g, 0.33 mol), phosphorus pentoxide (142 g, 1mol) and 5% palladium-on-charcoal (7 g). The experimental procedure was as described in Example 22.

Yield=59.1 g (75%); b.p.=100°–105° C./0.4 mm Hg; $^1$H NMR (CDCl$_3$): δ0.88 (3H, t), 1.26 (12H, m), 1.60 (2H, q), 2.65 (2H, sex), 6.95 (3H, m); IR: 2972, 2942, 2872, 1636, 1605, 1495, 1288, 1217, 830, 785, 733 cm$^1$; MS: 240 [M]$^+$, 128.

EXAMPLE 27

2,3-Difluoro-1-decylbenzene

Quantities: compound from Example 21 (56.4 g, 0.21 mol), phosphorus pentoxide (74.5 g, 0.53 mol) and 5% palladium-on-charcoal (4.58). The experimental procedure was as described in Example 22.

Yield=26.6 g (50%); b.p.=105°–112° C./0.6 mm Hg; $^1$H NMR (CDCl$_3$): δ0.88 (3H, t), 1.26 (14H, m), 1.60 (2H, q), 2.65 (2H, sex), 6.96 (3H, m); IR: 2966, 2930, 2864, 1630, 1600, 1490, 1287, 1213, 830, 782, 730 cm$^{-1}$; MS: 254 [M]$^+$, 218, 199, 168, 140, 128, 126.

EXAMPLE 28

4-n-Pentyl-2,3-difluorophenyl boronic acid n-Butyllithium (10 cm$^3$, 10M in hexanes, 0.1 mol) was added dropwise to a stirred, cooled (−78° C.) solution of the compound from Example 22 (17.3 g, 94 m mol) in dry THF (250 cm$^3$) under an atmosphere of dry nitrogen. The reaction mixture was stirred (2.5 h) then a previously cooled (−78° C.) solution of triisopropyl borate (35.7 g, 0.19 mol) in dry THF (70 cm$^3$) added dropwise at −78° C. The reaction mixture was allowed to warm to room temperature overnight then stirred (1h) with hydrochloric acid (10%, 100 cm$^3$). The product was extracted into diethyl ether (2×100 cm$^3$), and the combined extracts washed with water and dried (MgSO$_4$). The solvent was removed in vacuo to yield colourless crystals.

Yield=21 g (98%); $^1$H NMR (CDCl$_3$): δ0.90 (3H, t), 1.33 (4H, m), 1.62 (2H, q), 2.68 (2H, t), 4.97 (2H, band), 7.00 (1H, m), 7.46 (1H, m); IR: 3600–3000, 2962, 2940, 2870, 1636, 1497, 1455, 1355, 1220, 1133, 1056, 996, 905, 815 cm$^{-1}$; MS: 630 [M]$^+$(trimer), 574, 505, 448, 391, 378, 322, 228 [M]$^+$(monomer).

EXAMPLE 29

4-n-Hexyl-2,3-difluorophenyl boronic acid

Quantities: compound from Example 23 (27.78, 0.14 mol), n-butyllithium (14 cm$^3$, 10.0M in hexanes, 0.14 mol) and triisopropyl borate (52.7 g, 0.28 mol). The experimental procedure was as described in Example 28.

Yield=33.8 g (100%); $^1$H NMR (CDCl$_3$): δ0.90 (3H, t), 1.30 (6H, m), 1.62 (2H, q), 2.70 (2H, t), 3.77 (2H, t), 7.00 (1H, m), 7.45 (1H, m); IR: 3700–3000, 2968, 2932, 2860, 1635, 1497, 1455, 1385, 1354, 1220, 1208, 1131, 903, 835 cm$^{-1}$; MS: 242 [M]$^+$, 214, 198, 172.

EXAMPLE 30

4-n-Heptyl-2,3-difluorophenyl boronic acid

Quantities: compound from Example 24 (31.4 g, 0.15 mol), n-butyllithium (15 cm$^3$, 10.0M in hexanes, 0.15 mol) and triisopropyl borate (56.4 g, 0.3 mol). The experimental procedure was as described in Example 28.

Yield=38 g (99%); $^1$H NMR (CDCl$_3$): δ0.90 (3H, m), 1.30 (8H, m), 1.63 (2H, m) 2.67 (2H, t), 4.08 (2H, band), 7.00 (1H, m), 7.45 (1H, m); IR: 3600–3000, 2960, 2930, 2864, 1637, 1455, 1205, 1133, 957, 902 cm$^{-1}$; MS: 256[M]$^+$, 228, 205, 170.

EXAMPLE 31

4-n-Octyl-2,3-difluorophenyl boronic acid

Quantities: compound from Example 25 (31 g, 0.14 mol), n-butyllithium (14 cm$^3$, 10.0M in hexanes, 0.14 mol) and triisopropyl borate (52.7 g, 0.28 mol). The experimental procedure was as described in Example 28.

Yield=37.5 g (99%); 1H NMR (CDCl$_3$): δ0.90 (3H, t), 1.32 (10H, m), 1.63 (2H, q), 2.67 (2H, sex), 5.13 (2H, band), 7.00 (1H, m), 7.46 (1H, m); IR: 3700–3000, 2958, 2920, 2852 1640, 1452, 1223, 1192, 1158, 1020, 955, 901, 832 cm$^{-1}$; MS: 270 [M]+, 242, 226, 172.

EXAMPLE 32

4-n-Nonyl-2,3-difluorophenyl boronic acid

Quantities: compound from Example 26 (35.5 g, 0.15 mol), n-butyllithium (15 cm$^3$, 10M in hexanes, 0.15 mol) and triisopropyl borate (56.4 g, 0.3 mol). The experimental procedure was as described in Example 28.

Yield=42.6 g (100%); $^1$H NMR (CDCl$_3$): δ0.90 (3H, t), 1.27 (12H, m), 1.62 (2H, q), 2.67 (2H, sex), 4.05 (2H, band), 7.00 (1H, m), 7.46 (1H, m); IR: 3700–3000, 2960, 2930, 2858, 1636, 1500, 1456, 1360, 1220, 1200, 905 cm$^{-1}$: MS: 284 [M]$^+$, 240, 127.

EXAMPLE 33

4-n-Decyl-2,3-difluorophenyl boronic acid

Quantities: compound from Example 27 (26.7 g, 105 mmol), n-butyllithium (11 cm$^3$, 10.0M in hexanes, 0.11 mol) and triisopropyl borate (39.5 g, 0.21 mol). The experimental procedure was as described in Example 28.

Yield=31 g (99%); $^1$H NMR (CDCl$_3$): δ0.88 (3H, t), 1.26 (14H, m), 1.61 (2H, q) 2.68 (2H, sex), 4.95 (2H, m), 7.00 (1H, m), 7.45 (1H, m); IR: 3600–3100, 2960, 2920, 2854, 1642, 1452, 1392, 1355, 1225, 1158, 1120, 1023, 954, 901, 830 cm$^{-1}$; MS: 298 [M]$^+$, 254, 171, 127.

EXAMPLE 34

2,3-Difluoro-1-(2'-methyl hexoxy) benzene

In the absence of moisture and under an atmosphere of dry nitrogen, diethyl azodicarboxylate (20.4 g, 0.12 mol) was added dropwise to a stirred solution of triphenylphosphine (31.5 g, 0.12 mol), 2 methyl-hexanol (13.9 g, 0.12 mol) and 2,3-difluorophenol (13 g, 0.1 mol) in dry THF (220 cm$^3$) at room temperature. The reaction mixture was stirred overnight at room temperature until GLC and TLC analysis revealed complete reaction. The solvent was removed in vacuo and diethyl ether (200 cm$^3$) added. The precipitate was filtered out and the solvent removed from the filtrate in vacuo. Flash column chromatography (light petrol/ethyl acetate: 49:1) give the product as a colourless oil.

Yield=22.4 g (98%); $^1$H NMR (CDCl$_3$): δ0.93 (3H, m), 1.04 (3H, d), 1.33 (4H, m), 1.51 (2H, m), 1.97 (1H, sex), 3.79 (1H, q), 3.89 (1H, q), 6.74 (2H, m), 6.95 (1H, m); IR: 2954, 2920, 2866, 1619, 1509, 1479, 1314, 1250, 1170, 762, 704 cm$^{-1}$: MS: 228 [M]$^+$, 129, 56.

EXAMPLE 35

(2-Methylhexoxy)-2,3-difluorophenylboronic acid

Quantities: compound from Example 34 (11.4 g, 50 mmol), n-butyllithium (5 cm$^3$, 10.0M in hexanes, 50 mmol) and triisopropyl borate (18.8 g, 0.1 mol). The experimental procedure was as described in Example 28.

Yield=13.6 g (100%); $^1$H NMR (CDCl$_3$): δ0.92 (3H, sex), 1.04 (3H, d), 1.34 (4H, m), 1.52 (2H, m), 1.98 (1H, sex), 3.83 (1H, q), 3.93 (1H, q), 6.76 (1H, m), 7.46 (1H, m); IR: 3700–3100, 2978, 2880, 1636, 1527, 1477, 1363, 1308, 1233, 1089, 1038, 910, 824 cm$^{-1}$; MS: 468, 286, 130.

EXAMPLE 36

2,3-Difluorophenylboronic acid n-Butyllitium (30 cm$^3$, 10M in hexanes, 0.3 mol) was added dropwise to a stirred, cooled (−78° C.) solution of 1,2-difluorobenzene (34.5 g, 0.3 mol) in dry THF (350 cm$^3$) under a atmosphere of dry nitrogen. The reaction mixture was stirred (2.5 h) then a previously cooled (−78° C.) solution of triisopropyl borate (113 g, 0.6 mol) in dry THF (200 cm$^3$) added dropwise at −78° C. The reaction mixture was allowed to warm to room temperature overnight then stirred (1 h) with hydrochloric acid (10%, 300 cm$^3$). The product was extracted into diethyl ether (2×300 cm$^3$), and the combined extracts washed with water and dried (MgSO$_4$). The solvent was removed in vacuo to yield colourless crystals.

Yield=47 g (100%); $^1$H NMR (CDCl$_3$): δ5.10 (2H, d), 7.16 (1H, m), 7.28 (1H, m), 7.57 (1H, m); IR: 3700–3000, 1628, 1472, 1360, 1270, 1048, 908 cm$^{-1}$; MS: 158 [M]$^+$, 140, 114.

EXAMPLE 37

2,3-Difluorophenol

Hydrogen peroxide (10%, 340 cm$^3$, 1 mol) was added dropwise to a stirred solution of compound from Example 36 (47 g, 0.3 mol) in diethyl ether (350 cm$^3$) heated under reflux. The stirred mixture was heated under reflux for a further 2.5 h then cooled. The ethereal layer was separated and the aqueous layer extracted with diethyl ether (2×200 cm$^3$). The combined ethereal layers were washed with sodium hydroxide (10%, 4×100 cm$^3$) and the separated aqueous layers acidified with 36% hydrochloric acid. The product was extracted into diethyl ether (3×100 cm$^3$), and the combined ethereal extracts washed with water and dried (MgSO$_4$). The solvent was removed in vacuo to give an off white solid.

Yield=39 g (100%); m.p.=30°–32° C.; $^1$H NMR (CDCl$_3$): δ5.15 (1H, d), 6.67–6.82 (2H, m), 6.90–7.00 (1H, m); IR: 3700–3000, 1630, 1535, 1513, 1492, 1482, 1360, 1310, 1255, 1182, 1025, 910, 736 cm$^{-1}$; MS: 130 [M]$^+$, 121.

EXAMPLE 38

2,3-Difluoro-1-n-petoxybenzene

A solution of 1-bromopentane (30.5 g, 0.2 mol) in acetone (50 cm$^3$) was added dropwise to a stirred mixture of compound from Example 37 (26 g, 0.2mol) and potassium carbonate (55.5 g, 0.4 mol) in acetone (200 cm$^3$) at room temperature. The stirred mixture was heated under reflux (43 h) (i.e. until glc analysis revealed a complete reaction), the solution poured into water (600 cm$^3$), and the crude product extracted into diethyl ether (2×200 cm$^3$) and dried (Na$_2$SO$_4$). The solvent was removed in vacuo and the pure product obtained by distillation under reduced pressure as a colourless liquid.

Yield=37 g (92%); b.p.=75°–78° C./0.6 mm Hg; $^1$H NMR (CDCl$_3$): δ0.93 (3H, t), 1.43 (4H, m), 1.83 (2H, q), 4.03 (2H, t), 6.74 (2H, m), 6.96 (1H, m); IR: 2968, 2942, 2882, 1624, 1517, 1487, 1473, 1322, 1294, 1257, 1076, 768, 710 cm$^{-1}$; MS: 200 [M]$^+$, 130.

EXAMPLE 39

2,3-Difluoro-1-n-hexoxybenzene

Quantities: 1-bromohexane (50 g, 0.3 mol), potassium carbonate (83 g, 0.6mol) and compound from Example 37 (39 g, 0.3 mol). The experimental procedure was as described in Example 38.

Yield=52.3 g (81%); b.p.=94°–98° C./0.7 mm Hg: $^1$H NMR (CDCl$_3$): δ0.89 (3H, t), 1.33 (4H, m), 1.45 (2H, q), 1.83 (2H, q), 4.03 (2H, t), 6.74 (2H, m), 6.96 (1H, m); IR: 2960, 2916, 2888, 1624, 1513, 1484, 1470, 1319, 1292, 1254, 1080, 766, 708 cm$^{-1}$; MS: 214 [M]$^+$, 130.

EXAMPLE 40

2,3-Difluoro-1-n-heptoxybenzene

Quantities: 1-bromoheptane (46.6 g, 0.26 mol), potassium carbonate (70 g, 0.5 mol) and compound from Example 37 (31.2 g, 0.24 mol). The experimental procedure was as described in Example 38.

Yield=48.5 g (89%); b.p.=119°–120° C./1 mm Hg; $^1$H NMR (CDCl$_3$): δ0.90 (3H, t), 1.30 (6H, m), 1.45 (2H, q), 1.80 (2H, q), 4.00 (2H, t), 6.74 (2H, m), 6.95 (1H, m); IR: 2960, 2940, 2880, 2860, 1625, 1520, 1485, 1472, 1320, 1295, 1255, 1080, 770, 710 cm$^{-1}$; MS: 228 [M]$^+$, 130.

EXAMPLE 41

2,3-Difluoro-1-n-octoxybenzene

Quantities: 1-bromooctane (34.9 g, 0.18 mol), potassium carbonate (50 g, 0.36 mol) and compound from Example 37 (21.7 g, 0.17 mol). The experimental procedure was as described in Example 38.

Yield=33.7 g (83%); b.p.=94°–99° C./0.25 mm Hg; $^1$H NMR (CDCl$_3$): δ0.89 (3H, t), 1.30 (8H, m), 1.45 (2H, q), 1.82 (2H, q), 4.02 (2H, t), 6.74 (2H, m), 6.96 (1, m); IR: 2940, 2864, 1622, 1518, 1485, 1472, 1322, 1295, 1257, 1080, 769, 710 cm$^{-1}$ MS: 242 [M]$^+$, 130.

EXAMPLE 42

2,3-Difluoro-1-n-nonoxybenzene

Quantities: 1-bromnononae (55.2 g, 0.27 mol), potassium carbonate (70 g, 0.5 mol) and compound from Example 37 (31.2 g, 0.24 mol). The experimental procedure was as described in Example 38.

Yield=55.68 (90%); b.p.=100°–105° C./0.05 mm Hg; $^1$H NMR (CDCl$_3$): δ0.90 (3H, t), 1.30 (10H, m), 1.45 (2H, q), 1.80 (2H, q), 4.00 (2H, t), 6.74 (2H, m), 6.95 (1H, m); IR: 2935, 2860, 1625, 1520, 1485, 1472, 1322, 1295, 1257, 1080, 770, 710 cm$^{-1}$; MS: 256 [M]$^+$, 130.

EXAMPLE 43

2,3-Difluoro-4-n-pentoxyphenylboronic acid

Quantities: n-butyllithium (20 cm$^3$, 10.0M in hexanes, 0.2 mol), compound from Example 38 (378, 0.19 mol) and triisopropyl borate (708, 0.38 mol). The experimental procedure was as described in Example 28.

Yield=458 (100%); $^1$H NMR (CDCl$_3$): δ0.94 (3H, t), 1.42 (4H, m), 1.84 (2H, q), 3.15 (2H, band), 4.07 (2H, t), 6.77 (1H, m), 7.44 (1H, m); IR: 3700–3000, 2960, 2940, 2870, 1630, 1520, 1470, 1365, 1306, 1222, 1084, 1030, 908, 820, 790, 747 cm$^{-1}$; MS: (180° C.); 678 [M]$^+$(trimer), 468, (120° C.); 244 [M]$^+$(monomer), 174, 130.

EXAMPLE 44

2,3-Difluoro-4-n-hexoxyphenylboronic acid

Quantifies: n-butyllithium (15 cm$^3$, 10.0M in hexanes, 0.15 mol), compound in Example 39 (31 g, 0.15 mol) and triisopropyl borate (56 g, 0.3 mol). The experimental procedure was as described in Example 28.

Yield=398 (100%); $^1$H NMR (CDCl$_3$): δ0.91 (3H, t), 1.35 (4H, m), 1.47 (2H, m), 1.82 (2H, q), 4.06 (2H, t), 6.77 (1H, m), 7.44 (1H, m), no obvious OH absorption: IR: 3700–3000, 2964, 2940, 2868, 1630, 1522, 1472, 1365, 1308, 1225, 1082, 1033, 821, 790, cm$^{-1}$; MS: 720 [M]$^+$ (trimer), 636, 552, 468.

EXAMPLE 45

2,3-Difluoro-4-n-heptoxyphenylboronic acid

Quantities: n-butyllithium (20 cm$^3$, 10.0M in hexanes, 0.2 mol), compound from Example 40 (45.5 g, 0.2 mol) and triisopropyl borate (74.4 g, 0.4 mol). The experimental procedure was as described in Example 28.

Yield=54 g (100%); $^1$H NMR (CDCl$_3$): δ0.90 (3H, t), 1.30 (6H, m), 1.45 (2H, q), 1.80 (2H, q), 4.05 (2H, t), 4,85 (2H, d), 6.78 (1H, m), 7.48 (1H, m); IR: 3600–3000, 2960, 2930, 2860, 1628, 1520, 1462, 1360, 1304, 1222, 1085, 1035, 820 cm$^{-1}$; MS: 272 [M]$^+$, 174, 146.

EXAMPLE 46

2,3-Difluoro-4-n-octoxyphenylboronic acid

Quantities: n-butyllithium (10 cm$^3$, 10.0M in hexanes, 0.1 mol), compound from Example 41 (23.4 g, 0.1 mol) and triisopropyl borate (37.6 g, 0.2 mol). The experimental procedure was as described in Example 28.

Yield=29 g (100%); $^1$H NMR (CDCl$_3$): δ0.90 (3H, t), 1.30 (8H, m), 1.45 (2H, q), 1.83 (2H, q), 4.07 (2H, t), 4.90 (1H, band), 6.78 (1H, m), 7.48 (1H, m); IR: 3700–3000, 2970, 2940, 2868, 1631, 1523, 1471, 1365, 1310, 1227, 1090, 1035, 908, 820, 788, 749 cm$^{-1}$; MS: 636, 468, 286 [M]$^+$, 268, 242.

EXAMPLE 47

2,3-Difluoro-4-n-nonoxyphenylboronic acid

Quantities: n-butyllithium (20 cm$^3$, 10.0M in hexanes, 0.2 mol), compound from Example 42 (51.6 g, 0.2 mol) and triisopropyl borate (74.4 g, 0.2 mol). The experimental procedure was as described in Example 28.

Yield=60 g (100%); $^1$H NMR (CDCl$_3$): δ0.88 (3H, t), 1.29 (10H, m), 1.45 (2H, q), 1.82 (2H, q), 2.18 (2H, s), 4.07 (2H, t), 6.78 (1H, m), 7.48 (1H, m); IR: 3700–3000, 2960, 2922, 2852, 1633, 1522, 1470, 1367, 1306, 1215, 1083, 820 cm$^{-1}$; MS: 300 [M]$^+$, 271, 256.

EXAMPLE 48

2-(4"-Pentoxy-2",3"-difluorobiphenyl-4'-yl)-5-n-pentyl-1,3-dioxane (Formula 8)

A solution of compound from Example 43 (1.34 g, 5.5 mmol) in ethanol (10 cm$^3$) was added to a vigorously stirred mixture of tetrakis(triphenylphosphine)palladium (0) (173 mg, 0.15 mmol), aqueous sodium carbonate (5 ml, 2M) and compound from Example 11 (1.57 g, 5 mmol) in benzene (15 cm$^3$). The reaction mixture was heated under reflux (23 h) then cooled to room temperature. Excess boronic acid was oxidized using 27% hydrogen peroxide (0.5 cm$^3$) over a period of 1 h. The mixture was extracted with diethyl ether (2×50 cm$^3$), and the ethereal extracts washed with saturated aqueous sodium chloride (2×50 cm$^3$) and dried (Na$_2$SO$_4$). The solvent was removed in vacuo and the product purified by flash column chromatography (dichloromethane/light petrol: 1:1 ) and recrystallisation from methanol/light petrol (1:1).

Yield=1.6 g (74%); Purity (HPLC): 99.84%; Mesomorphism (T/°C.): K 64.5 SmC 81.4N 140.4 Iso; $^1$H NMR (CDCl$_3$): δ0.90 (3H, t), 0.95 (3H, t), 1.11 (2H, q), 1.29 (8H, m), 1.45 (2H, m), 1.85 (2H, q), 2.14 (1H, m), 3.55 (2H, m), 4.07 (2H, t), 4.25 (2H, q), 5.46 (1H, s), 6.78 (1H, m), 7.07 (1H, m), 7.53 (4H, m); IR: 2966, 2932, 2864, 1630, 1510, 1472, 1388, 1320, 1303, 1294, 1128, 1081, 1021, 800 cm$^{-1}$; MS: 432 [M]$^+$, 361, 234.

EXAMPLE 49

2-(4"-Hexoxy-2",3"-difluorobiphenyl-4'-yl)-5-n-pentyl-1,3-dioxane

Quantities: compound from Example 11 (1.57 g, 5 mmol), compound from Example 44 (1.35 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.4 g (63%); Purity (HPLC); 99.29%; Mesomorphism (T/°C.): K 62.0 SmC 81.1 N 139.9 Iso; $^1$H NMR (CDCl$_3$): δ0.93 (6H, q), 1.12 (2H, q), 1.31 (8H, m), 1.36 (2H, m), 1.49 (2H, q), 1.85 (2H, q), 2.15 (1H, m), 3.56 (2H, t), 4.08 (2H, t), 4.26 (2H, q), 5.46 (1H, s), 6.79 (1H, m), 7.08 (1H, m), 7.54 (4H, m); IR: 2962, 2936, 2860, 1630, 1510, 1474, 1412, 1388, 1320, 1302, 1293, 1228, 1210, 1181, 1023, 800 cm$^{-1}$; MS: 446 [M]$^+$, 361, 234.

EXAMPLE 50

2-(4"-Heptoxy-2",3"-difluorobiphenyl-4'-yl)-5-n-pentyl-1,3-dioxane

Quantities: compound from Example 11 (1.57 g, 5 mmol), compound from Example 45 (1.54 g, 5.7 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.3 g (56%); Purity (HPLC): 99.93%; Mesomorphism (T/°C.): K 62.5 SmC 85.1N 134.6 Iso; $^1$H NMR (CDCl$_3$): δ0.90 (6H, t), 1.11 (2H, q), 1.31 (12H, m), 1.46 (2H, m), 1.84 (2H, q), 2.14 (1H, m), 3.56 (2H, t), 4.07 (2H, t), 4.25 (2H, q), 5.46 (1H, s), 6.78 (1H, m), 7.07 (1H, m), 7.53 (4H, m); IR: 2962, 2932, 2860, 1630, 1509, 1473, 1388, 1321, 1293, 1128, 1079, 1022, 801 cm$^{-1}$; MS: 460 [M]$^+$, 361, 234.

EXAMPLE 51

2-(4"-Octoxy-2",3"-difluorobiphenyl-4'-yl)-5-n-pentyl-1,3-dioxane

Quantities: compound from Example 11 (1.57 g, 5 mmol), compound from Example 46 (1.57 g, 5.5 mmol), tetrakis (triphenylphosphine)palladium(0) (173 mg, 0.15mmol) and aqueous sodium carbonate (5 cm$^3$, 2M). The experimental procedure was as described in Example 48.

Yield=1.4 g (59%); Purity (HPLC): 99.94%; Mesomorphism (T/°C.): K 62.0 SmC 85.8N 133.9 Iso; $^1$H NMR (CDCl$_3$): δ0.89 (6H, sex), 1.11 (2H, q), 1.30 (14H, m), 1.48 (2H, q), 1.84 (2H, q), 2.14 (1H, m), 3.56 (2H, t), 4.07 (2H, t), 4.26 (2H,q), 5.46 (1H, s), 6.78 (1H, m), 7.07 (1H, m), 7.53 (4H, m); IR: 2960, 2926, 2856, 1630, 1510, 1470, 1413, 1388, 1320, 1292, 1229, 1080, 1024, 800 cm$^{-1}$; MS: 474 [M]$^+$, 361, 234.

EXAMPLE 52

2-(4"-Nonoxy-2",3"-difluorobiphenyl-4'-yl)-5-n-pentyl-1,3-dioxane

Quantities: compound from Example 11 (1.57 g, 5 mmol), compound from Example 47 (1.65 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.0 g (41%); Purity (HPLC): 99.67%; Mesomorphism (T/°C.): K 62.5 SmC 86.9N 129.3 Iso; $^1$H NMR (CDCl$_3$): δ0.90 (6H, sex), 1.11 (2H, q), 1.30 (16H, m), 1.46 (2H, q), 1.84 (2H, q), 2.15 (1H, m), 3.56 (2H, t), 4.09 (2H, t), 4.26 (2H, q), 5.48 (1H, s), 6.78 (1H, m), 7.07 (1H, m), 7.54 (4H, m); IR: 2960, 2928, 2856, 1628, 1527, 1509, 1469, 1391, 1312, 1302, 1290, 1190, 1130, 1105, 1076, 1019, 805 cm$^{-1}$; MS: 488 [M]$^+$, 361, 234.

EXAMPLE 53

2-(4"-Pentyl-2",3"-difluorobiphenyl-4'-yl)-5-n-pentyl-1,3-dioxane

Quantities: compound from Example 11 (1.57 g, 5 mmol), compound from Example 28 (1.2 g, 5.25mmol), tetrakis (triphenylphosphine)palladium(0) (173 mg, 0.15 mmol) and aqueous sodium carbonate (5 cm$^3$, 2M). The experimental procedure was as described in Example 48.

Yield=1.5 g (72%); Purity (HPLC): 100.00%; Mesomorphism (T/°C.): K 64.5 119.6 Iso N 119.4 43.1 SmC; $^1$H NMR (CDCl$_3$): δ0.93 (6H, q), 1.12 (2H, q), 1.31 (10H, m), 1.65 (2H, q), 2.15 (1H, m), 2.68 (2H, t), 3.56 (2H, t), 4.27 (2H, q), 5.48 1H, s), 6.98 (1H, m), 7.09 (1H, m), 7.58 (4H, m); IR: 2968, 2930, 2860, 1493, 1466, 1405, 1385, 1127, 1085, 1023, 813 cm$^{-1}$; MS: 416 [M]$^+$, 288, 231.

EXAMPLE 54

2-(4"-Hexyl-2",3"-difluorobiphenyl-4'-yl)-5-n-pentyl-1,3-dioxane

Quantities: compound from Example 11 (1.57 g, 5 mmol), compound from Example 29 (1.33 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.5 g (70%); Purity (HPLC): 99.95%; Mesomorphism (T/°C.): K 63.1 SmC 74.9N 114.8 Iso; $^1$H NMR (CDCl$_3$): δ0.89 (6H, q), 1.11 (2H, q), 1.31 (12H, m), 1.63 (2H, q), 2.15 (1H, m), 2.68 (2H, t), 3.56 (2H, t), 4.26 (2H, q), 5.46 (1H, s), 6.97 (1H, m), 7.08 (1H, m), 7.55 (4H, m); IR: 2962, 2932, 2856, 1498, 1471, 1464, 1410, 1388, 1128, 1081, 1024, 812 cm$^{-1}$; MS: 430 [M]$^+$, 359, 346, 231.

EXAMPLE 55

2-(4"-Heptyl-2",3"-difluorobiphenyl-4'-yl)-5-n-pentyl-1,3-dioxane

Quantities: compound from Example 11 (1.57 g, 5 mmol), compound from Example 30 (1.34 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.5 g (68%); Purity (HPLC): 99.74%; Mesomorphism (T/°C.): K 67.5 SmC 71.8N 111.5 Iso; $^1$H NMR (CDCl$^3$): δ0.90 (6H, q), 1.12 (2H, q), 1.30 (14H, m), 1.64 (2H, q), 2.15 (1H, m), 2.68 (2H, t), 3.55 (2H, t), 4.26 (2H, q), 5.47 (1H, s), 6.98 (1H, m), 7.08 (1H, m), 7.56 (4H, m); IR: 2962, 2930, 2860, 1496, 1471, 1408, 1388, 1128, 1081, 1027, 812 cm$^{-1}$; MS: 444 [M]$^+$, 359, 345, 316, 231.

EXAMPLE 56

2-(4"-Octyl-2",3"-difluorobiphenyl-4'-yl)-5-n-pentyl-1,3-dioxane

Quantities: compound from Example 11 (1.57 g, 5 mmol), compound from Example 31 (1.49 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.3 g (57%); Purity (HPLC): 100.0%; Mesomorphism (T/°C.): K 68.0 SmC 73.5 N 110.1 Iso; $^1$H NMR (CDCl$^3$): δ0.89 (6H, q), 1.11 (2H, q), 1.28 (16H, m), 1.63 (2H, q), 2.15 (1H, m), 2.68 (2H, t), 3.55 (2H, t), 4.26 (2H, q), 5.48 (1H, s), 6.97 (1H, m), 7.07 (1H, m), 7.55 (4H, m); IR: 2962, 2926, 2856, 1500, 1473, 1467, 1411, 1389, 1128, 1082, 1027, 812 cm$^{-1}$; MS: 458 [M]$^+$, 359, 330, 233.

EXAMPLE 57

2-(4"-Nonyl-2",3"-difluorobiphenyl-4'-yl)-5-n-pentyl-1,3-dioxane

Quantities: compound from Example 11 (1.57 g, 5 mmol), compound from Example 32 (1.56 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.5 g (64%); Purity (HPLC): 100.0%; Mesomorphism (T/°C.): K 75.0 N 110.1 Iso; $^1$H NMR (CDCl$_3$): δ0.89 (6H, m), 1.11 (2H, q), 1.27 (18H, m), 1.63 (2H, q), 2.15 (1H, m), 2.68 (2H, t), 3.56 (2H, t), 4.26 (2H, q), 5.46 (1H, s), 6.97 (1H, m), 7.08 (1H, m), 7.55 (4H, m); IR: 2960, 2924, 2856, 1498, 1472, 1387, 1130, 1081, 1026, 812 cm$^{-1}$; MS: 472 [M]$^+$, 359, 344, 231.

EXAMPLE 58

2-(4"-Decyl-2",3"-difluorobiphenyl-4'-yl)-5-n-pentyl-1,3-dioxane

Quantities: compound from Example 11 (1.57 g, 5 mmol), compound from Example 33 (1.63 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.5 g (62%); Purity (HPLC): 99.83%; Mesomorphism (T/°C.): K 67.0 SmC 70.5 N 105.0 Iso; $^1$H NMR (CDCl$_3$): δ0.89 (6H, q), 1.11 (2H, q), 1.27 (20H, m), 1.63 (2H, q), 2.15 (1H, m), 2.68 (2H, t), 3.56 (2H, t), 4.26 (2H, q), 5.47 (1H, s), 6.97 (1H, m), 7.07 (1H, m),7.55 (4H, m); IR: 2960, 2928, 2852, 1500, 1473, 1411, 1389, 1128, 1082, 1027, 813 cm$^{-1}$; MS: 486 [M]$^+$, 358, 231.

EXAMPLE 59

2-(4"-Pentoxy-2",3"-difluorobiphenyl-4'-yl)-5-n-hexyl-1,3-dioxane

Quantities: compound from Example 12 (1.64 g, 5 mmol), compound from Example 43 (1.34 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.3 g (58%); Purity (HPLC): 99.90%; Mesomorphism (T/°C.): K 65.5 SmC 94.2 N 135.5 Iso; $^1$H NMR (CDCl$_3$): δ0.89 (6H, sex), 1.12 (2H, q), 1.31 (10H, m), 1.45 (2H, q). 1.85 (2H, q), 2.15 (1H, m), 3.56 (2H, t), 4.08 (2H, t), 4.25 (2H, q), 5.45 (1H, s), 6.78 (1H, m), 7.07 (1H, m), 7.53 (4H, m); IR: 2964, 2938, 2862, 1630, 1530, 1510, 1474, 1412, 1388, 1320, 1302, 1293, 1129, 1082, 1065, 1025, 801 cm$^{-1}$; MS: 446 [M]$^+$, 375, 234.

EXAMPLE 60

2-(4"-Hexoxy-2",3"-difluorobiphenyl-4'-yl)-5-n-hexyl-1,3-dioxane

Quantities: compound from Example 12 (1.64 g, 5 mmol), compound from Example 44 (1.35 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=0.2 g (9%); Purity (HPLC): 99.63%; Mesomorphism (T/°C.): K 64.7 SmC 95.6 N 135.1 Iso; $^1$H NMR (CDCl$_3$): δ0.91 (6H, q), 1.12 (2H, q), 1.31 (10H, m), 1.36 (2H, m), 1.49 (2H, q), 1.85 (2H, q), 2.15 (1H, q), 3.56 (2H, t), 4.08 (2H, t), 4.25 (2H, q), 5.45 (1H, s), 6.78 (1H, m), 7.07 (1H, m), 7.53 (4H, m); IR: 2964, 2934, 2860, 1630, 1507, 1470, 1411, 1387, 1316, 1303, 1127, 1105, 1080, 1012, 804 cm$^{-1}$; MS: 460 [M]$^+$, 375, 234.

EXAMPLE 61

2-(4"-Heptoxy-2",3"difluorobiphenyl-4'-yl )-5-n-hexyl-1,3-dioxane

Quantities: compound from Example 12 (1.64 g, 5 mmol), compound from Example 45 (1.43 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=0.7 g (30%); Purity (HPLC): 100.0%; Mesomorphism (T/°C.): K 57.2 SmC 99.0 N 130.9 Iso; $^1$H NMR (CDCl$_3$): δ0.93 (6H, t), 1.13 (2H, q), 1.33 (14H, m), 1.48 (2H, q), 1.85 (2H, q), 2.15 (1H, m), 3.55 (2H, t), 4.08 (2H, t), 4.26 (2H, q), 5.45 (1H, s), 6.78 (1H, m), 7.07 (1H, m), 7.53 (4H, m); IR: 2960, 2934, 2862, 1630, 1508, 1470, 1388, 1316, 1303, 1128, 1106, 1089, 1014, 805 cm$^{-1}$; MS: 474 [M]$^+$, 375, 234.

EXAMPLE 62

2-(4"-Octoxy-2",3"-difluorobiphenyl-4'yl)-5-n-hexyl-1,3-dioxane

Quantities: compound from Example 12 (1.64 g, 5 mmol), compound from Example 46 (1.50 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.35 g (55%); Purity (HPLC): 99.21%; Mesomorphism (T/°C.): K 52.5 SmC 97.7 N 129.4 Iso; $^1$H NMR (CDCl$_3$): δ0.93 (6H, t), 1.13 (2H, q), 1.34 (16H, m), 1.49 (2H, m), 1.86 (2H, q), 2.15 (1H, m), 3.57 (2H, t), 4.08 (2H, t), 4.26 (2H, q), 5.45 (1H, s), 6.78 (1H, m), 7.07 (1H, m), 7.52 (4H, m); IR: 2962, 2934, 2862, 1632, 1529, 1509, 1471, 1389, 1318, 1303, 1293, 1128, 1108, 1078, 1017, 801 cm$^{-1}$; MS: 488 [M]$^+$, 375, 234.

EXAMPLE 63

2-(4"-Nonoxy-2",3"-difluorobiphenyl-4'-yl)-5-n-hexyl-1,3-dioxane

Quantities: compound from Example 12 (1.64 g, 5 mmol), compound from Example 47 (1.57 g, 5.25 mmol), tetrakis (triphenylphosphine)palladium(0) (173 mg, 0.15 mmol) and aqueous sodium carbonate (5 cm$^3$, 2M). The experimental procedure was as described in Example 48 except for using 1,2-dimethoxy ethane (20ml) instead of benzene and ethanol.

Yield=0.85 g (34%); Purity (HPLC): 99.25%; Mesomorphism (T/°C.): K 56.5 SmC 86.5 N 120.0 Iso; $^1$H NMR (CDCl$_3$): δ0.91 (6H, q), 1.12 (2H, q), 1.31 (18H, m), 1.48 (2H, q), 1.85 (2H, q), 2.15 (1H, m), 3.55 (2H, t), 4.06 (2H, t), 4.25 (2H, q), 5.45 (1H, s), 6.78 (1H, m), 7.07 (1H, m), 7.53 (4H, m); IR: 2960, 2924, 2858, 1636, 1528, 1509, 1477, 1405, 1390, 1303, 1293, 1132, 1104, 1080, 1022, 803 cm$^{-1}$; MS: 502 [M]$^+$, 375, 234.

EXAMPLE 64

2-(4"-Pentyl-2",3"-difluorobiphenyl-4'-yl)-5-n-hexyl-1,3-dioxane

Quantities: compound from Example 12 (1.64 g, 5 mmol), compound from Example 28 (1.20 g, 5.25 mmol), tetrakis (triphenylphosphine)palladium(0) (173 mg, 0.15 mmol) and aqueous sodium carbonate (5 cm$^3$, 2M). The experimental procedure was as described in Example 63.

Yield=1.35 g (63%); Purity (HPLC): 99.79%; Mesomorphism (T/°C.): K 53.0 SmC 71.0 SmA 91.5N 114.6 Iso; $^1$H NMR (CDCl$_3$): δ0.92 (6H, q), 1.13 (2H, q), 1.32 (10H, m), 1.37 (2H, m), 1.64 (2H, q), 2.15 (1H, m), 2.69 (2H, t), 3.57 (2H, t), 4.26 (2H, q), 5.46 (1H, s), 6.97 (1H, m), 7.07 (1H, m), 7.53 (4H, m); IR: 2966, 2932, 2860, 1492, 1465, 1403, 1383, 1282, 1161, 1127, 1083, 1022, 812 cm$^{-1}$; MS: 430 [M]$^+$, 288, 231.

EXAMPLE 65

2-(4"Hexyl-2",3"-difluorobiphenyl-4'-yl)-5-n-hexyl-1,3-dioxane

Quantities: compound from Example 12 (1.64 g, 5 mmol), compound from Example 29 (1.30 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=0.7 g (32%); Purity (HPLC): 99.55%; Mesomorphism (T/°C.): K 61.3 SmC 85.0 SmA 93.0 N 111.2 Iso; $^1$H NMR (CDCl$_3$): δ0.90 (6H, t), 1.12 (2H, q), 1.30 (14H, m), 1.64 (2H, q), 2.15 (1H, m), 2.68 (2H, t), 3.56 (2H, t), 4.25 (2H, q), 5.46 (1H, s), 6.96 (1 H, m), 7.07 (1H, m), 7.55 (4H, m); IR: 2962, 2932, 2860, 1495, 1471, 1465, 1408, 1388, 1129, 1082, 1027, 813 cm$^{-1}$; MS: 444 [M]$^+$, 302, 231.

EXAMPLE 66

2-(4"-Heptyl-2",3"-difluorobiphenyl-4'-yl)-5-n-hexyl-1,3-dioxane

Quantities: compound from Example 12 (1.64 g, 5 mmol), compound from Example 30 (1.34 g, 5.25 mmol), tetrakis (triphenylphosphine)palladium(0) (173 mg, 0.15 mmol) and aqueous sodium carbonate (5 cm$^3$, 2M). The experimental procedure was as described in Example 63.

Yield=1.45 g (63%); Purity (HPLC): 99.77%; Mesomorphism (T/°C.): K 57.5 SmC 84.5 SmA 91.8 N 108.8 Iso; $^1$H NMR (CDCl$_3$): δ0.89 (6H, q), 1.12 (2H, q), 1.30 (16H, m), 1.64 (2H, q), 2.15 (1H, m), 2.68 (2H, t), 3.56 (2H, t), 4.26 (2H, q), 5.47 (1H, s), 6.97 (1H, m), 7.08 (1H, m), 7.55 (4H, m); IR: 2962, 2930, 2860, 1495, 1470, 1410, 1388, 1130, 1083, 1028, 812 cm$^{-1}$; MS: 458 [M]$^+$, 316, 231.

EXAMPLE 67

2-(4"-Octyl-2",3"-difluorobiphenyl-4'-yl)-5-n-hexyl-1,3-dioxane

Quantities: compound from Example 12 (1.64 g, 5 mmol), compound from Example 31 (1.42 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.
Yield=1.1 g (47%); Purity (HPLC): 99.71%; Mesomorphism (T/°C.): K 63.8 SmC 84.6 SmA 93.4 N 108.5 Iso; $^1$H NMR (CDCl$_3$): δ0.90 (6H, q), 1.12 (2H, q), 1.30 (18H, m), 1.64 (2H, q), 2.14 (1H, m), 2.68 (2H, t), 3.56 (2H, t), 4.25 (2H, q), 5.46 (1H, s), 6.96 (1H, m), 7.08 (1H, m), 7.54 (4H, m); IR: 2962, 2928, 2858, 1494, 1471, 1464, 1408, 1386, 1127, 1080, 1026, 812 cm$^{-1}$; MS: 472 [M]$^+$, 330, 231.

EXAMPLE 68

2-(4"-Nonyl-2",3"-difluorobiphenyl-4'-yl)-5-n-hexyl-1,3-dioxane

Quantities: compound from Example 12 (1.64 g, 5 mmol), compound from Example 32 (1.49 g, 5.25 mmol), tetrakis (triphenylphosphine)palladium(0) (173 mg, 0.15 mmol) and aqueous sodium carbonate (5 cm$^3$, 2M). The experimental procedure was as described in Example 63.

Yield=1.7 g (70%); Purity (HPLC): 99.72%; Mesomorphism (T/°C.): K 62.0 SmC 81.5 SmA 90.6 N 106.7 Iso; $^1$H NMR (CDCl$_3$): δ0.90 (6H, q), 1.11 (2H, q), 1.30 (20H, m), 1.64 (2H, q), 2.14 (1H, m), 2.68 (2H, t), 3.56 (2H, t), 4.25 (2H, q), 5.47 (1H, s), 6.97 (1H, m), 7.08 (1H, m), 7.55 (4H, m); IR: 2960, 2928, 2860, 1495, 1470, 1409, 1387, 1129, 1082, 1027, 812 cm$^{-1}$; MS: 486 [M]$^+$, 344, 231.

EXAMPLE 69

2-(4"-Decyl-2",3"-difluorobiphenyl-4'-yl)-5-n-hexyl-1,3-dioxane

Quantities: compound from Example 12 (1.64 g, 5 mmol), compound from Example 33 (1.63 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.2 g (48%); Purity (HPLC): 99.43%; Mesomorphism (T/°C.): K 68.7 SmC 79.8 SmA 89.8 N 103.2 Iso; $^1$H NMR (CDCl$_3$): δ0.90 (6H, m), 1.12 (2H, q), 1.30 (22H, m), 1.64 (2H, q), 2.15 (1H, m), 2.68 (2H, t), 3.57 (2H, t), 4.26 (2H, q), 5.47 (1H, s), 6.97 (1H, m), 7.08 (1H, m), 7.55 (4H, m); IR: 2960, 2930, 2858, 1495, 1471, 1467, 1408, 1387, 1129, 1082, 1028, 812 cm$^{-1}$; MS: 500 [M]$^+$, 358, 231.

EXAMPLE 70

2-(4"-Pentoxy-2",3"-difluorobiphenyl-4'-yl)-5-n-heptyl-1,3-dioxane

Quantities: compound from Example 13 (1.71 g, 5 mmol), compound from Example 43 (1.34 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.3 g (56%); Purity (HPLC): 99.87%; Mesomorphism (T/°C.): K 58.5 SmC 104.5 N 138.4 Iso; $^1$H NMR (CDCl$_3$): δ0.89 (3H, t), 0.94 (2H, t), 1.11 (2H, q), 1.29 (12H, m), 1.85 (2H, q), 2.14 (1H, m), 3.55 (2H, t), 4.07 (2H, t), 4.25 (2H, q), 5.46 (1H, s), 6.78 (1H, m), 7.07 (1H, m), 7.53 (4H, m); IR: 2962, 2926, 2832, 1633, 1530, 1508, 1472, 1389, 1318, 1303, 1292, 1083, 1065. 1022, 805 cm$^{-1}$; MS: 460 [M]$^+$, 389, 234.

EXAMPLE 71

2-(4"-Hexoxy-2",3"-difluorobiphenyl-4'-yl)-5-n-heptyl-1,3-dioxane

Quantities: compound from Example 13 (1.71 g, 5 mmol), compound from Example 44 (1.35 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.35 g (57%); Purity (HPLC): 99.72%; Mesomorphism (T/°C.): K 52.5 SmC 102.1 N 135.5 Iso; $^1$H NMR (CDCl$_3$): δ0.91 (6H, q), 1.12 (2H, q), 1.29 (12H, m), 1.35 (2H, m), 1.84 (2H, q), 2.14 (1H, m), 3.55 (2H, t), 4.08 (2H, t), 4.25 (2H, q), 5.47 (1H, s), 6.74 (1H, m), 7.07 (1H, m), 7.54 (4H, m); IR: 2964, 2934, 2860, 1630, 1528, 1508, 1471, 1388, 1316, 1303, 1129, 1105, 1075, 1028, 806 cm$^{-1}$; MS: 474 [M]$^+$, 390, 234.

EXAMPLE 72

2-(4"$^{11}$-Heptoxy-2",3"-difluorobiphenyl-4'-yl)-5-n-heptyl-1,3-dioxane

Quantities: compound from Example 13 (1.72 g, 5 mmol), compound from Example 45 (1.55 g, 5.7 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.2 g (49%); Purity (HPLC): 100.0%; Mesomorphism (T/°C.): K 58.7 SmC 110.0 N 134.6 Iso; $^1$H NMR (CDCl$_3$): δ0.89 (6H, t), 1.11 (2H, q), 1.30 (16H, m), 1.47 (2H, q), 1.84 (2H, q), 2.14 (1H, m), 3.57 (2H, t), 4.07 (2H, t), 4.25 (2H, q), 5.46 (1H, s), 6.78 (1H, m), 7.07 (1H, m), 7.53 (4H, m); IR: 2964, 2930, 2862, 1633, 1582, 1512, 1476, 1391, 1319, 1305, 1137, 1087, 1026, 807 cm$^{-1}$; MS: 488 [M]$^+$, 389, 234.

EXAMPLE 73

2-(4"-Heptoxy-2",3"-difluorobiphenyl-4'-yl)-5-n-heptyl-1,3-dioxane

Quantities: compound from Example 13 (1.71 g, 5 mmol), compound from Example 46 (1.57 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.7 g (68%); Purity (HPLC): 99.56%; Mesomorphism (T/°C.): K 55.0 SmC 102.6 N 129.4 Iso; $^1$H NMR (CDCl$_3$): δ0.91 (6H, m), 1.12 (2H, q), 1.31 (18H, m), 1.48 (2H, q), 1.85 (2H, q), 2.15 (1H, m), 3.56 (2H, t), 4.08 (2H, t), 4.26 (2H, q), 5.46 (1H, s), 6.78 (1H, m), 7.07 (1H, m), 7.52 (4H, m); IR: 2960, 2928, 2858, 1626, 1530, 1509, 1473, 1410, 1387, 1319, 1292, 1129, 1081, 1024, 800 cm$^{-1}$; MS: 502 [M]$^+$, 389, 234.

EXAMPLE 74

2-(4"-Heptoxy-2",3"-difluorobiphenyl-4'-yl)-5-n-heptyl-1,3-dioxane

Quantities: compound from Example 13 (1.9 g, 5.5 mmol), compound from Example 47 (1.5 g, 5 mmol), tetrakis(triphenylphosphine)palladium(0) (173 mg, 0.15 mmol) and aqueous sodium carbonate (5 cm$^3$, 2M). The experimental procedure was as described in Example 48.

Yield=0.66 g (26%); Purity (HPLC): 99.21%; Mesomorphism (T/°C.): K 56.9 SmC 110.7 N 130.5 Iso; $^1$H NMR (CDCl$_3$): δ0.90 (6H, q), 1.11 (2H, q), 1.33 (20H, m), 1.48 (2H, q), 1.83 (2H, q), 2.13 (1H, m), 3.58 (2H, t), 4.07 (2H, t), 4.23 (2H, q), 5.46 (1H, s), 6.78 (1H, m), 7.07 (1H, m), 7.54 (4H, m); IR: 2964, 2930, 2862, 1638, 1531, 1511, 1477, 1380, 1321, 1298, 1138, 1080, 1029, 808 cm$^{-1}$; MS: 516 [M]$^+$, 389, 234.

EXAMPLE 75

2-(4"-Heptoxy-2",3"-difluoro-biphenyl-4'-yl)-5-n-heptyl-1,3-dioxane

Quantities: compound from Example 13 (1.71 g, 5 mmol), compound from Example 28 (1.20 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.5 g (68%); Purity (HPLC): 100.0%; Mesomorphism (T/°C.): K 60.0 SmC 88.0 SmA 106.2 N 121.2 Iso; $^1$H NMR (CDCl$_3$): δ0.90 (6H, q), 1.12 (2H, q), 1.30 (12H, m), 1.36 (2H, m), 1.64 (2H, q), 2.15 (1H, m), 2.69 (2H, t), 3.57 (2H, t), 4.26 (2H, q), 5.47 (1H, s), 6.97 (1H, m), 7.08 (1H, m), 7.56 (4H, m); IR: 2968, 2934, 2860, 1492, 1467, 1404, 1385, 1127, 1086, 1023, 813 cm$^{-1}$; MS: 444 [M]$^+$, 288, 231.

EXAMPLE 76

2-(4"-Heptoxy-2",3"-difluorobiphenyl-4'-yl)-5-n-heptyl-1,3-dioxane

Quantities: compound from Example 13 (1.71 g, 5 mmol), compound from Example 29 (1.33 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.4 g (61%); Purity (HPLC): 99.69%; Mesomorphism (T/°C.): K 62.5 SmA 105.2 N 111.2 Iso; $^1$H NMR (CDCl$_3$): δ0.91 (6H, q), 1.11 (2H, q), 1.30 (16H, m), 1.64 (2H, q), 2.15 (1H, m), 2.68 (2H, t), 3.55 (2H, t), 4.25 (2H, q), 5.46 (1H, s), 6.96 (1H, m), 7.07 (1H, m), 7.53 (4H, m); IR: 2962, 2934, 2860, 1493, 1464, 1408, 1387, 1129, 1082, 1025, 811 cm$^{-1}$; MS: 458 [M]$^+$, 302, 231.

EXAMPLE 77

2-(4"-Heptoxy-2",3"-difluorobiphenyl-4'-yl)-5-n-heptyl-1,3-dioxane

Quantities: compound from Example 13 (1.71 g, 5 mmol), compound from Example 30 (1.34 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.3 g (55%); Purity (HPLC): 99.77%; Mesomorphism (T/°C.): K 63.5 SmC 68.5 SmA 106.0 N 114.2 Iso; $^1$H NMR (CDCl$_3$): δ0.90 (6H, t), 1.12 (2H, q), 1.30 (18H, m), 1.64 (2H, q), 2.15 (1H, m), 2.68 (2H, t), 3.57 (2H, t), 4.26 (2H, q), 5.47 (1H, s), 6.97 (1H, m), 7.08 (1H, m), 7.55 (4H, m); IR: 2962, 2930, 2862, 1470, 1410, 1388, 1129, 1082, 1026, 813 cm$^{-1}$; MS: 472 [M]$^+$, 316, 231.

EXAMPLE 78

2-(4"-Heptoxy-2",3"-difluorobiphenyl-4'-yl)-5-n-heptyl-1,3-dioxane

Quantities: compound from Example 13 (1.71 g, 5 mmol), compound from Example 31 (1.49 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.6 g (66%); Purity (HPLC): 99.67%; Mesomorphism (T/°C.): K 64.5 SmA N 105.9 N 110.8 Iso; $^1$H NMR (CDCl$_3$): δ0.90 (6H, m), 1.12 (2H, q), 1.30 (20H, m), 1.64 (2H, q), 2.15 (1H, m), 2.68 (2H, t), 3.56 (2H, t), 4.25 (2H, q), 5.46 (1H,s), 6.96 (1H, m), 7.07 (1H, m), 7.53 (4H, m); IR: 2960, 2930, 2858, 1494, 1470, 1408, 1387, 1128, 1081, 1025, 812 cm$^{-1}$; MS: 486 [M]$^+$, 330, 231.

EXAMPLE 79

2-(4"-Heptoxy-2",3"-difluorobiphenyl-4'-yl)-5-n-heptyl-1,3-dioxane

Quantities: compound from Example 13 (1.75 g, 5 mmol), compound from Example 32 (1.49 g, 5.25 mmol), tetrakis (triphenylphosphine)palladium(0) (174 mg, 0.15 mmol) and aqueous sodium carbonate (5 cm$^3$, 2M). The experimental procedure was as described in Example 48.

Yield=1.65 g (66%); Purity (HPLC): 100.0%; Mesomorphism (T/°C.): K 71.5 SmC 86.7 SmA 106.2 N 112.6 Iso; $^1$H NMR (CDCl$_3$): δ0.90 (6H, m), 1.12 (2H, q), 1.30 (22H, m), 1.65 (2H, q), 2.15 (1H, m), 2.69 (2H, t), 3.56 (2H, t), 4.25 (2H, q), 5.48 (1H, s) 6.97 (1H, m), 7.07 (1H, m), 7.53 (4H, m); IR: 2962, 2932, 2860, 1495, 1470, 1408, 1387, 1129, 1082, 1026, 813 cm$^{-1}$; MS: 500 [M]$^+$, 344, 231.

EXAMPLE 80

2-(4"-Heptoxy-2",3"-difluorobiphenyl-4'-yl)-5-n-heptyl-1,3-dioxane

Quantities: compound from Example 13 (1.71 g, 5 mmol), compound from Example 33 (1.63 g, 5.5 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.98 (74%); Purity (HPLC): 99.76%; Mesomorphism (T/°C.): K 66.0 SmA 104.1 N 107.8 Iso; $^1$H NMR (CDCl$_3$): δ0.89 (6H, q), 1.11 (2H, q), 1.30 (24H, m), 1.64 (2H, q), 2.15 (1H, m), 2.68 (2H, t), 3.57 (2H, t), 4.26 (2H, q), 5.48 (1H, s), 6.97 (1H, m), 7.08 (1H, m), 7.55 (4H, m); IR: 2960, 2930, 2860, 1493, 1470, 1405, 1386, 1128, 1081, 1025, 811 cm$^{-1}$; MS: 514 [M]$^+$, 359, 231.

EXAMPLE 81

2-(4"-Heptoxy-2",3"-difluorobiphenyl-4'-yl)-5-n-octyl-1,3-dioxane

Quantities: compound from Example 14 (1.80 g, 5 mmol), compound from Example 43 (1.28 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.58 (63%); Purity (HPLC): 100.0%; Mesomorphism (T/°C.): K 56.0 SmC 112.5 N 134.1 Iso; $^1$H NMR (CDCl$_3$): δ0.90 (6H, sex), 1.12 (2H, m), 1.30 (14H, m), 1.45 (2H, q), 1.84 (2H, q), 2.15 (1H, m), 3.56 (2H, t), 4.08 (2H, t), 4.26 (2H, q), 5.46 ()1H, s), 6.79 (1H, m), 7.07 (1H, m), 7.53 (4H, m); IR: 2962, 2928, 2858, 1633, 1504, 1472, 1406, 1395, 1317, 1290, 1132, 1105, 1078, 1025, 800 cm$^{-1}$; MS: 474 [M]$^+$, 404, 234.

EXAMPLE 82

2-(4"-Heptoxy-2",3"-difluorobiphenyl-4'-yl)-5-n-octyl-1,3-dioxane

Quantities: compound from Example 14 (1.80 g, 5 mmol), compound from Example 44 (1.35 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.75 g (72%); Purity (HPLC): 99.74%; Mesomorphism (T/°C.): K 51.5 SmC 102.5 SmA 108.0N 130.2 Iso; $^1$H NMR (CDCl$_3$): δ0.91 (6H, q), 1.12 (2H, q), 1.29 (14H, m), 1.35 (2H, m), 1.48 (2H, q), 1.85 (2H, q), 2.15 (1H, m), 3.56 (2H, t), 4.08 (2H, t) 4.26 (2H, q), 5.47 (1H, s), 6.79 (1H, m), 7.08 (1H, m), 7.55 (4H, m); IR: 2962, 2936, 2860, 1630, 1507, 1473, 1412, 1387, 1320, 1302, 1193, 1129, 1082, 1023, 800 cm$^{-1}$; MS: 488 [M]$^+$, 403, 234.

EXAMPLE 83

2-(4"-Heptoxy-2",3"-difluorobiphenyl-4'-yl)-5-n-octyl-1,3-dioxane

Quantities: compound from Example 14 (1.80 g, 5 mmol), compound from Example 45 (1.43 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.85 g (74%); Purity (HPLC): 99.67%; Mesomorphism (T/°C.): K 57.0 SmC 101.4 SmA 109.2N 122.8 Iso; $^1$H NMR (CDCl$_3$): δ0.90 (6H, m), 1.12 (2H, q), 1.29 (18H, m), 1.48 (2H, q), 1.85 (2H, q), 2.15 (1H, m), 3.56 (2H, t), 4.08 (2H, t), 4.26 (2H, q), 5.47 (1H, s), 6.78 (1H, m), 7.07 (1H, m), 7.55 (4H, m); IR: 2962, 2932, 2860, 1632, 1509, 1470, 1404, 1385, 1318, 1293, 1133, 1078, 1028, 824, 804 cm$^{-1}$; MS: 502 [M]$^+$, 403, 234.

EXAMPLE 84

2-(4"-Octoxy-2",3"-difluorobiphenyl-4'-yl)-5-n-octyl-1,3-dioxane

Quantities: compound from Example 14 (1.78 g, 5 mmol), compound from Example 46 (1.50 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.8 g (70%); Purity (HPLC): 100.0%; Mesomorphism (T/°C.): K 50.5 SmC 97.1 SmA 107.7N 120.2 Iso; $^1$H NMR (CDCl$_3$): δ0.90 (6H, t), 1.12 (2H, q), 1.30 (20H, m), 1.48 (2H, q), 1.84 (2H, q), 2.14 (1H, m), 3.55 (2H, t), 4.07 (2H, t), 4.25 (2H, q), 5.47 (1H, s), 6.78 (1H, m), 7.07 (1H, m), 7.53 (4H, m); IR: 2960, 2930, 2858, 1633, 1508, 1474, 1386, 1317, 1292, 1133, 1087, 1028, 802 cm$^{-1}$; MS: 516 [M]$^+$, 403, 234.

EXAMPLE 85

2-(4"-Nonoxy-2",3"-difluorobiphenyl-4'-yl)-5-n-octyl-1,3-dioxane

Quantities: compound from Example 14 (1.78 g, 5 mmol), compound from Example 47 (1.57 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.3 g (49%); Purity (HPLC): 99.63%; Mesomorphism (T/°C.): K 67.0 SmC 115.4N 127.6 Iso; $^1$H NMR (CDCl$_3$): δ0.90 (6H, t), 1.12 (2H, q), 1.30 (24H, m), 1.85 (2H, q), 2.15 (1H, m), 3.55 (2H, t), 4.07 (2H, t), 4.25 (2H, q), 5.46 (1H, s), 6.78 (1H, m), 7.07 (1H, m), 7.53 (4H, m); IR: 2932, 2858, 1635, 1508, 1474, 1404, 1387, 1318, 1298, 1133, 1077, 1028, 803 cm$^{-1}$; MS: 530 [M]$^+$, 403, 234.

EXAMPLE 86

2-(4"-Pentyl-2",3"-difluorobiphenyl-4'-yl)-5-n-octyl-1,3-dioxane

Quantities: compound from Example 13 (1.80 g, 5 mmol), compound from Example 28 (1.20 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.6 g (70%); Purity (HPLC): 99.82%; Mesomorphism (T/°C.): K 57 SmC 82.2 SmA 109.8N 115.1 Iso; $^1$H NMR (CDCl$_3$): δ0.91 (6H, q), 1.12(2H, q), 1.30 (14H, m), 1.36 (2H, m), 1.64 (2H, q), 2.15 (1H, m), 2.69 (2H, t), 3.57 (2H, t), 4.25 (2H, q) 5.48 (1H, s), 6.97 (1H, m), 7.08 (1H, m), 7.55 (4H, m); IR: 2962, 2934, 2862, 1494, 1470, 1408, 1388, 1130, 1082, 1026, 812 cm$^{-1}$; MS: 458 [M]$^+$, 288, 231.

EXAMPLE 87

2-(4"-hexyl-2",3"-difluorobiphenyl-4'-yl)-5-n-octyl-1,3-dioxane

Quantities: compound from Example 13 (1.78 g, 5 mmol), compound from Example 29 (1.30 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.4 g (54%); Purity (HPLC): 99.55%; Mesomorphism (T/°C.): K 60.8 SmC 97.2 SmA 110.9N 113.5 Iso; $^1$H NMR (CDCl$_3$): δ0.89 (6H, q), 1.11 (2H, q), 1.29 (18H, m), 1.64 (2H, q), 2.15 (1H, m), 2.68 (2H, t), 3.56 (2H, t), 4.25

(2H, q), 5.46 (1H, s), 6.96 (1H, m), 7.07 (1H, m), 7.54 (4H, m); IR: 2962, 2934, 2862, 1493, 1467, 1407, 1388, 1129, 1083, 1027, 813 cm$^{-1}$; MS: 472 [M]$^+$, 302, 231.

EXAMPLE 88

2-(4"-Heptyl-2",3"-difluorobiphenyl-4'-yl)-5-n-octyl-1,3-dioxane

Quantities: compound from Example 14 (2.04 g, 5.74 mmol), compound from Example 30 (1.60 g, 6.24 mmol), tetrakis(triphenylphosphine)palladium(0) (190 mg, 0.165 mmol) and aqueous sodium carbonate (5 cm$^3$, 2M). The experimental procedure was as described in Example 48

Yield=1.3 g (47%); Purity (HPLC): 99.72%; Mesomorphism (T/°C.): K 66.0 SmC 98.3 SmA 109.5N 113.7 Iso; $^1$H NMR (CDCl$_3$): δ0.89 (6H, t), 1.11 (2H, q), 1.29 (20H, m), 1.64 (2H, q), 2.14 (1H, m), 2.68 (2H, t), 3.55 (2H, t), 4.25 (2H, q), 5.45 (1H, s), 6.97 (1H, m), 7.07 (1H, m), 7.55 (4H, m); IR: 2960, 2932, 2860, 1493, 1470, 1407, 1387, 1129, 1081, 1025, 811 cm$^{-1}$; MS: 486 [M]$^+$, 316, 231.

EXAMPLE 89

2-(4"Octyl-2", 3"-difluorobiphenyl-4'-yl )-5-n-octyl-1,3-dioxane

Quantities: compound from Example 14 (1.80 g, 5 mmol), compound from Example 31 (1.42 g, 5.25 mmol), tetrakis (triphenylphosphine)palladium(0) (173 mg, 0. 15 mmol) and aqueous sodium carbonate (5 cm$^3$, 2M). The experimental procedure was as described in Example 48.

Yield=1.7 g (68%); Purity (HPLC): 99.83%; Mesomorphism (T/°C.): K 66.5 SmC 94.0 SmA 109.3N 110.9 Iso; $^1$H NMR (CDCl$_3$): δ0.90 (6H, q), 1.11 (2H, q), 1.30 (22H, m), 1.64 (2H, q), 2.15 (1H, m), 2.68 (2H, t), 3.55 (2H, t), 4.25 (2H, q), 5.46 (1H, s), 6.96 (1H, m), 7.07 (1H, m), 7.53 (4H, m): IR: 2960, 2930, 2858, 1493, 1470, 1407, 1386, 1129, 1081, 1024, 811 cm$^{-1}$; MS: 500 [M]$^+$, 330, 231.

EXAMPLE 90

2-(4"-Nonyl-2",3"-difluorobiphenyl-4'-yl)-5-n-octyl-1,3-dioxane

Quantities: compound from Example 14 (1.78 g, 5 mmol), compound from Example 32 (1.49 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.6 g (62%); Purity (HPLC): 99.83%; Mesomorphism (T/°C.): K 67.4 SmC 95.0 SmA 108.6N 110.8 Iso; $^1$H NMR (CDCl$_3$): δ0.90 (6H, q), 1.12 (2H, q), 1.31 (24H, m), 1.64 (2H, q), 2.15 (1H, m), 2.68 (2H, t), 3.56 (2H, t), 4.25 (2H, q), 5.47 (1H, s), 6.97 (1H, m), 7.08 (1H, m), 7.55 (4H, m); IR: 2960, 2928, 2858, 1494, 1470, 1407, 1387, 1128, 1081, 1025, 802 cm$^{-1}$; MS: 514 [M]$^+$, 344, 231.

EXAMPLE 91

2-(4"-Decyl-2",3"-difluorobiphenyl-4'-yl)-5-n-octyl-1,3-dioxane

Quantities: compound from Example 14 (1.78 g, 5 mmol), compound from Example 33 (1.57 g, 5.25 mmol), tetrakis (triphenylphosphine)palladium(0) (173 mg, 0. 15 mmol) and aqueous sodium carbonate (5 cm$^3$, 2M). The experimental procedure was as described in Example 48.

Yield=1.7 g (64%); Purity (HPLC): 99.74%; Mesomorphism (T/°C.): K 68.0 SmC 90.1 SmA 106.8N 107.5 Iso; $^1$H NMR (CDCl$_3$): δ0.91 (6H, q), 1.12 (2H, q), 1.32 (26H, m), 1.65 (2H, q), 2.15 (1H, m), 2.68 (2H, t), 3.55 (2H, t), 4.26 (2H, q), 5.46 (1H, s), 6.97 (1H, m), 7.07 (1H, m), 7.55 (4H, m); IR: 2962, 2930, 2860. 1494, 1474, 1406, 1387, 1129, 1082, 1027, 812 cm$^{-1}$; MS: 528 [M]$^+$, 358, 231.

EXAMPLE 92

2-(4"Pentoxy-2",3"-difluorobiphenyl-4'-yl)-5-n-oyl-1,3-dioxane

Quantities: compound from Example 15 (1.85 g, 5 mmol), compound from Example 43 (1.28 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=1.45 g (59%); Purity (HPLC): 99.57%; Mesomorphism (T/°C.): K 54.5 SmB 55.8 SmC 111.5 SmA 118.0N 130.8 Iso; $^1$H NMR (CDCl$_3$): δ0.92 (6H, m), 1.12 (2H, q), 1.30 (16H, ml, 1.45 (2H, m), 1.86 (2H, q), 2.15 (1H, m), 3.56 (2H, t), 4.07 (2H, t), 4.25 (2H, q), 5.47 (1H, s), 6.78 (1H, m), 7.07 (1H, m), 7.53 (4H, m); IR: 2958, 2922, 2844, 1633, 1505, 1468, 1383, 1301, 1128, 1072, 821, 793 cm$^{-1}$; MS: 516 [M]$^+$, 417, 234.

EXAMPLE 93

2-(4"-Hexoxy-2",3"-difluorobiphenyl-4'-yl)-5-n-nonyl-1,3-dioxane

Quantities: compound from Example 15 (1.85 g, 5 mmol), compound from Example 44 (1.35 g, 5.25 mmol), tetrakis (triphenylphosphine)palladium(0) (173 mg, 0.15 mmol) and aqueous sodium carbonate (5 cm$^3$, 2M). The experimental procedure was as described in Example 48.

Yield=0.65 g (26%); Purity (HPLC): 99.40%; Mesomorphism (T/°C.): K 54.0 SmC 121.1N 136.0 Iso; $^1$H NMR (CDCl$_3$): δ0.92 (6H, q), 1.12 (2H, q), 1.30 (16H, m), 1.36 (2H, m), 1.45 (2H, m), 1.84 (2H, q), 2.15 (1H, m), 3.56 (2H, t), 4.08 (2H, t,), 4.26 (2H, q), 5.47 (1H, s), 6.78 (1H, m), 7.07 (1H, m), 7.53 (4H, m); IR: 2960, 2936, 2862, 1638, 1509, 1478, 1397, 1320, 1304, 1295, 1135, 1108, 1080, 1029, 801 cm$^{-1}$; MS: 502 [M]$^+$, 417, 234.

EXAMPLE 94

2-(4"-Heptoxy-2",3"-difluorobiphenyl-4'-yl)-5-n-nonyl-1,3-dioxane

Quantities: compound from Example 15 (1.85 g, 5 mmol), compound from Example 45 (1.55 g, 5.7 mmol ), tetrakis (triphenylphosphine)palladium(0) (173 mg, 0.15 mmol) and aqueous sodium carbonate (5 cm$^3$, 2M). The experimental procedure was as described in Example 48.

Yield=1.4 g (54%); Purity (HPLC): 99.76%; Mesomorphism (T/°C.): K 54.0 SmC 121.7N 132.3 Iso; $^1$H NMR (CDCl$_3$): δ0.89 (6H, sex), 1.11 (2H, q), 1.27 (22H, m), 1.84 (2H, q), 2.14 (1H, m), 3.57 (2H, t), 4.07 (2H, t), 4.25 (2H, m), 5.45 (1H, s), 6.78 (1H, m), 7.07 (1H, m), 7.58 (4H, m); IR: 2958, 2932, 2850, 1635, 1530, 1510, 1470, 1385, 1318, 1293, 1133, 1077, 1028, 803 cm$^{-1}$; MS: 516 [M]$^+$, 417, 234.

EXAMPLE 95

2-(4"-Octoxy-2",3"-difluorobiphenyl-4'-yl)-5-n-nonyl-1,3-dioxane

Quantities: compound from Example 15 (1.85 g, 5 mmol), compound from Example 46 (1.5 g, 5.25 mmol), tetrakis (triphenylphosphine)palladium(0) (174 mg, 0. 15 mmol) and aqueous sodium carbonate (5 cm$^3$, 2M). The experimental procedure was as described in Example 48.

Yield=1.9 g (72%); Purity (HPLC): 99.52%; Mesomorphism (T/°C.): K 43.4 SmC 110.2 SmA 118.4N 127.7 Iso;

¹H NMR (CDCl₃): δ0.90 (6H, t), 1.12 (2H, q), 1.30 (22H, m), 1.45 (2H, q), 1.84 (2H, q), 2.15 (1H, m), 3.57 (2H, t), 4.08 (2H, t), 4.25 (2H, q), 5.47 (1H, s), 6.79 (1H, m), 7.08 (1H, m), 7.54 (4H, m); IR: 2958, 2920, 2848, 1633, 1505, 1468, 1383, 1300, 1128, 1070, 1020, 791 cm⁻¹; MS: 530 [M]⁺, 417, 234.

EXAMPLE 96

2-(4"-Nonoxy-2",3"-difluorobiphenyl-4'-y 1)-5-n-nonyl-1,3-dioxane

Quantities: compound from Example 15 (2.03 g, 5.5 mmol), compound from Example 47 (1.6 g, 5 mmol), tetrakis(triphenylphosphine)palladium(0) (173 mg, 0.15 mmol) and aqueous sodium carbonate (5 cm³, 2M). The experimental procedure was as described in Example 48.

Yield=1.4 g (51%); Purity (HPLC): 99.63%; Mesomorphism (T/°C.): K 61.1 SmC 122.3N 129.7 Iso; ¹H NMR (CDCl₃): δ0.89 (6H, t), 1.10 (2H, q), 1.29 (24H, m), 1.47 (2H, q), 1.84 (2H, q), 2.14 (1H, m), 3.56 (2H, t), 4.06 (2H, t), 4.25 (2H, q), 5.45 (1H, s) 6.78 (1H, m), 7.07 (1H, m), 7.53 (4H, m); IR: 2962, 2934, 2860, 1638, 1582, 1512, 1475, 1389, 1322, 1137, 1080, 1031, 808 cm⁻¹; MS: 544 [M]⁺, 417, 234.

EXAMPLE 97

2-(4"-Pentyl-2",3"-difluorobiphenyl-4'-yl)-5-n-nonyl-1,3-dioxane

Quantities: compound from Example 15 (1.85 g, 5 mmol), compound from Example 28 (1.2 g, 5.25 mmol), tetrakis(triphenylphosphine)palladium(0) (173 mg, 0.15 mmol) and aqueous sodium carbonate (5 cm³, 2M). The experimental procedure was as described in Example 48.

Yield=1.6 g (68%): Purity (HPLC): 99.55%; Mesomorphism (T/°C.): K 58 SmC 84.7 SmA 114.3N 115.8 Iso: ¹H NMR (CDCl₃): δ0.90 (6H, q), 1.11 (2H, q), 1.27 (16H, m), 1.35 (2H, q), 1.64 (2H, q), 2.15 (1H, m), 2.69 (2H, t), 3.56 (2H, t), 4.26 (2H, q), 5.49 (1H, s), 6.97 (1H, m), 7.08 (1H, m), 7.58 (4H, m); IR: 2960, 2930, 2852, 1497, 1469, 1410, 1386, 1168, 1131, 1083, 1026, 810 cm⁻¹; MS: 472 [M]⁺, 288, 231.

EXAMPLE 98

2-(4"-Hexyl-2",3"-difluorobiphenyl-4'-yl)-5-n-nonyl-1,3-dioxane

Quantities: compound from Example 15 (1.85 g, 5 mmol), compound from Example 29 (1.27 g, 5.25mmol), tetrakis(triphenylphosphine)palladium(0) (173 mg, 0.15 mmol) and aqueous sodium carbonate (5 cm³, 2M). The experimental procedure was as described in Example 63.

Yield=0.4 g (16%); Purity (HPLC): 99.58%; Mesomorphism (T/°C.): K 57.5 SmC 99.3N 113.4 Iso; ¹H NMR (CDCl₃): δ0.90 (6H, m), 1.12 (2H, q), 1.29 (20H, m), 1.64 (2H, q), 2.15 (1H, m), 2.69 (2H, t), 3.57 (2H, t), 4.26 (2H, t), 5.47 (1H, s), 6.97 (1H, m), 7.08 (1H, m), 7.55 (4H, m); IR: 2962, 2930, 2860, 1493, 1469, 1407, 1386, 1129, 1081, 1025, 811 cm⁻¹; MS: 486 [M]⁺, 302, 231.

EXAMPLE 99

2-(4"-Heptyl-2",3"-difluorobiphenyl-4'-yl)-5-n-nonyl-1,3-dioxane

Quantities: compound from Example 15 (1.85 g, 5 mmol), compound from Example 30 (1.34 g, 5.25 mmol), tetrakis(triphenylphosphine)palladium(0) (173 mg, 0.15 mmol) and aqueous sodium carbonate (5 cm³, 2M). The experimental procedure was as described in Example 63.

Yield=1.6 g (64%); Purity (HPLC): 100.0%; Mesomorphism (T/°C.): K 61.4 SmC 93.3 SmA 113.2N 113.5 Iso: ¹H NMR (CDCl₃): δ0.90(6H, q), 1.11 (2H, q), 1.30 (22H, m), 1.64 (2H, q), 2.15 (1H, m), 2.68 (2H, t), 3.56 (2H, t), 4.26 (2H, q), 5.46 (1H, s), 6.96 (1H, m), 7.07 (1H, m), 7.54 (4H, m); IR: 2962, 2932, 2860, 1496, 1470, 1408, 1387, 1130, 1083, 1027, 812 cm⁻¹; MS: 500 [M]⁺, 316, 231.

EXAMPLE 100

2-(4"-Octyl-2",3"-difluorobiphenyl-4'-yl)-5-n-nonyl-1,3-dioxane

Quantities: compound from Example 15 (1.85 g, 5 mmol), compound from Example 31 (1.42 g, 5.25mmol), tetrakis(triphenylphosphine)palladium(0) (173 mg, 0.15 mmol) and aqueous sodium carbonate (5 cm³, 2M). The experimental procedure was as described in Example 63.

Yield=1.95 g (76%); Purity (HPLC): 99.45%; Mesomorphism (T/°C.): K 64.0 SmC 97.3 SmA 113.0 Iso; ¹H NMR (CDCl₃): δ0.90(6H, q), 1.12 (2H, q), 1.30 (24H, m), 1.64 (2H, q), 2.15 (1H, m), 2.69 (2H, t), 3.56 (2H, t), 4.25 (2H, q), 5.45 (1H, s), 6.96 (1H, m), 7.07 (1H, m), 7.53 (4H, m); IR: 2962, 2930, 2858, 1495, 1470, 1408, 1387, 1130, 1083, 1026, 812 cm⁻¹; MS: 514 [M]⁺, 330, 231.

EXAMPLE 101

2-(4"-Nonyl-2",3"-difluorobiphenyl-4'-yl)-5-n-nonyl-1,3-dioxane

Quantities: compound from Example 15 (1.85 g, 5 mmol), compound from Example 32 (1.49 g, 5.25 mmol), tetrakis(triphenylphosphine)palladium(0) (173 mg, 0.15 mmol) and aqueous sodium carbonate (5 cm³, 2M). The experimental procedure was as described in Example 63.

Yield=2.0 g (76%); Purity (HPLC): 99.58%; Mesomorphism (T/°C.): K 69.0 SmC 98.2 SmA 112.2 Iso; ¹H NMR (CDCl₃): δ0.90(6H, q), 1.11 (2H, q), 1.30(26H, m), 1.64 (2H, q), 2.15 (1H, m), 2.69 (2H, t), 3.57 (2H, t), 4.26 (2H, q), 5.46 (1H, s), 6.96 (1H, m), 7.07 (1H, m), 7.53 (4H, m); IR: 2962, 2932, 2860, 1496, 1470, 1409, 1388, 1130, 1083, 1027, 813 cm⁻¹; MS: 528 [M]⁺, 344, 231.

EXAMPLE 102

2-(4"-Decyl-2",3"-difluorobiphenyl-4'-yl)-5-n-nonyl-1,3-dioxane

Quantities: compound from Example 15 (1.85 g, 5 mmol), compound from Example 33 (1.57 g, 5.25 mmol), tetrakis(triphenylphosphine)palladium(0) (173 mg, 0.15 mmol) and aqueous sodium carbonate (5 cm³, 2M). The experimental procedure was as described in Example 63.

Yield=2.2 g (81%); Purity (HPLC): 99.66%; Mesomorphism (T/°C.): K 68.0 SmC 95.1 SmA 111.1 Iso: ¹H NMR (CDCl₃): δ0.90(6H, q), 1.12 (2H, q), 1.30 (28H, m), 1.64 (2H, q), 2.15 (1H, m), 2.68 (2H, t), 3.56 (2H, t), 4.26 (2H, q), 5.46 (1H, s), 6.97 (1H, m), 7.08 (1H, m), 7.55 (4H, m); IR: 2962, 2932, 2860, 1496, 1470, 1407, 1387, 1129, 1082, 1027, 812 cm⁻¹; MS: 542 [M]⁺, 358, 231.

EXAMPLE 103

2-[4"-(2-Methylhexoxy)-2",3"-difluorobiphenyl-4'-yl]-5-n-nonyl-1,3-dioxane

Quantities: compound from Example 15 (1.85 g, 5 mmol), compound from Example 35 (1.43 g, 5.25 mmol), tetrakis(triphenylphosphine)palladium(0) (175 mg, 0.15 mmol) and aqueous sodium carbonate (5 cm³, 2M). The experimental procedure was as described in Example 48.

Yield=1.7 g (66%); Purity (HPLC): 99.56%; Mesomorphism (T/°C.): K 57.0 SmA 100.4 Iso; $^1$H NMR (CDCl$_3$): δ0.91 (6H, m), 1.05 (3H, d), 1.11 (2H, q), 1.28 (20H, m), 1.99 (1H, m), 2.14 (1H, m), 3.55 (2H, t), 3.83 (1H, q), 3.93 (1H, q), 4.25 (2H, t), 5.45 (1H, s), 6.78 (1H, m), 7.07 (1H, m), 7.53 (4H, m); IR: 2954, 2922, 2854, 1637, 1503, 1466, 1392, 1315, 1288, 1132, 1077, 1024, 798 cm$^{-1}$; MS: 516 [M]$^+$, 417, 234.

EXAMPLE 104

4-(5'-n-Pentyl-1',3'-dioxan-2'-yl) benzoic acid (Formula 13)

A solution of n-butyllithium (3 cm$^3$, 10.0M in hexanes, 30 mmol) was added dropwise to a stirred, cooled (−78° C.) solution of compound from Example 11 (9.4 g, 30 mmol) in dry THF (100 cm$^3$) under an atmosphere of dry nitrogen. The mixture was maintained under these conditions (35 min) then poured onto carbon dioxide granules. The product was extracted into 10% sodium hydroxide (2×150 cm$^3$) and the combined basic exacts acidified with hydrochloric acid (36%). The product was extracted into a mixture of diethyl ether and THF (3:1, 2×150 cm$^3$) and dried (MgSO$_4$). The solvent was removed in vacuo to yield a colourless solid.

Yield=7.8 g (93%); m.p.=206°–208° C.; $^1$H NMR (CDCl$_3$): δ0.90 (3H, t), 1.11 (2H, q), 1.30 (6H, m), 2.12 (1H, m), 3.55 (2H, t), 4.24 (2H, q), 5.45 (1H, s), 7.54 (2H, m), 8.04 (2H, m); IR: 3200–2500, 2970, 2936, 2868, 1712, 1697, 1615, 1580, 1470, 1427, 1385, 1288, 1130, 1082, 1020, 845, 765 cm$^{-1}$; MS: 278 [M]$^+$, 151.

EXAMPLE 105

4-(5'-n-Nonyl-1',3'-dioxan-2'-yl) benzoic acid

Quantities: n-butyllithium (2 cm$^3$, 10.0M in hexanes, 20 mmol), compound from Example 15 (7.4 g, 20 mmol). The experimental procedure was as described in Example 104.

Yield=5.0 g (75%); m.p.=197°–198° C.; $^1$H NMR (CDCl$_3$): δ0.89 (3H, t), 1.11 (2H, q), 1.27 (14H, m), 2.14 (1H, m), 3.55 (2H, t), 4.26 (2H, q), 5.46 (1H, s), 7.60 (2H, m), 8.10 (2H, m); IR: 3200–2500, 2964, 2930, 2856, 1682, 1430, 1387, 1293, 1130, 1087, 1023, 846, 763 cm$^{-1}$; MS: 334 [M]$^+$, 333, 214.

EXAMPLE 106

4-n-Nonyl-2,3-difluorophenol (Formula 14)

Quantities: compound from Example 32 (13.6 g, 60 mmol) and H$_2$O$_2$, (10%, 61 cm$^3$). The experimental procedure was described in Example 37.

Yield=12.6 g (98%); m.p.=29°–31° C.; $^1$H NMR (CDCl$_3$): δ0.88 (3H, t), 1.27 (12H, m), 1.57 (2H, m), 2.56 (2H, t), 4.98 (1H, d), 6.65–6.83 (2H, m); IR: 3600–3100, 2930, 2860, 1645, 1513, 1487, 1310, 1180, 1027, 821 cm$^{-1}$; MS: 256 [M]$^+$, 143.

EXAMPLE 107

4-n-Penyl-2,3-difluorophenol

Quantities: compound from Example 28 (13.6 g, 60 mmol) and H$_2$O$_2$ (10%, 61 cm$^3$). The experimental procedure was as described previously in Example 37.

Yield=11.2 g (93%); $^1$H NMR (CDCl$_3$): δ0.89 (3H, t), 1.32 (4H, m), 1.57 (2H, q), 2.57 (2H, t), 5.02 (1H, d), 6.69 (1H, m), 6.80 (1H, m): IR: 3600–3100, 2960, 2930, 2864, 1646, 1608, 1513, 1490, 1309, 1182, 1037, 812 cm$^{-1}$; MS: 200 [M]$^+$, 143.

EXAMPLE 108

4"-n-Nonyl-2",3"-difluorophenyl 4-(5-n-pentyl-1',3'-dioxan-2'-yl) benzoate (Formula 15)

A mixture of compound from Example 104 (1.28 g, 5 mmol), compound from Example 106 (1.39 g, 5 mmol), N,N'-dicyclohexylcarbodiimide (1.03 g, 5 mmol) and 4-(N, N'-dimethylamino)pyridine (0.06 g, 0.5 mmol) in sodium-dried diethyl ether (90 cm$^3$) and dry THF (60 cm$^3$) was stirred overnight at room temperature. The reaction mixture was filtered and the filtrate washed with water (2×25 cm$^3$) and dried (MgSO$_4$). The solvent was removed in vacuo and the product was purified by flash column chromatography (dichloromethane) and recrystallised from methanol/light petrol (1:1) to give colourless crystals.

Yield=0.85 g (33%); Purity (HPLC): 100.0%; Mesomorphism: (T/°C.) K 59 SmA 82 125.2 Iso (SmA-SmC 40); $^1$H NMR (CDCl$_3$): δ0.89 (6H, sex), 1.12 (2H, m), 1.29 (18H, m), 1.62 (2H, m), 2.15 (1H, m), 2.66 (2H, t), 3.56 (2H, t), 4.27 (2H, q), 5.49 (1H, s), 6.96 (2H, d), 7.64 (2H, d), 8.20 (2H, d); IR: 2928, 2856, 1753, 1503, 1485, 1470, 1272, 1250, 1128, 1073, 1030, 1020, 758 cm$^{-1}$; MS: 516 [M]$^+$, 471, 389, 261.

EXAMPLE 109

4"-n-Pentyl-2",3"-difluorophenyl 4-(5 '-n-nonyl-1',3'-dioxan-2'-yl) benzoate

Quantities: compound from Example 105 (1g, 5 mmol), compound from Example 107 (1.67 g, 5 mmol), N,N'-dicyclohexylcarbodiimide (1.03 g, 5 mmol), 4-(N,N'-dimethylamino)pyridine (0.06 g, 0.5 mmol). The experimental procedure was described in Example 108.

Yield=0.9 g (35%); Purity (HPLC): 100.0%; Mesomorphism: (T/°C.) K 65.9 SmA 115.9 130.1 Iso (SmA-SmC 70.3); $^1$HNMR (CDCl$_3$): δ0.90 (6H, sex), 1.11 (2H, q), 1.28 (16H, m), 1.34 (2H, q), 1.63 (2H, q), 2.15 (1H, m), 2.66 (2H, sex), 3.56 (2H, t), 4.27 (2H, q), 5.50 (1H, s), 6.96 (2H, d), 7.64 (2H, d), 8.20 (2H, sex); IR: 2960, 2928, 2862, 1741, 1500, 1490, 1470, 13.85, 1266, 1247, 1166, 1111, 1085, 1025, 812 cm$^{-1}$; MS: 516 [M]$^+$, 317.

EXAMPLE 110

4'-Bromo-2,3-difluoro-4-nonoxybiphenyl (Formula 17)

Quantities: tetrakis(triphenylphosphine)palladium(0) (0.87 g, 0.75 mmol), compound from Example 47 (9 g, 30 mmol) and 1-bromo-4-iodobenzene (7.07 g, 25 mmol). The experimental procedure was as described in Example 48 except that the reaction was carried out under conditions of reflux (5 h). The crude product was purified by flash column chromatography (light petrol/dichloro methane, 5:1) to give a colourless solid (9 g) which was recrystallised from light petrol to yield colourless crystals.

Yield=5.8 g (56%); m.p.=46°–47.5° C.; $^1$H NMR (CDCl$_3$): δ0.89 (3H, t), 1.28 (12H, m), 1.85 (2H, q), 4.07 (2H, t), 6.79 (1H, m), 7.06 (1H, m), 7.37 (2H, m), 7.56 (2H, m); IR: 2922, 2852, 1640, 1527, 1500, 1470, 1396, 1317, 1302, 1200, 1112, 1103, 1082, 1075, 804 cm$^{-1}$; MS: 412 [M]+, 410 [M]$^+$, 286, 284.

EXAMPLE 111

(2',3'-Difluoro-4'-n-nonoxybiphen-4'-yl) boronic acid (Formula 18)

Quantities: compound from Example 110 (2.8 g, 6.8 mmol), n-butyllithium (4.4 cm$^3$, 1.55M in hexanes, 6.8 mmol) and triisopropyl borate (2.6 g, 13.8mmol). The experimental procedure was as described in Example 36.

Yield=2.6 g (100%); $^1$H NMR (CDCl$_3$): δ0.89 (3H, m), 1.29 (12H, m), 1.87 (2H, m), 2.32 (2H, band), 4.10 (2H, m), 6.83 (1H, m), 7.15 (1H, m), 7.34–7.58 (1H, m), 7.67 (1H, q), 7.81 (1H, d), 8.33 (1H, d) ;IR: 3700–3000, 2960, 2924, 2856, 1613, 1516, 1470, 1402, 1198, 1082, 803 cm$^{-1}$; MS: 332 [M-B(OH)$_2$]$^+$, 206.

EXAMPLE 112

1-(2",3"-Difluoro-4"-n-nonoxy-4'-biphenyl)-4-n-heptyl-2,6-dioxaborinane (Formula 19)

Quantities: compound from Example 111 (1.9 g, 5 mmol) and compound from Example 8 (0.9 g, 5 mmol). The experimental procedure was as described in Example 11 except the product purified by flash column chromatography (dichloromethane/light petrol: 1:1) and recrystallisation from a mixture of light petrol/methanol (3:1), Yield=1.4 g (54 %); Purity (HPLC): 99.75%; Mesomorphism: (T/°C.) K 72.5 SmC 81.5N N 109.5 Iso; $^1$H NMR (CDCl$_3$): δ0.89 (6H, t), 1.29 (24H, m), 1.85 (2H, q), 2.10 (1H, m), 3.78 (2H, t), 4.07 (2H, t), 4.19 (2H, q), 6.79 (1H, m), 7.11 (1H, m), 7.49 (2H, m), 7.83 (2H, m); IR: 2940, 2872, 1617, 1533, 1513, 1486, 1478, 1432, 1355, 1322, 1305, 1255, 1088, 816 cm$^{-1}$; MS: 514 [M]$^+$, 388, 232.

EXAMPLE 113

1-(2",3"-Difluoro-4"n-nonoxy-4'biphenyl)-4-n-heptyl-2,6-dioxaborinane

Quantities: compound from Example 111 (1.9 g, 5 mmol) and compound from Example 10 (0.9 g, 5 mmol). The experimental procedure was as described in Example 112.

Yield=1.6 g (59 %); Purity (HPLC): 99.58%; Mesomorphism: CT/°C.) K 55.5 SmC 103.5N N 111.3 Iso; $^1$H NMR (CDCl$_3$): δ0.88 (6H, t), 1.28 (26H, m), 1.48 (2H, q), 1.84 (2H, q), 2.08 (1H, m), 3.78 (2H, t), 4.07 (2H, t), 4.19 (2H, q), 6.79 (1H, m), 7.10 (1H, m), 7.49 (2H, q), 7.83 (2H, d); IR: 2960, 2912, 2858, 1630, 1606, 1524, 1465, 1345, 1312, 1069, 890, 835 cm$^{-1}$; MS: 542 [M]$^+$, 415, 231.

EXAMPLE 114

2-(2',3'-Difluorophenyl)-5-n-heptyl-1,3-dioxane (Formula 18)

Quantities: compound from Example 8 (27 g, 0.155 mol), 2,3-difluorobenzaldehyde (21.5 g, 0.15 mol) and 4-toluenesulphonic acid (100 mg). The experimental procedure was as described in Example 11 except using dry benzene instead of dry toluene.

Yield=12.6 g (28%); m.p.=20°–21° C.; $^1$H NMR (CDCl$_3$): δ0.89 (3H, t), 1.10 (2H, q), 1.28 (10H, m), 2.15 (1H, m), 3.56 (2H, t), 4.23 (2H, q), 5.75 (1H, s), 7.11 (2H, m), 7.38 (1H, m); IR: 2974, 2944, 2870, 1641, 1610, 1500, 1473, 1405, 1292, 1135, 1105, 1032, 810, 787, 730 cm$^{-1}$; MS: 298 [M]$^+$, 185, 141.

EXAMPLE 115

2-(2',3'-Difluorophenyl)-5-n-nonyl-1,3-dioxane

Quantities: compound from Example 10 (31.4 g, 0.155 mol), 2,3-difluorobenzaldehyde (21.5 g, 0.15 mol) and 4-toluenesulphonic acid (100 mg). The experimental procedure was as described in Example 114.

Yield=26.9 g (55%); m.p.=27.5°–28.5° C.; $^1$H NMR (CDCl$_3$): δ0.89 (3H, t), 1.10 (2H, q), 1.28 (14H, m), 2.15 (1H, m), 3.56 (2H, t), 4.26 (2H, q), 5.71 (1H, s), 7.11 (2H, m), 7.38 (1H, m); IR: 2948, 2920, 2844, 1630, 1600, 1486, 1464, 1394, 1385, 1282, 1205, 1145, 1125, 1039, 1023, 834 cm$^{-1}$; MS: 326 [M]$^+$, 212, 140.

EXAMPLE 116

2,3-Difluoro-4-(5'-n-heptyl-1',3'-dioxan-2'-yl) phenylboronic acid (Formula 22)

Quantities: compound from Example 114 (9.0 g, 30 mmol), n-butyllithium (3 cm$^3$, 10.0M in hexanes, 30 mmol) and triisopropyl borate (11.4 g, 60 mmol). The experimental procedure was as described in Example 36.

Yield=10.3 g (100%); $^1$H NMR (CDCl$_3$): δ0.89 (3H, m), 1.11 (2H, q), 1.28 (10H, m), 2.12 (1H, m), 3.58 (2H, t), 4.21 (2H, q), 5.68 (1H, s), 7.58 (2H, m), 10.33 (2H, s); IR: 3700–3000, 2946, 2916, 2846, 2256, 1675, 1448, 1340, 1312, 1260, 1217, 1188, 1150, 1127, 980, 808 cm$^{-1}$; MS: 324 [M-H$_2$O]$^+$, 206.

EXAMPLE 117

2,3-Difluoro-4-(5'-n-nonyl-1',3'-dioxan-2'-yl) phenylboronic acid

Quantities: compound from Example 115 (8.6 g, 26 mmol), n-butyllithium (2.6 cm$^3$, 10.0M in hexanes, 26 mmol) and triisopropyl borate (9.8 g, 52 mmol). The experimental procedure was as described in Example 36.

Yield=9.6 g (100 %); $^1$H NMR (CDCl$_3$): δ0.88 (3H, t), 1.10 (2H, q), 1.28 (12H, m), 2.14 (1H, m), 3.56 (2H, t), 4.20 (2H, sex), 5.70 (1H, s), 7.35 (1H, m), 7.55 (1H, m), 10.35 (2H, s); IR: 3700–3000, 2962, 2932, 2860, 2264, 1680, 1486, 1453, 1388, 1343, 1320, 1295, 1261, 1157, 1034, 970, 843, 812 cm$^{-1}$; MS: 353 [M-OH]$^+$, 213, 195.

EXAMPLE 118

2-(2',3'-Difluoro-4'-heptylphenyl)-5-n-nonyl-1,3-dioxane (Formula 25)

n-Butyllithium (3.4 cm$^3$, 10.0M in hexanes, 34mmol) was added dropwise to a stirred, cooled (−78° C.) solution of compound from Example 115 (mixture with isomers) (11.2 g, 34 mmol) in dry THF (100 cm$^3$) under an atmosphere of dry nitrogen. The mixture was maintained under these conditions (3 h) then a solution of 1-iodoheptane (7.7 g, 34 mmol) in dry THF (20 cm$^3$) was added dropwise at −78° C. The temperature of the reaction mixture was allowed to reach room temperature overnight. After separation, the aqueous layer was extracted with diethyl ether (2×150 cm$^3$), the combined ethereal layers washed with water (2×150 cm$^3$) and dried (MgSO$_4$). The solvent was removed in vacuo to give the product as a brown oil which was purified by distillation under reduced pressure and recrystallised several times from methanol to remove the cis-isomer.

Yield=2.5 g (17%); b.p.=94°–98° C./ 1.0 mm Hg; m.p.= 40.4° C.; Purity (HPLC): 96.91%; $^1$H NMR (CDCl$_3$): δ0.88 (6H, sex), 1.09 (2H, q), 1.27 (22H, m), 1.57 (2H, q), 2.14 (1H, m), 2.64 (2H, t), 3.55 (2H, t), 4.22 (2H, q), 5.69 (1H, s), 6.94 (1H, m), 7.27 (1H, m); IR: 2964, 2928, 2860, 1644, 1471, 1401, 1387, 1292, 1162, 1145, 1131, 1091, 1022, 971, 835, 813 cm$^{-1}$; MS: 424 [M]$^+$, 325, 241.

EXAMPLE 119

4-n-Heptoxybenzaldehyde

Anhydrous potassium carbonate (55.5 g, 0.4 mol) was added to a stirred solution of 4-hydroxybenzaldehyde (24.5 g, 0.2 mol) in acetone (300 cm$^3$), over a period of 30 min at room temperature. 1-Bromoheptane (40.3 g, 0.225 mol) was added dropwise and the resulting mixture heated under reflux (12 h). The solution was poured into water (1000 cm$^3$), the product extracted into diethyl ether (2×300 cm$^3$), and the combined ethereal extracts dried (MgSO$_4$). The solvent was removed in vacuo and the product isolated as a colourless oil by distillation under reduced pressure.

Yield=31 g (70%); b.p.=139°–141° C./1.2 mm Hg; $^1$H NMR (CDCl$_3$): δ0.90 (3H, t), 1.30 (6H, m), 1.45 (2H, q), 4.05 (2H, t), 7.00 (2H, m), 7.85 (2H, m), 9.90 (1H, s); IR: 2935, 2860, 2805, 2740, 1695, 1580, 1513, 1472, 1315, 1260, 1218, 1162, 835 cm$^{-1}$; MS: 220 [M]$^+$, 121.

EXAMPLE 120

1-Bromo-4-heptoxybenzene

Quantities: anhydrous potassium carbonate (34.8 g, 0.25 mol), 1-bromoheptane (19.6 g, 0.11 mol) and 4-bromophenol (17.3 g, 0.1 mol). The experimental procedure was as described in Example 119.

Yield=25.5 g (94%); b.p.=130°–134° C./0.2 mm Hg; $^1$H NMR (CDCl$_3$): δ0.90 (3H, t), 1.33 (6H, m), 1.45 (2H, q), 1.77 (2H, q), 3.91 (2H, t), 6.78 (2H, m), 7.38 (2H, m); IR: 2934, 2864, 1490, 1470, 1296, 1246, 1174, 1076, 1006, 824, 647,512 cm$^{-1}$; MS: 272[M]$^+$, 270[M]$^+$, 174, 172.

EXAMPLE 121

1-Iodo-4-octoxybenzene

Quantities: anhydrous potassium carbonate (30 g, 0.22 mol), 1-bromooctane (11.7 g, 0.06 mol) and 4-iodophenol (11.0 g, 0.05 mol). The experimental procedure was as described in Example 119.

Yield=16.3 g (98%); b.p.=138°–148° C./0.1 mm Hg; $^1$H NMR (CDCl$_3$): δ0.89 (3H, t), 1.30 (8H, m), 1.43 (2H, q), 1.77 (2H, q), 3.90 (2H, t), 6.68 (2H, m), 7.55 (2H, m); IR: 2928, 2860, 1590, 1573, 1489, 1470, 1302, 1286, 1246, 1176, 1062, 1030, 1002, 822, 510 cm$^{-1}$; MS: 332 [M]$^+$, 220.

EXAMPLE 122

1-Bromo-4-nonoxybenzene

Quantities: anhydrous potassium carbonate (60 g, 0.43 mol), 1-bromononane (45.3 g, 0.22 mol) and 4-bromophenol (34.6 g, 0.2 mol). The experimental procedure was as described in Example 119.

Yield=57.9 g (97%); b.p.=117°–123° C./0.08 mm Hg; $^1$H NMR (CDCl$_3$): δ0.90 (3H, t), 1.30 (10H, m), 1.45 (2H, q), 1.77 (2H, q), 3.93 (2H, t), 6.78 (2H, m), 7.37 (2H, m); IR: 2940, 2868, 1593, 1581, 1494, 1472, 1290, 1250, 1174, 1075, 1005, 825 cm$^{-1}$; MS: 300 [M]$^+$, 298 [M]$^+$, 174, 172.

EXAMPLE 123

2-(4"-Heptoxy-2',3'-difluorobiphenyl-4'-yl)-5-n-heptyl-1,3-dioxane (Formula 24)

Quantities: tetrakis(triphenylphosphine)palladium(0) (173 mg, 0.15 mmol), compound from Example 116 (1.75 g, 5.12 mmol) and compound from Example 120 (1.36 g, 5 mmol). The experimental procedure was as described in Example 48.

Yield=0.3 g (12%); Purity (HPLC): 99.87%; Mesomorphism (T/°C.): K 77.2N 125.2 Iso; $^1$H NMR (CDCl$_3$): δ0.90 (6H, m), 1.11 (2H, q), 1.28 (16H, m), 1.47 (2H, m), 1.82 (2H, q), 2.16 (1H, m), 3.58 (2H, t), 4.00 (2H, t), 4.24 (2H, q), 5.73 (1H, s), 6.96 (2H, sex), 7.19 (1H, m), 7.39 (1H, m), 7.45 (2H, m); IR: 2954, 2920, 2851, 1612, 1526, 1495, 1467, 1384, 1249, 1241, 1182, 1129, 1103, 1026, 826, 810 cm$^{-1}$; MS: 488 [M]$^+$, 382, 234, 214.

EXAMPLE 124

2-(4"-Octoxy-2',3'-difluorobiphenyl-4'-yl)-5-n-heptyl-1,3-dioxane

Quantities: tetrakis(triphenylphosphine )palladium(0) (173 mg, 0.15 mmol ), compound from Example 116 (1.75 g, 5.12 mmol) and compound from Example 121 (1.66 g, 5 mmol). The experimental procedure was as described in Example 48.

Yield=0.65 g (26%); Purity (HPLC): 99.53%; Mesomorphism (T/°C.): K 84.4N 124.6 Iso: $^1$H NMR (CDCl$_3$): δ0.89 (6H, t), 1.11 (2H, q), 1.28 (18H, m), 1.47 (2H, m), 1.81 (2H, q), 2.16 (1H, m), 3.58 (2H, t), 4.00 (2H, t), 4.24 (2H, q), 5.73 (1H, s), 6.97 (2H, m), 7.19 (1H, m), 7.39 (1H, m), 7.43 (2H, m); IR: 2954, 2920, 2852, 1611, 1526, 1494, 1467, 1383, 1244, 1181, 1128, 1103, 1024, 824, 808 cm$^{-1}$; MS: 502 [M]$^+$, 390, 374, 346, 234.

EXAMPLE 125

2-(4"-Nonoxy-2',3'-difluorobiphenyl-4'-yl)-5-n-heptyl-1,3-dioxane

Quantities: tetrakis(triphenylphosphine)palladium(0) (173 mg, 0.15 mmol), compound from Example 116 (1.75 g, 5.12 mmol) and compound from Example 122 (1.36 g, 5 mmol). The experimental procedure was as described in Example 63.

Yield=0.6 g (23%); Purity (HPLC): 99.20%; Mesomorphism (T/°C.): K 86.2N 120.4 Iso; $^1$H NMR (CDCl$_3$): δ0.89 (6H, q), 1.11 (2H, q), 1.29 (20H, m), 1.47 (2H, m), 1.81 (2H, q), 2.16 (1H, m), 3.58 (2H, t), 4.00 (2H, t), 4.24 (2H, q), 5.74 (1H, s), 6.96 (1H, sex), 7.19 (1H, m), 7.39 (1H, m), 7.45 (2H, m); IR: 2962, 2928, 2858, 1612, 1528, 1497, 1471, 1388, 1245, 1184, 1131, 1107, 1029, 830, 814 cm$^{-1}$; MS: 516 [M]$^+$, 389, 361, 234.

EXAMPLE 126

2,3-Difluoro-4-(5-nonyl-1,3-dioxan-2-yl) phenol (Formula 26)

Hydrogen peroxide (10 %, 9 cm$^3$, 26 mmol) was added dropwise to a stirred mixture of compound from Example 117 (1.6 g, 4.5 mmol) in diethyl ether (20 cm$^3$) and aqueous sodium carbonate (5 cm$^3$, 2M) and heated under reflux. The stirred mixture was heated under reflux for a further 2.5 h then cooled. The ethereal layer was separated and the aqueous layer was extracted with diethyl ether (2×200 cm$^3$). The combined ethereal layers were dried (MgSO$_4$). The solvent was removed in vacuo and the product was purified by flash column chromatography (dichloromethane).

Yield=0;5 g (32.4 %); m.p.=63°–65° C.; $^1$H NMR (CDCl$_3$): δ0.91 (3H, t), 1.10 (2H, q), 1.30 (14H, m), 2.13 (1H, m), 3.55 (2H, t), 4.22 (2H, q), 5.24 (1H, band), 5.62 (1H, s), 6.83 (1H, m), 7.27 (1H, m); IR: 3700–3300, 2952, 2920, 2850, 1640, 1522, 1489, 1464, 1389, 1316, 1126, 1090, 1025, 973, 830, 810 cm$^{-1}$; MS: 342 [M]$^+$, 288, 203.

EXAMPLE 127

2-(2,3-Difluoro-4-heptoxyphenyl)-5-nonyl-1,3-dioxane (Formula 27)

Quantities: 1-bromoheptane (0.31 g, 1.46 mmol), potassium carbonate (0.4 g, 3 mmol) and compound from Example 126 (0.Sg, 1.46 mmol). The experimental procedure was as described in Example 38.

Yield=0.25 g (39 %); Purity (HPLC): 97.95 %; Mesomorphism (T/°C.): K 47 (SmA 7) Iso; $^1$H NMR (CDCl$_3$): δ0.89 (6H, t), 1.09(2H, q), 1.27 (22H, m), 1.80 (2H, qn), 2.12 (1H, m), 3.54 (2H, t), 4.03 (2H, t), 4.21 (2H,), 5.63 (1H, s), 6.73 (1H, m), 7.27 (1H, m); IR: 2964, 2920, 2858, 1630, 1515, 1484, 1463, 1394, 1317, 1292, 1130, 1090, 1021, 803 cm$^{-1}$; MS: 440 [M]$^+$, 341, 325, 256, 159.

EXAMPLE 128

2-(2,3-Difluorobiphenyl-4'-yl)-5-octyl-1,3-dioxane (Formula 29)

Quantities: compound from Example 14 (10.7 g, 30 mmol), compound from Example 36 (5.5 g, 35 mmol), tetrakis(triphenylphosphine)palladium(0) (1.04 mg, 0.9 mmol) and aqueous sodium carbonate (30 cm$^3$, 2M). The experimental procedure was as described in Example 63.

Yield=10.8 g (92.7 %); Purity (HPLC): 98.63 %; Mesomorphism (T/°C.): K 52.2 SmA 77.0 Iso; $^1$H NMR (CDCl$_3$): δ0.89 (3H, t), 1.11 (2H, q), 1.28 (12H, m), 2.15 (1H, m), 3.56 (2H, t), 4.26 (2H, q), 5.48 (1H, s), 7.14 (3H, m), 7.56 (4H, m); IR: 2962, 2932, 2858, 1626, 1593, 1573, 1483, 1408, 1386, 1261, 1127, 1083, 1028, 1020, 897, 812, 786 cm$^{-1}$; MS: 388 [M]$^+$, 275, 217.

EXAMPLE 129

2-(2,3-Difluorobiphenyl-4-yl)-5-nonyl-1,3-dioxane

Quantities: compound from Example 15 (7.4 g, 20 mmol), compound from Example 36 (3.5 g, 22 mmol), tetrakis (triphenylphosphine)palladium(0) (1.16 mg, 1 mmol) and aqueous sodium carbonate (20 cm$^3$, 2M). The experimental procedure was as described in Example 48.

Yield=6.5 g (73.4 %); Purity (HPLC): 97.57 %; Mesomorphism (T/°C.): K 74.0 SmA 75.1 Iso; $^1$H NMR (CDCl$_3$): δ0.89 (3H, t), 1.28 (16H, m), 2.15 (1H, m), 3.56 (2H, t), 4.26 (2H, q), 5.47 (1H, s), 7.15 (3H, m), 7.44 (4H, m); IR: 2940, 2868, 1600, 1580, 1490, 1480, 1393, 1272, 1135, 1090, 1032, 903, 833, 788 cm$^{-1}$; MS: 402 [M]$^+$, 289, 217.

EXAMPLE 130

2,3-Difluoro-4'-(5-nonyl-1,3-dioxan-2-yl)biphenylboronic acid

Quantities: compound from Example 129 (6 g, 15 mmol), n-butyllithium (10 cm$^3$, 1.55M in hexanes, 15.5 mmol) and triisopropyl borate (5.7 g, 30 mmol). The experimental procedure was as described in Example 28.

Yield=6.7 g (99.4 %); Mesomorphism (T/°C.): K 88.0N 180.0 Iso; $^1$H NMR (CDCl$_3$): δ0.89 (3H, t), 1.11 (2H, q), 1.27 (14H, m), 2.14 (1H, m), 3.55 (2H, t), 4.23 (2H, m), 5.47 (1H, s), 7.13 (1H, m), 7.45 (1H, m), 7.55 (4H, m); IR: 3700–3200, 2972, 2940, 2868, 1636, 1490, 1478, 1459, 1350, 1324, 1267, 1177, 1030, 821 cm$^{-1}$; MS: 612, 611, 542, 445 [M-1]$^+$, 428, 206.

EXAMPLE 131

2,3-Difluoro-4'-(5-nonyl-1,3-dioxan-2-yl)biphenyl-4-ol (Formula 30)

Quantities: hydrogen peroxide (10 %, 10 cm$^3$, 29 mmol), aqueous sodium carbonate (5 cm$^3$, 2M) and compound from Example 130 (1.6 g, 3.6 mmol). The experimental procedure was as described in Example 126.

Yield=1 g (66.4 %); Mesomorphism (T/°C.): K 115 (N 88.7) Iso; $^1$H NMR (CDCl$_3$): δ0.90 (3H, t), 1.12 (2H, q), 1.30 (14H, m), 2.15 (1H, m), 3.56 (2H, t), 4.26 (2H, q), 5.20 (1H, d), 5.47 (1H, s), 6.84 (1H, m), 7.07 (1H, m), 7.52 (4H, m); IR: 3600–3100, 2960, 2924, 2852, 1626, 1609, 1507, 1467, 1418, 1386, 1325, 1077, 1021, 840, 807 cm$^{-1}$; MS: 418 [M]$^+$, 289, 233.

EXAMPLE 132

(S,S)-2,3-Difluoro-4'-(5-nonyl-1,3-dioxan-2-yl)biphenyl 2-fluoro-3-methylpentate (Formula 31)

Quantities: compound from Example 131 (0.8 g, 2 mmol), (S,S)-2-fluoro-3-methylpentoic acid (0.27 g, 2 mmol), N,N'-dicyclohexylcarbodiimide (0.41 g, 2 mmol), 4-(N,N-dimethylamino)pyridine (0.03 g, 0.2 mmol). The experimental procedure was described in Example 108 except for using dichloromethane instead of THF and diethyl ether.

Yield 0.4 g (37 %); Purity (HPLC): 97.17%; [a]$_D^{25}$=0°; Ps=222 nCcm$^{-2}$ (73.9° C.); Mesomorphism: (T/°C.) K 93.5 SmC 112.6 SmA 125.1 Iso; $^1$H NMR (CDCl$_3$): δ0.89 (3H, t), 1.01 (2H, t), 1.11 (2H, q), 1.15 (3H, t), 1.27 (14H, m), 1.57 (1H, 2×m), 2.15 (1H, m), 2.23 (1H, m), 3.56 (2H, t), 4.26 (2H, q), 5.08 (1H, q), 5.47 (1H, s), 7.01 (2H, M), 7.20 (1H, m), 7.56 (4H, m); IR: 2962, 2926, 2854, 1790, 1765, 1593, 1570, 1385, 1262, 1228, 1168, 1127, 1113, 1023, 1012, 825 cm$^{-1}$; MS: 534 [M]$^+$, 417, 351, 234.

EXAMPLE 133

2,3-Difluoro-4-[4-(5-octyl-1,3-dioxan-2-yl)phenyl] benzoic acid (Formula 32)

Quantities: compound from Example 128 (5.6 g, 15.4 mmol), n-butyllithium (1.5 cm$^3$, 10.0M in hexanes, 15 mmol). The experimental procedure was as described in Example 104.

Yield=5.2 g (83.5 %); Mesomorphism (T/°C.): K 177.5N 220.9 Iso; $_1$H NMR (CDCl$_3$): δ0.89 (3H, t), 1.11 (2H, q), 1.28 (10H, m), 2.14 (1H, m), 3.57 (2H, t), 4.25 (2H, q), 5.48 (1H, s), 7.23 (1H, m), 7.58 (4H, m), 7.77 (1H, m); IR: 3700–2400, 2966, 2932, 2860, 1702, 1624, 1467, 1422, 1384, 1306, 1128, 1082, 1026, 820, 781 cm$^{-1}$; MS: 432 [M]$^+$, 261, 234.

EXAMPLE 134

(+)-2-Fluorooctyl 2,3-Difluoro-4-[4-(5-octyl-1,3-dioxan-2-yl)phenyl] benzoate (Formula 33)

Quantities: compound from Example 133 (1.7 g, 4 mmol), 2-fluorooctanol (0.6 cm$^3$, 4 mmol), N,N'-dicyclohexylcarbodiimide (0.83 g, 4 mmol), 4-(N,N'-dimethylamino)pyridine (0.05 g, 0.4 mmol). The experimental procedure was described in Example 108 except for using dichloromethane instead of THF and diehtyl ether.

Yield=0.6 g (26.7 % ); Purity (HPLC): 99.21%; [a]$_D^{23}$= +7.7°; Mesomorphism: (T/°C.) K 87.0 SmA 116.5 Iso; $^1$H NMR (CDCl$_3$): 0.90 (6H, m), 1.12 (2H, q), 1.30 (20H, m), 1.78 (2H, m), 2.15 (1H, m), 3.56 (2H, t), 4.26 (2H, q), 4.32–4.60 (2H, m), 5.48 (1H, s), 7.25 (1H, m), 7.59 (4H, m), 7.77 (1H, m); IR: 2956, 2922, 2852, 1705 1627, 1468, 1452, 1398, 1386, 1322, 1305, 1233, 1222, 1165, 1132, 1083, 1025, 820, 777 cm$^{-1}$; MS: 562 [M]$^+$, 415, 387, 275.

EXAMPLE 135

(+)-2-Octyl 2,3-Difluoro-4-[4-(5-octyl-1,3-dioxan-2-yl) phenyl] benzoate

Quantities: compound from Example 133 (1.7 g, 4 mmol), 2-octanol (0.5 cm$^3$, 4 mmol), N,N'- dicyclohexylcarbodiimide (0.83 g, 4 mmol), 4-(N,N'-dimethylamino)pyridine (0.05 g, 0.4 mmol). The experimental procedure was described in Example 134.

Yield=0.3 g (13.8 % ); Purity (HPLC): 99.40%; [a]$_D^{21.5}$ =+24.3°; Mesomorphism: (T/°C.) K 50.5 SmA 83.8 Iso; $^1$H NMR (CDCl$_3$): δ0.89 (6H, m), 1.11 (2H, q), 1.28 (20H, m), 1.36 (3H, d), 1.59–1.80 (2H, m), 2.15 (1H, m), 3.57 (2H, t), 4.26 (2H, q), 5.19 (1H, sex), 5.48 (1H, s), 7.23 (1H, m), 7.58 (4H, m), 7.72 (1H, m); IR: 2958, 2924, 2854, 1705, 1623, 1458, 1384, 1303, 1284, 1220, 1150, 1126, 1083, 1026, 823, 779 cm$^{-1}$; MS: 544 [M]$^+$, 519.

What we claim is:

1. A ferroelectric liquid crystal compound of the formula A:

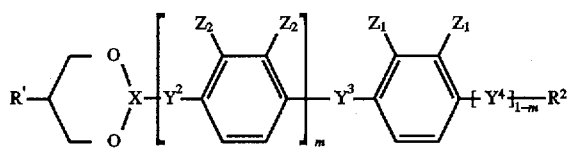

Wherein X is CH or B $R^1$, $R^2$, are each $A^1$, $OA^1$, $OCOA^2$, or $COOA^2$ $A^1$ is a straight or branched chain alkyl group containing from 5 to 10 carbon atoms and may be substituted with one or more F or CN;

$A^2$ is a straight or optically active branched chain alkyl group containing from 5 to 10 carbon atoms and may be substituted with one or more F or CN and if straight may be unsubstituted;

$Y^2$ may be $(CH_2)_p$, $(CH_2)_pCOO$ or $OCO(CH_2)_p$;

p is from 0 to 10;

m is 1, or, if X is CH and $Y^4$ is a covalent bond, may be 0, provided that if m is 1, then p is not 0;

only one of $Z_1$ and $Z_2$ are F and, when not F, are H;

$Y^3$ is a covalent bond;

$Y^4$ is a covalent bond or,

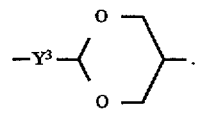

2. A compound according to claim 1 wherein $A^2$ is an optically active branched chain alkyl group containing form 5 to 10 carbon atoms and substituted by a single F or CN.

3. A compound according to claim 1, wherein $R^2$ is $OA^1$.

4. A compound according to claim 1, wherein $R^2$ is $OCOA^2$.

5. A compound according to claim 1, wherein $R^2$ is $COOA^2$.

6. A compound according to claim 1 wherein X is B; $Y^2$ is $(CH_2)_p$ wherein p is 0; m is 1; $Z_1$ is F; and $Z_2$ is H.

7. A compound according to claim 1 wherein X is CH; p is 0; m is 0 and $Y^4$ is a covalent bond.

8. Compositions comprising one or more compounds according to claim 1 as components in cells of LCD devices.

9. Composition according to claim 8, and having a Smetic C phase range of from −20° C. to 93° C.

10. Liquid crystal cells and liquid crystal devices comprising said cells containing a composition according to claim 8.

11. (2",3"-difluoro-4"-n-nonoxy-4'-biphenylyl)-4-n-nonyl-2,6-diox aborinane.

* * * * *